(12) United States Patent
Inoue et al.

(10) Patent No.: US 11,124,477 B2
(45) Date of Patent: Sep. 21, 2021

(54) SULFONIUM COMPOUND, POSITIVE RESIST COMPOSITION, AND RESIST PATTERN FORMING PROCESS

(71) Applicant: Shin-Etsu Chemical Co., Ltd., Tokyo (JP)

(72) Inventors: Naoya Inoue, Joetsu (JP); Masaki Ohashi, Joetsu (JP); Daisuke Domon, Joetsu (JP); Keiichi Masunaga, Joetsu (JP); Masaaki Kotake, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 177 days.

(21) Appl. No.: 16/559,861

(22) Filed: Sep. 4, 2019

(65) Prior Publication Data

US 2020/0071268 A1 Mar. 5, 2020

(30) Foreign Application Priority Data

Sep. 5, 2018 (JP) .............................. JP2018-166172

(51) Int. Cl.
| | | |
|---|---|---|
| C07C 311/08 | (2006.01) | |
| G03F 7/004 | (2006.01) | |
| G03F 7/039 | (2006.01) | |
| C08L 45/00 | (2006.01) | |
| C08L 33/14 | (2006.01) | |
| G03F 7/32 | (2006.01) | |

(52) U.S. Cl.
CPC .......... C07C 311/08 (2013.01); G03F 7/0045 (2013.01); G03F 7/0395 (2013.01); G03F 7/322 (2013.01); C08L 33/14 (2013.01); C08L 45/00 (2013.01)

(58) Field of Classification Search
CPC ...... G03F 7/004; G03F 7/0045; G03F 7/0046; G03F 7/039; G03F 7/0392; G03F 7/0397; C07C 381/12
See application file for complete search history.

(56) References Cited

U.S. PATENT DOCUMENTS

| | | |
|---|---|---|
| 6,479,210 B2 | 11/2002 | Kinoshita et al. |
| 6,485,883 B2 | 11/2002 | Kodama et al. |
| 6,492,091 B2 | 12/2002 | Kodama et al. |
| 8,202,677 B2 | 6/2012 | Takeda et al. |
| 8,361,693 B2 | 1/2013 | Masunaga et al. |
| 8,900,791 B2 | 12/2014 | Tsuchimura et al. |
| 2002/0006578 A1 | 1/2002 | Kodama et al. |
| 2012/0028188 A1* | 2/2012 | Ichikawa .............. G03F 7/0045 430/281.1 |
| 2013/0337382 A1* | 12/2013 | Utsumi ................. G03F 7/0045 430/285.1 |
| 2016/0349612 A1* | 12/2016 | Fujiwara ............... C07C 309/06 |
| 2018/0039177 A1 | 2/2018 | Masunaga et al. |
| 2018/0101094 A1 | 4/2018 | Hatakeyama et al. |
| 2018/0180992 A1 | 6/2018 | Kotake et al. |

FOREIGN PATENT DOCUMENTS

| | | |
|---|---|---|
| JP | 11-327143 A | 11/1999 |
| JP | 2001-330947 A | 11/2001 |
| JP | 2005227680 A * | 8/2005 |
| JP | 3955384 B2 | 8/2007 |
| JP | 4226803 B2 | 2/2009 |
| JP | 2009-53518 A | 3/2009 |
| JP | 4231622 B2 | 3/2009 |
| JP | 2010-100604 A | 5/2010 |
| JP | 4575479 B2 | 11/2010 |
| JP | 2011-22564 A | 2/2011 |
| JP | 5083528 B2 | 11/2012 |
| JP | 2018-025778 A | 2/2018 |
| JP | 2018-060069 A | 4/2018 |
| JP | 2018-109764 A | 7/2018 |
| WO | 2010/14079 A1 | 2/2010 |

OTHER PUBLICATIONS

Office Action dated Jul. 28, 2021, issued in the Counterpart JP application No. 2018-166172, with English Translation. (8 pages).

* cited by examiner

*Primary Examiner* — John A McPherson
*Assistant Examiner* — Nicholas E Brown
(74) *Attorney, Agent, or Firm* — Westerman, Hattori, Daniels & Adrian, LLP

(57) ABSTRACT

A novel sulfonium compound has formula (A). A positive resist composition comprising a polymer and a quencher containing the sulfonium compound is improved in resolution and LER during pattern formation and has storage stability. In formula (A), $R^1$, $R^2$, $R^3$, and $R^4$ are independently a $C_1$-$C_{20}$ monovalent hydrocarbon group, p is an integer of 0-5, q is an integer of 0-5, and r is an integer of 0-4.

(A)

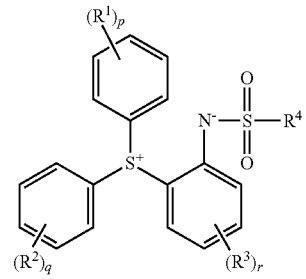

15 Claims, 3 Drawing Sheets

SULFONIUM COMPOUND, POSITIVE RESIST COMPOSITION, AND RESIST PATTERN FORMING PROCESS

CROSS-REFERENCE TO RELATED APPLICATION

This non-provisional application claims priority under 35 U.S.C. § 119(a) on Patent Application No. 2018-166172 filed in Japan on Sep. 5, 2018, the entire contents of which are hereby incorporated by reference.

TECHNICAL FIELD

This invention relates to a sulfonium compound, a positive resist composition comprising the same, and a resist pattern forming process using the resist composition.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 µm or less. High-energy radiation such as UV, deep-UV or electron beam (EB) is used as the light source for exposure of these resist compositions. In particular, while EB lithography is utilized as the ultra-fine microfabrication technique, it is also indispensable in processing a photomask blank to form a photomask for use in semiconductor device fabrication.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength of around 200 nm. These polymers, however, are expected to form useful resist materials for the EB and EUV lithography for forming patterns of finer size than the processing limit of ArF excimer laser because they offer high etching resistance.

Often used as the base polymer in positive resist compositions for EB and EUV lithography is a polymer having an acidic functional group on phenol side chain masked with an acid labile protective group. Upon exposure to high-energy radiation, the acid labile protective group is deprotected by the catalysis of an acid generated from a photoacid generator so that the polymer may turn soluble in alkaline developer. Typical of the acid labile protective group are tertiary alkyl, tert-butoxycarbonyl, and acetal groups. The use of protective groups requiring a relatively low level of activation energy for deprotection such as acetal groups offers the advantage that a resist film having a high sensitivity is obtainable. However, if the diffusion of generated acid is not fully controlled, deprotection reaction can occur even in the unexposed region of the resist film, giving rise to problems like degradation of line edge roughness (LER) and a lowering of in-plane uniformity of pattern line width (CDU).

Attempts were made to ameliorate resist sensitivity and pattern profile in a controlled way by properly selecting and combining components used in resist compositions and adjusting processing conditions. One outstanding problem is the diffusion of acid. Since acid diffusion has a material impact on the sensitivity and resolution of a chemically amplified resist composition, many studies are made on the acid diffusion problem.

Patent Documents 1 and 2 describe photoacid generators capable of generating bulky acids like benzenesulfonic acid upon exposure, for thereby controlling acid diffusion and reducing roughness. Since these acid generators are still insufficient in controlling acid diffusion, it is desired to have an acid generator with more controlled diffusion.

Patent Document 3 proposes to control acid diffusion in a resist composition by binding an acid generator capable of generating a sulfonic acid upon light exposure to a base polymer. This approach of controlling acid diffusion by binding recurring units capable of generating acid upon exposure to a base polymer is effective in forming a pattern with reduced LER. However, a problem arises with respect to the solubility in organic solvent of the base polymer having bound therein recurring units capable of generating acid upon exposure, depending on the structure and proportion of the bound units.

Patent Document 4 describes a resist composition comprising a polymer comprising recurring units having an acetal group and a sulfonium salt capable of generating an acid having a high acid strength such as fluoroalkanesulfonic acid. Regrettably, the pattern obtained therefrom has noticeable LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid that has diffused thereto. The problem arises commonly with sulfonium salts capable of generating benzenesulfonic acids as described in Patent Documents 1 and 2. It is thus desired to have an acid generator capable of generating an acid having an appropriate strength to deprotect an acetal group.

While the aforementioned methodology of generating a bulky acid is effective for suppressing acid diffusion, the methodology of tailoring a quencher (also known as acid diffusion inhibitor) is also considered effective. The quencher is, in fact, essential for controlling acid diffusion and improving resist performance.

Studies have been made on the quencher while amines and weak acid onium salts have been generally used. The weak acid onium salts are exemplified in several patent documents. Patent Document 5 describes that the addition of triphenylsulfonium acetate ensures to form a satisfactory resist pattern without T-top profile, a difference in line width between isolated and grouped patterns, and standing waves. Patent Document 6 reports improvements in sensitivity, resolution and exposure margin by the addition of sulfonic acid ammonium salts or carboxylic acid ammonium salts. Also, Patent Document 7 describes that a resist composition for KrF or EB lithography comprising a PAG capable of generating a fluorinated carboxylic acid is improved in resolution and process latitude such as exposure margin and depth of focus. These compositions are used in the KrF, EB and $F_2$ lithography. Patent Document 8 describes a positive photosensitive composition for ArF excimer laser comprising a carboxylic acid onium salt. These systems are based on the mechanism that a salt exchange occurs between a weak acid onium salt and a strong acid (sulfonic acid) generated by another PAG upon exposure, to form a weak acid and a strong acid onium salt. That is, the strong acid (sulfonic acid) having high acidity is replaced by a weak acid (carboxylic acid), thereby suppressing acid-catalyzed decomposition reaction of acid labile group and reducing or controlling the distance of acid diffusion. The onium salt apparently functions as a quencher. However, noticeable LER is still a problem in the recent progress of miniaturization when a resist composition comprising the foregoing carboxylic acid onium salt or fluorocarboxylic acid onium salt is used in patterning.

Patent Document 10 describes a quencher having a betaine structure containing a sulfonium cation moiety and a phenoxide anion moiety in a common molecule. It is presumed that this sulfonium compound takes a hypervalent structure in which the phenoxide site is at the ortho position to $S^+$, approaching to a covalent bond as the ionic bond is weakened. Allegedly, this results in the resist composition having uniform dispersion, reduced LER, and improved rectangularity. Although the resist composition comprising a quencher of betaine structure is improved in LER and rectangularity, a problem arises depending on certain components involved, that the composition becomes too much sensitive when stored at room temperature for several weeks.

CITATION LIST

Patent Document 1: JP-A 2009-053518
Patent Document 2: JP-A 2010-100604
Patent Document 3: JP-A 2011-022564
Patent Document 4: JP 5083528
Patent Document 5: JP 3955384 (U.S. Pat. No. 6,479,210)
Patent Document 6: JP-A H11-327143
Patent Document 7: JP 4231622 (U.S. Pat. No. 6,485,883)
Patent Document 8: JP 4226803 (U.S. Pat. No. 6,492,091)
Patent Document 9: JP 4575479
Patent Document 10: JP-A 2018-109764 (US 20180180992)

DISCLOSURE OF INVENTION

An object of the invention is to provide a positive resist composition which maintains a high resolution and a minimal LER during pattern formation and has storage stability.

The inventors have found that when a sulfonium compound of specific structure is formulated in a resist composition, the resist composition exhibits a high resolution, forms a pattern of good profile with a minimal LER, and has storage stability.

In one aspect, the invention provides a sulfonium compound having the formula (A).

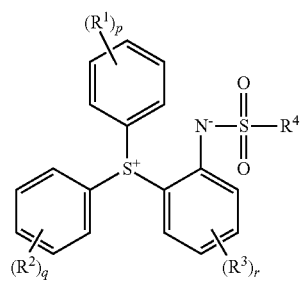

Herein $R^1$, $R^2$, $R^3$, and $R^4$ are each independently a $C_1$-$C_{20}$ monovalent hydrocarbon group which may contain a heteroatom, p and q are each independently an integer of 0 to 5, and r is an integer of 0 to 4. In case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached.

In another aspect, the invention provides a positive resist composition comprising (A) a quencher containing the sulfonium compound having formula (A).

The positive resist composition may further comprise (B) a base polymer containing a polymer adapted to be decomposed under the action of acid to increase its solubility in alkaline developer.

Preferably the polymer is a polymer comprising recurring units of at least one type selected from recurring units having the formulae (B1) to (B3).

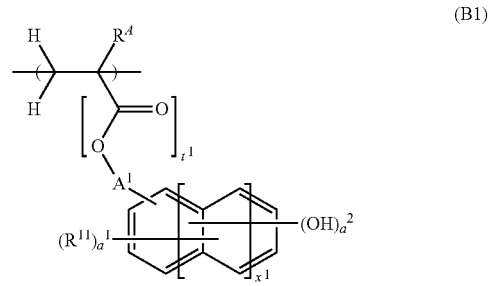

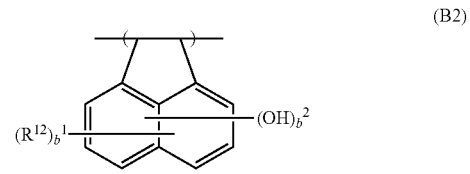

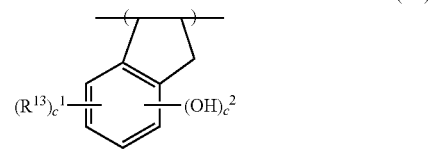

Herein $R^A$ is hydrogen, fluorine, methyl or trifluoromethyl. $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $R^{12}$ and $R^{13}$ are each independently halogen, an acetoxy group, optionally halogenated $C_2$-$C_8$ acyloxy group, optionally halogenated $C_1$-$C_8$ alkyl group, optionally halogenated $C_1$-$C_8$ alkoxy group, or optionally halogenated $C_2$-$C_8$ alkylcarbonyloxy group. $A^1$ is a single bond or $C_1$-$C_{10}$ alkanediyl group in which an ether bond may intervene in a carbon-carbon bond, $t^1$ is 0 or 1, $x^1$ is an integer of 0 to 2, $a^1$ is an integer satisfying $0 \leq a^1 \leq 5+2x^1-a^2$, $a^2$ is an integer of 1 to 3, $b^1$ is an integer of 0 to 5, $b^2$ is an integer of 1 to 3, satisfying $1 \leq b^1+b^2 \leq 6$, $c^1$ is an integer of 0 to 3, $C^2$ is an integer of 1 to 3, satisfying $1 \leq c^1+c^2 \leq 4$.

Preferably, the polymer further comprises recurring units having the formula (B4).

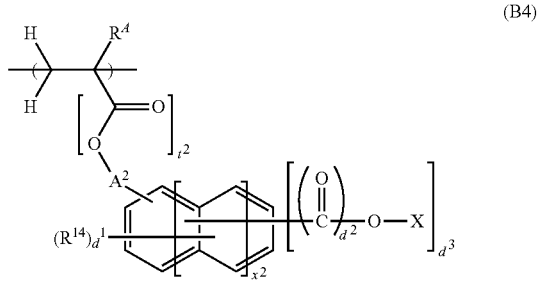

Herein $R^A$ is hydrogen, fluorine, methyl or trifluoromethyl. $R^{14}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $A^2$ is a single bond or $C_1$-$C_{10}$ alkanediyl group in which an ether bond may intervene in a carbon-carbon bond, $t^2$ is 0 or 1, $X^2$ is an integer of 0 to 2, $d^1$ is an integer satisfying: $0 \leq d^1 \leq 5+2x^2-d^3$, $d^2$ is 0 or 1, $d^3$ is an integer of 1 to 3, in case of $d^3=1$, X is an acid labile group, and in case of $d^3=2$ or 3, X is each independently hydrogen or an acid labile group, at least one X being an acid labile group.

Preferably, the polymer further comprises recurring units of at least one type selected from units having the formulae (B5) to (B7).

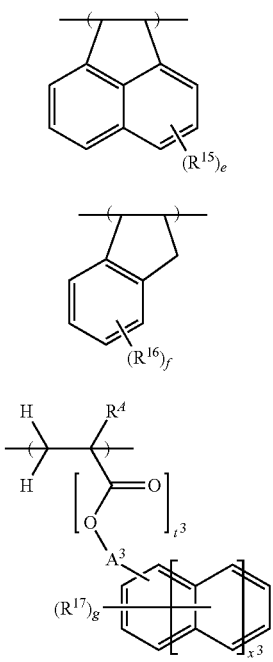

(B5)

(B6)

(B7)

Herein $R^A$ is as defined above. $R^{15}$ and $R^{16}$ are each independently halogen, an acetoxy group, optionally halogenated $C_2$-$C_8$ acyloxy group, optionally halogenated $C_1$-$C_8$ alkyl group, optionally halogenated $C_1$-$C_8$ alkoxy group, or optionally halogenated $C_2$-$C_8$ alkylcarbonyloxy group. $R^{17}$ is an acetyl group, acetoxy group, $C_1$-$C_{20}$ alkyl group, $C_1$-$C_{20}$ alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group. $A^3$ is a single bond or $C_1$-$C_{10}$ alkanediyl group in which an ether bond may intervene in a carbon-carbon bond, e is an integer of 0 to 6, f is an integer of 0 to 4, g is an integer of 0 to 5, $t^3$ is 0 or 1, and $x^3$ is an integer of 0 to 2.

Preferably, the polymer further comprises recurring units of at least one type selected from recurring units having the formulae (B8) to (B11).

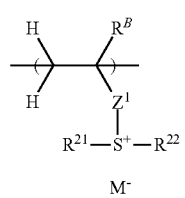

(B8)

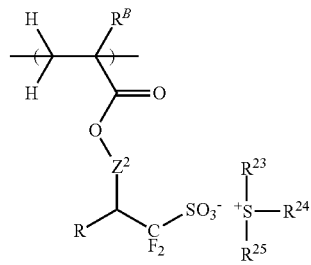

(B9)

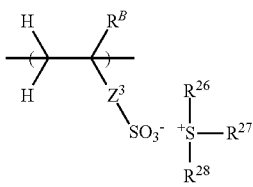

(B10)

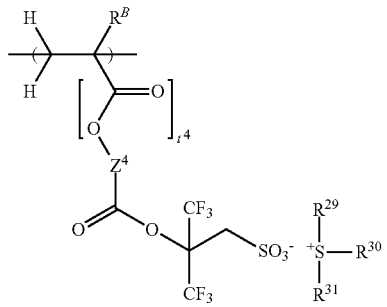

(B11)

Herein $R^B$ is each independently hydrogen or methyl. $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl, $C_2$-$C_6$ alkenediyl or phenylene group, which may contain a carbonyl moiety, ester bond, ether bond or hydroxyl moiety. $Z^2$ is a single bond or —$Z^{21}$—C(=O)—O—, $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl, $C_2$-$C_6$ alkenediyl or phenylene group, which may contain a carbonyl moiety, ester bond, ether bond or hydroxy moiety. $Z^4$ is a single bond or a $C_1$-$C_{30}$ divalent hydrocarbon group which may contain a heteroatom, $t^4$ is 0 or 1, with the proviso that $t^4$ is 0 when $Z^4$ is a single bond. $R^{21}$ to $R^{31}$ are each independently a $C_1$-$C_{20}$ monovalent hydrocarbon group which may contain a heteroatom, or $R^{21}$ and $R^{22}$ may bond together to form a ring with the sulfur atom to which they are attached, or any two of $R^{23}$, $R^{24}$ and $R^{25}$, any two of $R^{26}$, $R^{27}$ and $R^{28}$ or any two of $R^{29}$, $R^{30}$ and $R^{31}$ may bond together to form a ring with the sulfur atom to which they are attached. R is hydrogen or trifluoromethyl. $M^-$ is a non-nucleophilic counter ion.

The resist composition may further comprise (C) a fluorinated polymer comprising recurring units having the formula (C1) and recurring units of at least one type selected from units having the formulae (C2) to (C5).

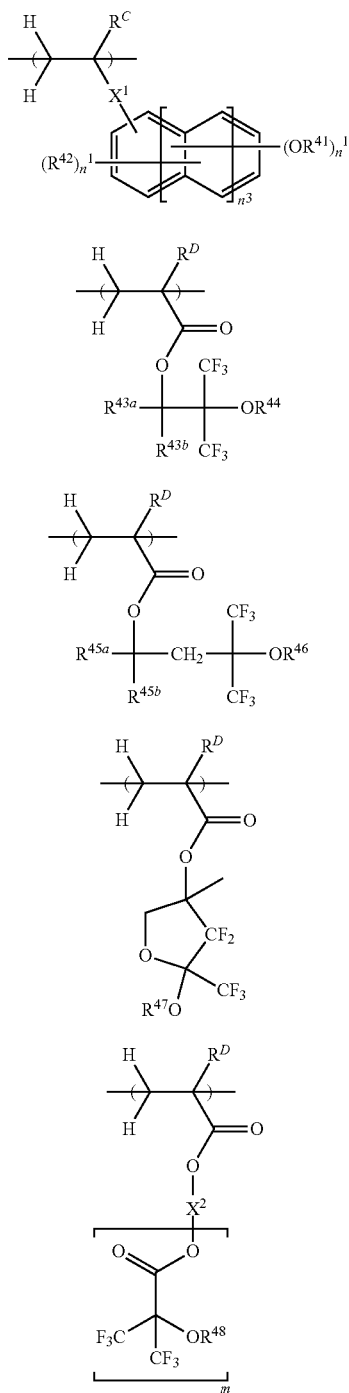

Herein $R^C$ is each independently hydrogen or methyl. $R^D$ is each independently hydrogen, fluorine, methyl or trifluoromethyl. $R^{41}$ is hydrogen or a $C_1$-$C_5$ straight or branched monovalent hydrocarbon group in which a heteroatom-containing moiety may intervene in a carbon-carbon bond. $R^{42}$ is a $C_1$-$C_5$ straight or branched monovalent hydrocarbon group in which a heteroatom-containing moiety may intervene in a carbon-carbon bond. $R^{43a}R^{43b}$, $R^{45a}$ and $R^{45b}$ are each independently hydrogen or a $C_1$-$C_{10}$ alkyl group. $R^{44}$, $R^{46}$, $R^{47}$ and $R^{48}$ are each independently hydrogen, a $C_1$-$C_{15}$ monovalent hydrocarbon group or monovalent fluorinated hydrocarbon group, or an acid labile group, with the proviso that an ether bond or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, $X^1$ is a single bond, —C(=O)—O— or —C(=O)—NH—, $X^2$ is a $C_1$-$C_{20}$ (m+1)-valent hydrocarbon group or fluorinated hydrocarbon group, $n^1$ is an integer of 1 to 3, $n^2$ is an integer satisfying: $0 \leq n^2 \leq 5+2n^3-n^1$, $n^3$ is 0 or 1, and m is an integer of 1 to 3.

The resist composition may further comprise (D) an organic solvent and/or (E) a photoacid generator.

In a further aspect, the invention provides a resist pattern forming process comprising the steps of applying the positive resist composition defined above onto a substrate to form a resist film thereon, exposing the resist film pattern wise to high-energy radiation, and developing the resist film in an alkaline developer to form a resist pattern.

Typically, the high-energy radiation is EUV or EB.

Often the substrate has an outermost surface of silicon-containing material. Typically the substrate is a photomask blank.

Also contemplated herein is a photomask blank having coated thereon the positive resist composition defined above.

Advantageous Effects of Invention

The sulfonium compound effectively functions as a quencher in a resist composition. The positive resist composition comprising the sulfonium compound exhibits a high resolution, forms a pattern with minimal LER, and has storage stability. By virtue of the action of the recurring units of formula (B1), the resist composition is fully soluble in alkaline developer and is improved in adhesion to a processable substrate when it is coated thereon as a resist film.

The pattern forming process using the positive resist composition can form a resist pattern with minimal LER while maintaining a high resolution. The invention is best suited for a micropatterning process, typically EUV or EB lithography.

DESCRIPTION OF EMBODIMENTS

Figure 1:
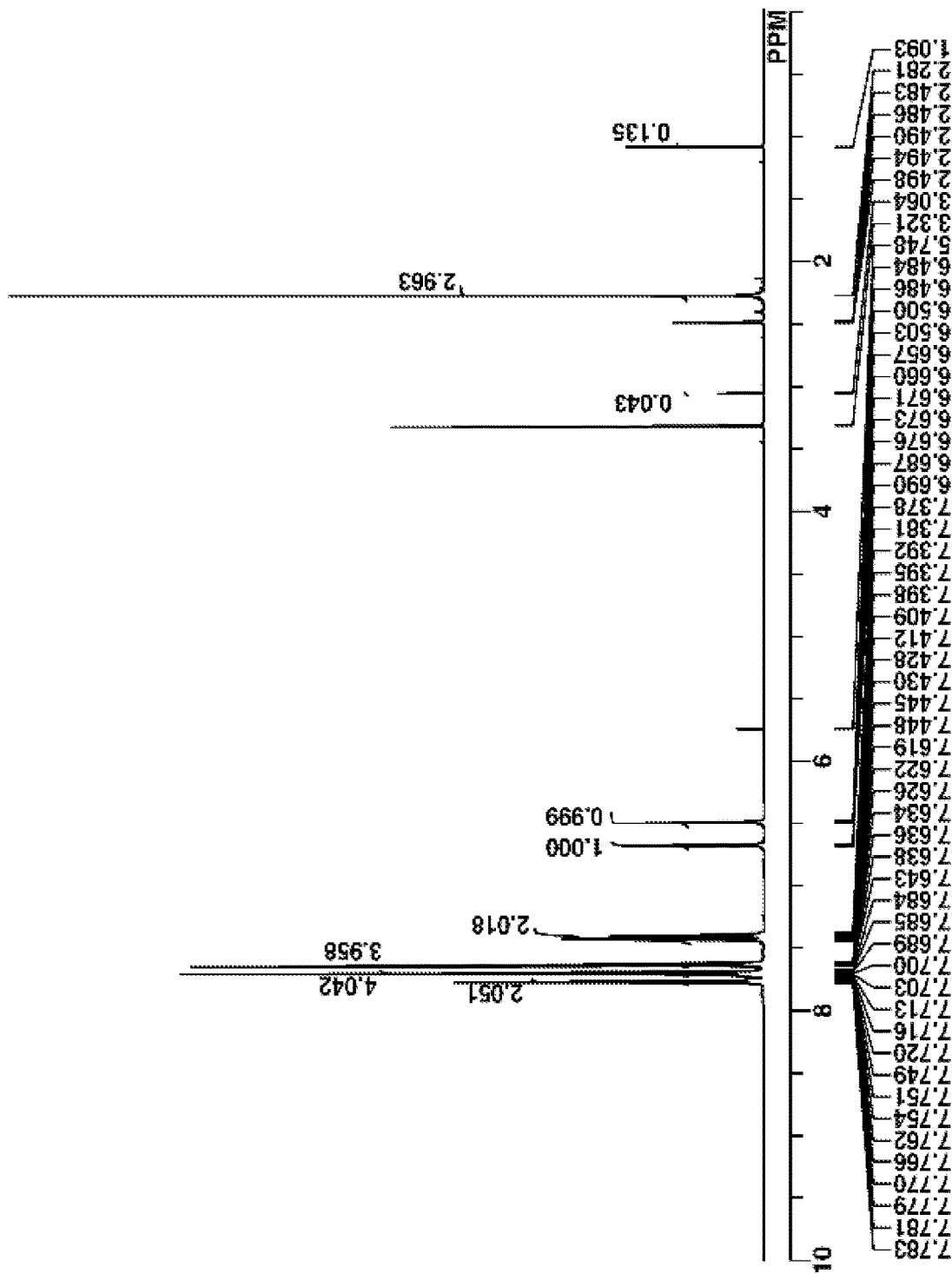
FIG. 1 is a diagram showing $^1$H-NMR spectrum of Compound Q-1 in Example 1-1-3.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line depicts a valence bond.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LER: line edge roughness
CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture.

(A) Sulfonium Compound

One embodiment of the invention is a sulfonium compound having the formula (A):

(A)

In formula (A), $R^1$, $R^2$, $R^3$, and $R^4$ are each independently a $C_1$-$C_{20}$ monovalent hydrocarbon group which may contain a heteroatom. The monovalent hydrocarbon group may be straight, branched or cyclic and examples thereof include $C_1$-$C_{20}$ alkyl groups such as methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2.6}$]decanyl, adamantyl, and adamantylmethyl, and $C_6$-$C_{20}$ aryl groups such as phenyl, naphthyl, and anthracenyl. In these hydrocarbon groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, carbamate bond, lactone ring, sultone ring, carboxylic anhydride (—C(=O)—O—C(=O)—) or haloalkyl moiety.

Of these, $R^1$ to $R^3$ are preferably selected from optionally heteroatom-containing $C_1$-$C_{12}$ alkyl groups, more preferably optionally heteroatom-containing $C_1$-$C_{10}$ alkyl groups. $R^4$ is preferably selected from optionally heteroatom-containing $C_1$-$C_{10}$ alkyl groups and $C_6$-$C_{15}$ aryl groups, more preferably optionally heteroatom-containing $C_1$-$C_6$ alkyl groups and $C_6$-$C_{10}$ aryl groups.

In formula (A), p and q are each independently an integer of 0 to 5, r is an integer of 0 to 4. Each of p, q and r is preferably 0, 1 or 2 and more preferably 0, for ease of synthesis and availability of reactants.

When p is 2 to 5, two adjoining groups $R^1$ may bond together to form a ring with the carbon atoms to which they are attached. When q is 2 to 5, two adjoining groups $R^2$ may bond together to form a ring with the carbon atoms to which they are attached. When r is 2 to 4, two adjoining groups $R^3$ may bond together to form a ring with the carbon atoms to which they are attached.

Examples of the sulfonium compound having formula (A) are given below, but not limited thereto.

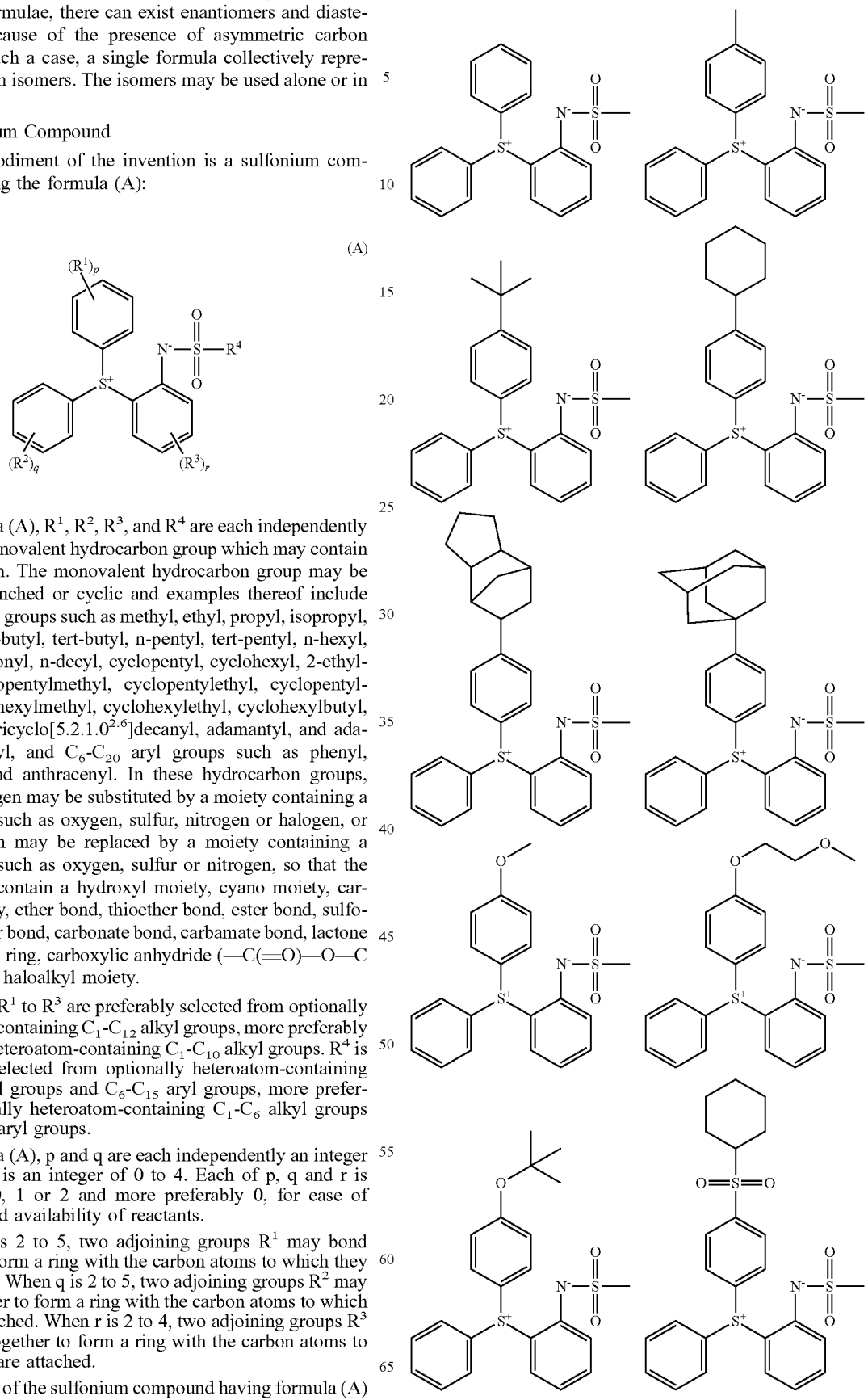

-continued
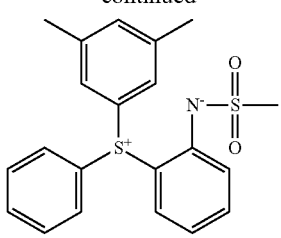
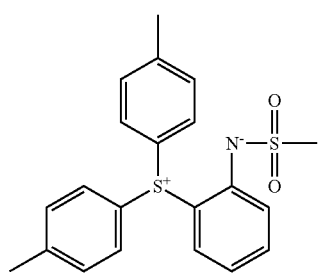
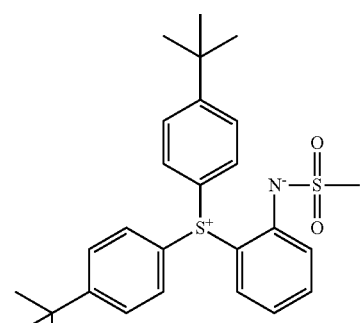
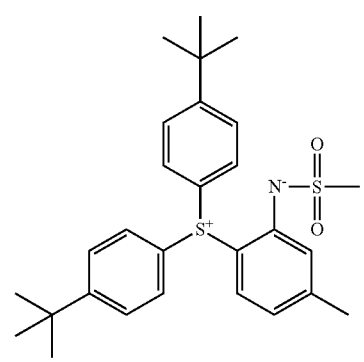
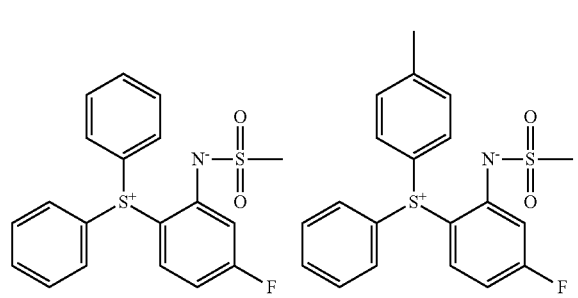
-continued
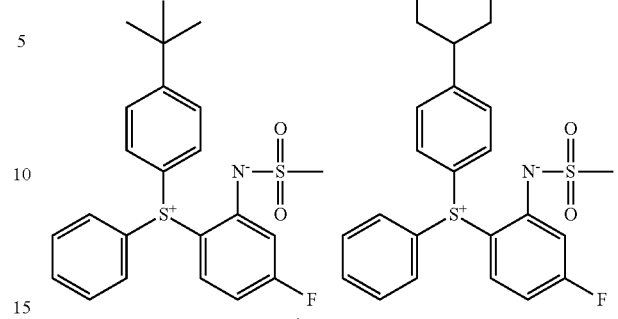
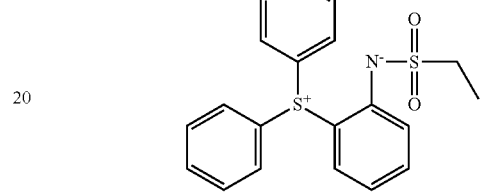
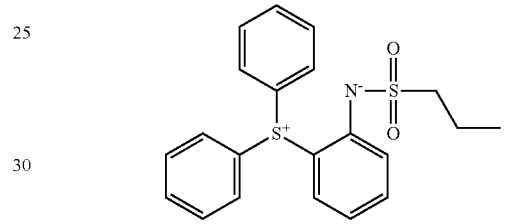
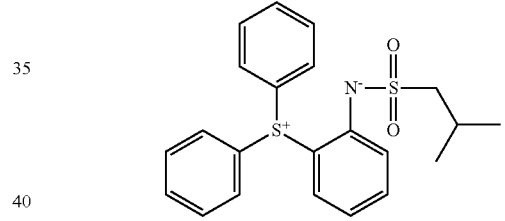
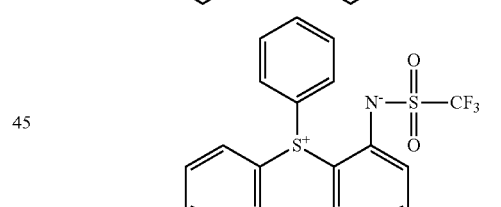
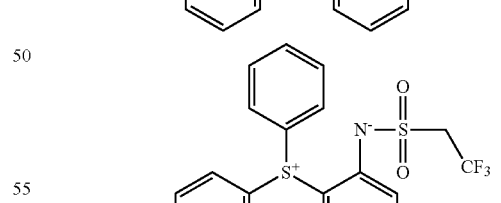
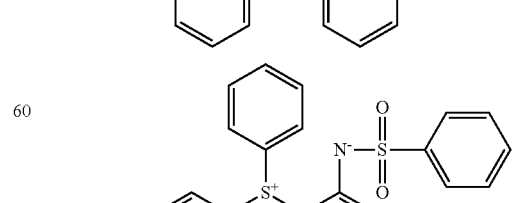

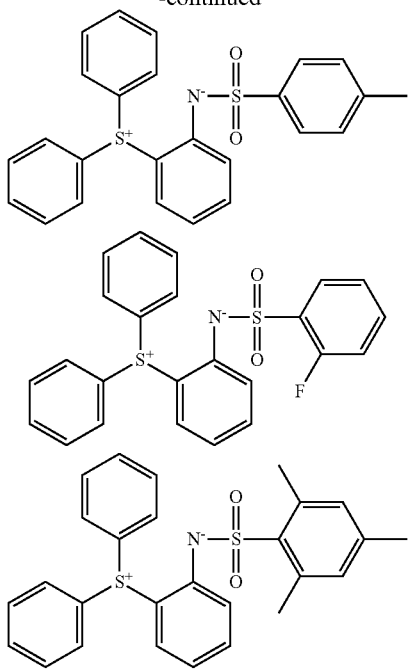

The sulfonium compound having formula (A) may be synthesized by a combination of well-known organic chemistry methods, for example, according to the scheme shown below.

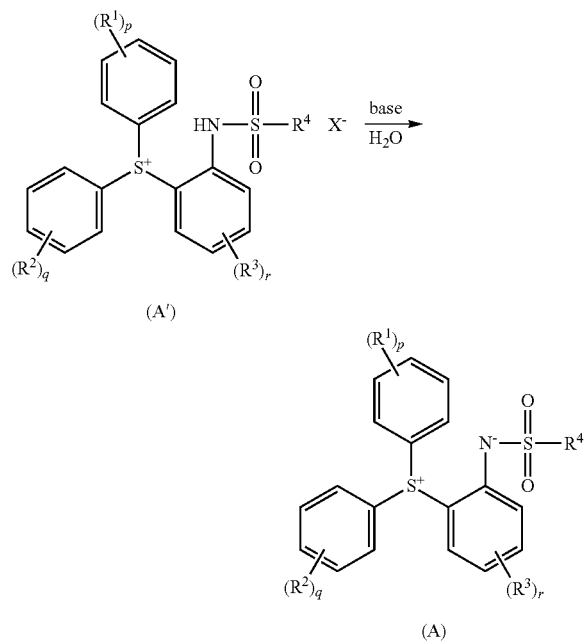

Herein $R^1$, $R^2$, $R^3$, $R^4$, p, q and r are as defined above, and $X^-$ is an anion.

There is first furnished a sulfonium salt having a sulfonium cation in which the carbon atom at α-position relative to the sulfur atom is substituted with sulfonamide. The sulfonium salt is subjected to base treatment and separatory extraction with an organic solvent-water system, whereby the inventive sulfonium compound is extracted in the organic layer. Suitable bases used herein include sodium hydroxide and tetramethylammonium hydroxide, but are not limited thereto.

The sulfonium compound defined herein functions quite effectively as a quencher when applied to a resist composition. As used herein, the term "quencher" is a compound which traps the acid generated by the PAG in the resist composition in the exposed region to prevent the acid from diffusing into the unexposed region, for thereby forming the desired pattern.

The inventive sulfonium compound follows an acid diffusion controlling mechanism which is described below. The acid generated by the PAG in the resist composition in the exposed region should have a strong acidity enough to deprotect the acid labile group on the base polymer. For example, sulfonic acid which is fluorinated at α-position relative to sulfo group and sulfonic acid which is not fluorinated are generally used in the EB lithography. In a resist composition system where the PAG and the inventive sulfonium compound co-exist, the acid generated by the PAG is trapped by the inventive sulfonium compound, and instead, the sulfonium compound is converted from betaine structure to sulfonium salt. Another mechanism that the inventive sulfonium compound itself is photo-decomposed is contemplated. In this case, a weakly acidic benzene sulfonamide compound is generated from decomposition, which has an insufficient acidity to deprotect the acid labile group on the base polymer. In either case, the inventive sulfonium compound functions as a strong quencher.

The onium salt type quencher tends to form a resist pattern with a reduced LER as compared with the conventional quenchers in the form of amine compounds. This is presumably because salt exchange between strong acid and the onium salt type quencher is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, and this smoothing effect acts to reduce the LER of a resist pattern after development.

As the compound that exerts a quencher effect via the same mechanism, Patent Document 8 and JP-A 2003-005376 report carboxylic acid onium salts, alkanesulfonic acid onium salts, and arenesulfonic acid onium salts as the quencher. On use of an alkanesulfonic acid onium salt or arenesulfonic acid onium salt, the generated acid has such an acid strength that part thereof in the highly exposed region may induce deprotection reaction of the acid labile group on the base polymer, leading to an increase of acid diffusion, which invite degradation of resist performance factors like resolution and CDU. Also in the case of carboxylic acid onium salt, the generated carboxylic acid has a weak acidity and is not reactive with the acid labile group on the base polymer. Thus the carboxylic acid onium salt achieves some improvement as quencher, but fails to satisfy an overall balance of resolution, LER and CDU in a more miniaturized region.

In contrast, the inventive sulfonium compound achieves substantial improvements in resist performance, which are not achievable with the above-mentioned quenchers. Although the reason is not clearly understood, the following reason is presumed. The inventive sulfonium compound is characterized by a betaine structure possessing a sulfonium cation and an amidate anion within a common molecule, and the amidate moiety at the ortho position relative to $S^+$. It is presumed that because of the location of amidate or anion in the vicinity of S⁺, the inventive sulfonium compound assumes a hypervalent structure, in which S⁺ and the amidate moiety are nearly in a three-center four-electron bond having a shorter bond distance than the ordinary ionic bond, that is, a covalent bond. Due to this structural specificity, the sulfonium amidate which is normally unstable remains stable. It is further presumed that since the inventive sulfonium compound is weakened in ionic bond nature as mentioned above, it is improved in organic solvent solubility and hence, more uniformly dispersed in the resist composition, leading to improvements in LER and CDU.

Although the conventional salt type quencher undergoes equilibration reaction in trapping the acid generated by the PAG and is thus inferior in acid diffusion control as discussed above, the reaction of the inventive sulfonium compound is irreversible. This is accounted for by the driving force that the sulfonium compound is converted from the betaine structure to a stabler salt type structure by trapping the acid. In addition, the inventive sulfonium compound has a counter anion in the form of strongly basic amidate. For these reasons, the inventive sulfonium compound has a very high acid diffusion controlling ability. The contrast is thus improved. There is provided a resist composition which is also improved in resolution and collapse resistance.

As the sulfonium compound of similar structural specificity having a quencher effect, Patent Document 10 describes a quencher having a betaine structure composed of a sulfonium cation and a phenoxide anion in a common molecule. A resist composition comprising this sulfonium compound, however, suffers from the problem that the composition becomes too much sensitive when stored at room temperature for several weeks. This is presumably because the phenoxide anion has high nucleophilicity due to low steric hindrance, and thus slowly reacts with a polymer as a fluorinated additive for blocking mixing of acid upon exposure to high-energy radiation and functioning as a surfactant. There is a possibility of reaction of the compound itself due to the nucleophilicity of phenoxide, and reaction with a modifying group on the base polymer.

In contrast, the inventive sulfonium compound has an anion moiety in the form of sulfonamidate, which has greater steric hindrance around the anion than the phenoxide. That is, the inventive sulfonium compound has a sufficient basicity to trap the generated acid after exposure, but does not react with the additive and other labile functional groups due to the steric hindrance of the anion moiety. The use of the inventive sulfonium compound ensures that a resist composition is designed so as to improve LER and CDU and to maintain storage stability.

In the resist composition, an appropriate amount of the sulfonium compound (A) is 0.1 to 50 parts, more preferably 1 to 30 parts by weight per 100 parts by weight of the base polymer (B). As long as its amount is in the range, the sulfonium compound fully functions as a quencher, eliminating any performance problems such as sensitivity drop, solubility shortage, and foreign particles. The sulfonium compound (A) may be used alone or in admixture of two or more.

(B) Base Polymer

The positive resist composition may further comprise (B) a base polymer containing a polymer adapted to be decomposed under the action of acid to increase its solubility in alkaline developer. Typically the polymer comprises recurring units of at least one type selected from recurring units having the formula (B1), recurring units having the formula (B2), and recurring units having the formula (B3). It is noted that the recurring units having formulae (B1), (B2) and (B3) are simply referred to as recurring units (B1), (B2) and (B3), respectively.

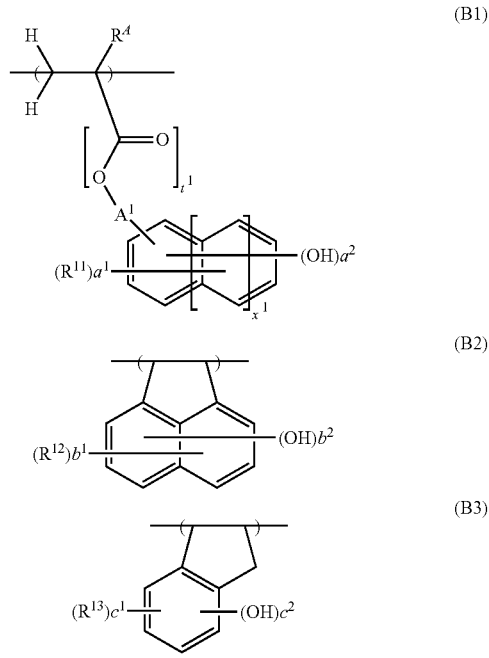

Herein $R^4$ is hydrogen, fluorine, methyl or trifluoromethyl. $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $R^{12}$ and $R^{13}$ are each independently halogen, an acetoxy group, optionally halogenated $C_2$-$C_8$ acyloxy group, optionally halogenated $C_1$-$C_8$ alkyl group, optionally halogenated $C_1$-$C_8$ alkoxy group, or optionally halogenated $C_2$-$C_8$ alkylcarbonyloxy group. $A^1$ is a single bond or a $C_1$-$C_{10}$ alkanediyl group in which an ether bond may intervene in a carbon-carbon bond, $t^1$ is 0 or 1, $x^1$ is an integer of 0 to 2, $a^1$ is an integer satisfying $0 \leq a^1 \leq 5 + 2x^1 - a^2$, $a^2$ is an integer of 1 to 3, $b^1$ is an integer of 0 to 5, $b^2$ is an integer of 1 to 3, satisfying $1 \leq b^1 + b^2 \leq 6$, $c^1$ is an integer of 0 to 3, $c^2$ is an integer of 1 to 3, satisfying $1 \leq c^1 + c^2 \leq 4$.

Examples of the alkanediyl group $A^1$ include methylene, ethylene, propanediyl, butanediyl, pentanediyl, hexanediyl, and structural isomers of carbon skeleton having a branched or cyclic structure. Where the alkanediyl group contains an ether bond, in case of $t^1=1$ in formula (B1), the ether bond may take any position excluding the position between α-carbon and β-carbon relative to the ester oxygen. In case of $t^1=0$, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the acyloxy, alkyl, alkoxy and alkylcarbonyloxy groups include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

In formula (B1), $x^1$ is an integer of 0 to 2. The relevant skeleton is a benzene skeleton in case of $x^1=0$, a naphthalene skeleton in case of $x^1=1$, and an anthracene skeleton in case of $x^1=2$. The subscript $a^1$ is an integer satisfying $0 \le a \le 5+ 2x^1-a^2$. In case of $x^1=0$, preferably $a^1$ is an integer of 0 to 3 and $a^2$ is an integer of 1 to 3. In case of $x^1=1$ or 2, preferably $a^1$ is an integer of 0 to 4 and $a^2$ is an integer of 1 to 3.

Where the recurring units (B1) are free of a linker (—CO—O-$A^1$-), that is, have formula (B1) wherein $t^1=0$ and $A^1$ is a single bond, suitable recurring units (B1) include those derived from 3-hydroxystyrene, 4-hydroxystyrene, 5-hydroxy-2-vinylnaphthalene, and 6-hydroxy-2-vinylnaphthalene.

Where the recurring units (B1) have a linker (—CO—O-$A^1$-), that is, have formula (B1) wherein $t^1=1$, preferred examples of the recurring units (B1) are given below, but not limited thereto. Herein $R^A$ is as defined above.

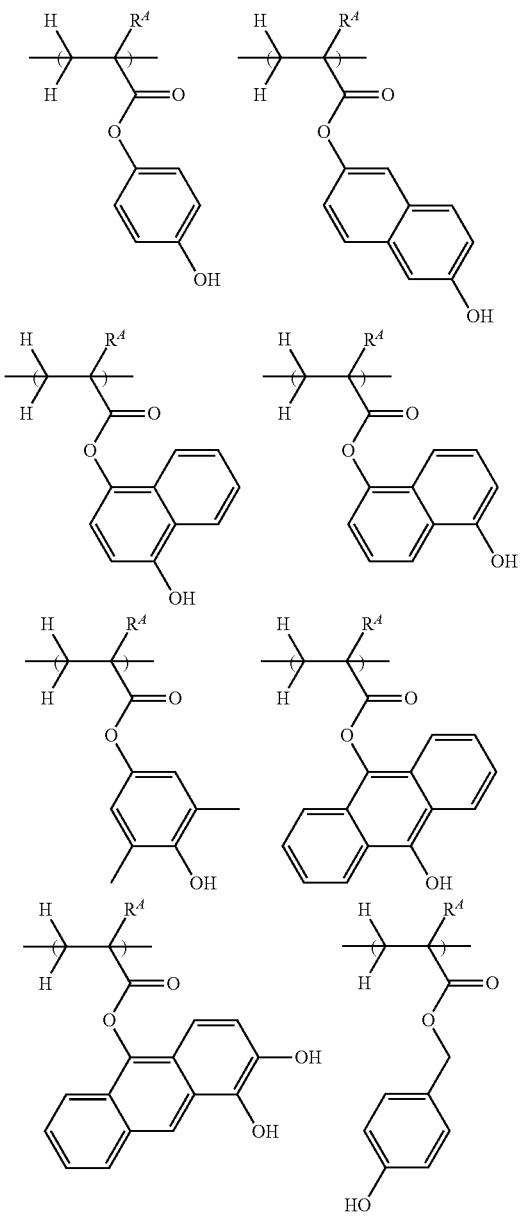

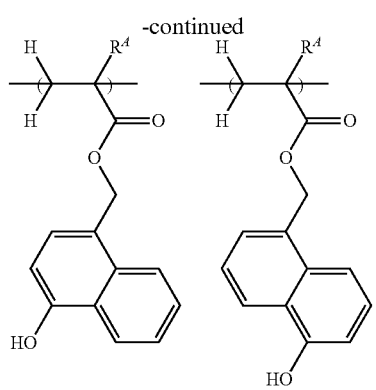

Preferred examples of the recurring units (B2) and (B3) include recurring units having the formulae (B2') and (B3'), but are not limited thereto.

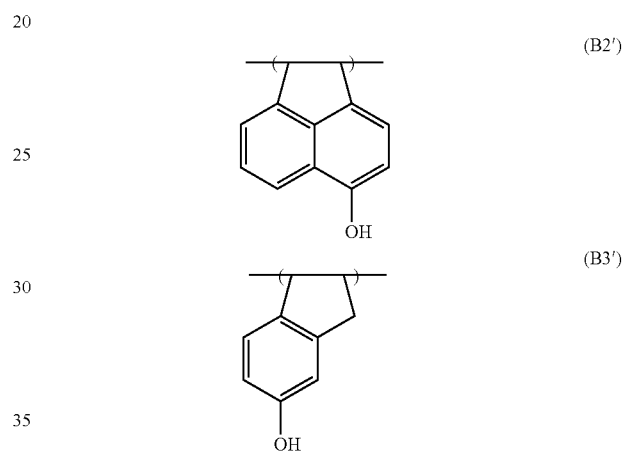

The recurring units (B1) to (B3) may be used alone or in a combination of two or more.

In order that the resist composition serve as a positive resist composition wherein the exposed region of a resist film is dissolved in alkaline aqueous solution, the polymer should preferably further comprise units having an acidic functional group protected with an acid labile group, that is, units which are protected with an acid labile group, but turn alkali soluble under the action of acid. In this case, since the acid labile group or protective group in the recurring unit undergo deprotection reaction under the action of acid, the polymer is more soluble in the alkaline developer.

Of these recurring units, recurring units having the formula (B4) are most preferred, which are also referred to as recurring units (B4).

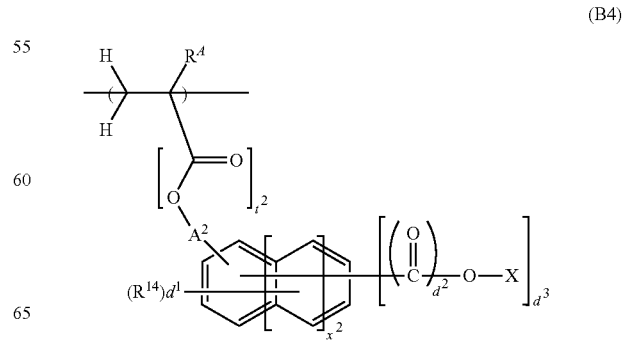

In formula (B4), $R^A$ is as defined above. $R^{14}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $A^2$ is a single bond or a $C_1$-$C_{10}$ alkanediyl group in which an ether bond may intervene in a carbon-carbon bond, $t^2$ is 0 or 1, $x^2$ is an integer of 0 to 2, $d^1$ is an integer satisfying $0 \le d^1 \le 5 + 2x^2 - d^3$, $d^2$ is 0 or 1, and $d^3$ is an integer of 1 to 3. When $d^3$ is 1, X is an acid labile group. When $d^3$ is 2 or 3, X is each independently hydrogen or an acid labile group, at least one X being an acid labile group.

Examples of the alkanediyl group $A^2$ include methylene, ethylene, propanediyl, butanediyl, pentanediyl, hexanediyl, and structural isomers of carbon skeleton having a branched or cyclic structure. Where the alkanediyl group contains an ether bond, in case of $t^2 = 1$ in formula (B4), the ether bond may take any position excluding the position between α-carbon and β-carbon relative to the ester oxygen. In case of $t^2 = 0$, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the acyloxy, alkyl and alkoxy groups represented by $R^{14}$ include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

In formula (B4), $x^2$ is an integer of 0 to 2. The relevant skeleton is a benzene skeleton in case of $x^2 = 0$, a naphthalene skeleton in case of $x^2 = 1$, and an anthracene skeleton in case of $x^2 = 2$. The subscript $d^1$ is an integer satisfying $0 \le d^1 \le 5 + 2x^2 - d^3$. In case of $X^2 = 0$, preferably $d^1$ is an integer of 0 to 3. In case of $x^2 = 1$ or 2, preferably $d^1$ is an integer of 0 to 4.

The recurring unit (B4) is the unit in which at least one of phenolic hydroxyl groups attached to aromatic ring is protected with an acid labile group, or a carboxyl group attached to aromatic ring is protected with an acid labile group. The acid labile group used herein is not particularly limited. It may be any of acid labile groups which are commonly used in many well-known chemically amplified resist compositions as long as it is eliminated with an acid to provide an acidic group.

The acid labile group is typically selected from tertiary alkyl groups and acetal groups. Selection of a tertiary alkyl group as the acid labile group is preferred in that a pattern with reduced LER is obtainable even when a resist film is coated to a thickness of 10 to 100 nm and a fine pattern having a line width of 45 nm or less is formed therefrom. Of the tertiary alkyl groups, those of 4 to 18 carbon atoms are preferred because a corresponding monomer subject to polymerization may be recovered by distillation. In the tertiary alkyl group, suitable alkyl substituents on tertiary carbon are $C_1$-$C_{15}$ alkyl groups. The $C_1$-$C_{15}$ alkyl groups may be straight, branched or cyclic, an oxygen-containing functional group such as ether bond or carbonyl may intervene between carbon atoms. Also, the alkyl substituents on tertiary carbon may bond together to form a ring with the tertiary carbon.

Examples of the alkyl substituent include methyl, ethyl, propyl, adamantyl, norbornyl, tetrahydrofuran-2-yl, 7-oxanorborman-2-yl, cyclopentyl, 2-tetrahydrofuryl, tricyclo[5.2.1.0$^{2,6}$]decyl, tetracyclo[4.4.0.1$^{2,5}$.1$^{7,10}$]dodecyl, and 3-oxo-1-cyclohexyl.

Suitable tertiary alkyl groups include, but are not limited to, tert-butyl, tert-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorboman-2-yl) ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorboman-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Also, a group of the formula (B4-1) is often used as the acid labile group. It is a good choice of the acid labile group that ensures to form a pattern having a substantially rectangular pattern-substrate interface in a consistent manner. An acetal structure is formed when X is a group of formula (B4-1).

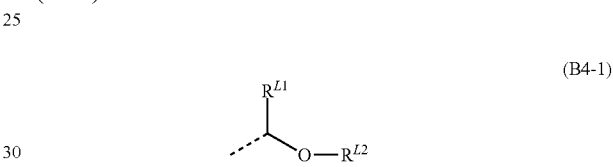

(B4-1)

In formula (B4-1), $R^{L1}$ is hydrogen or a $C_1$-$C_{10}$ alkyl group which may be straight, branched or cyclic.

A choice of $R^{L1}$ may depend on the designed sensitivity of acid labile group to acid. For example, hydrogen is selected when the acid labile group is designed to ensure relatively high stability and to be decomposed with strong acid. A straight alkyl group is selected when the acid labile group is designed to have relatively high reactivity and high sensitivity to pH changes. Although the choice varies with a particular combination of acid generator and quencher in the resist composition, $R^{L1}$ is preferably a group in which the carbon in bond with acetal carbon is secondary, when $R^{L2}$ is a relatively large alkyl group substituted at the end and the acid labile group is designed to undergo a substantial change of solubility by decomposition. Examples of $R^{L1}$ bonded to acetal carbon via secondary carbon include isopropyl, sec-butyl, cyclopentyl, and cyclohexyl.

In formula (B4-1), $R^{L2}$ is a $C_1$-$C_{30}$ alkyl group. For a higher resolution, $R^{L2}$ is preferably a $C_7$-$C_{30}$ polycyclic alkyl group. When $R^{L2}$ is a polycyclic alkyl group, a bond is preferably formed between secondary carbon on the polycyclic structure and acetal oxygen. The acetal oxygen bonded to secondary carbon on the cyclic structure, as compared with the acetal oxygen bonded to tertiary carbon on the cyclic structure, ensures that a corresponding polymer becomes a stable compound, suggesting that the resist composition has better shelf stability and is not degraded in resolution. Said acetal oxygen, as compared with $R^{L2}$ bonded to primary carbon via a straight alkanediyl group of at least one carbon atom, ensures that a corresponding polymer has a higher glass transition temperature (Tg), suggesting that a resist pattern after development is not deformed by bake.

Preferred examples of the group having formula (B4-1) are given below, but not limited thereto. Herein $R^{L1}$ is as defined above.

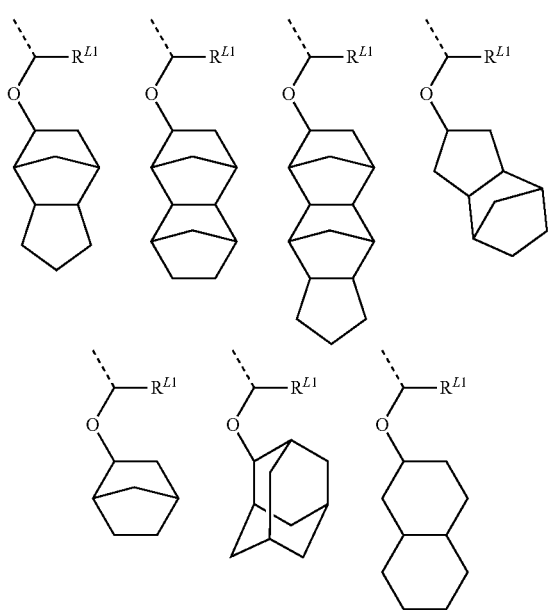

Another choice of acid labile group is a phenolic hydroxyl group having hydrogen substituted by —CH$_2$COO-(tertiary alkyl). The tertiary alkyl group used herein may be the same as the aforementioned tertiary alkyl groups used for the protection of phenolic hydroxyl group.

The recurring units (B4) may be of one type or a mixture of two or more types.

In a preferred embodiment, the polymer further comprises recurring units of at least one type selected from units of the formulae (B5), (B6) and (B7). These recurring units are simply referred to as recurring units (B5), (B6) and (B7), respectively.

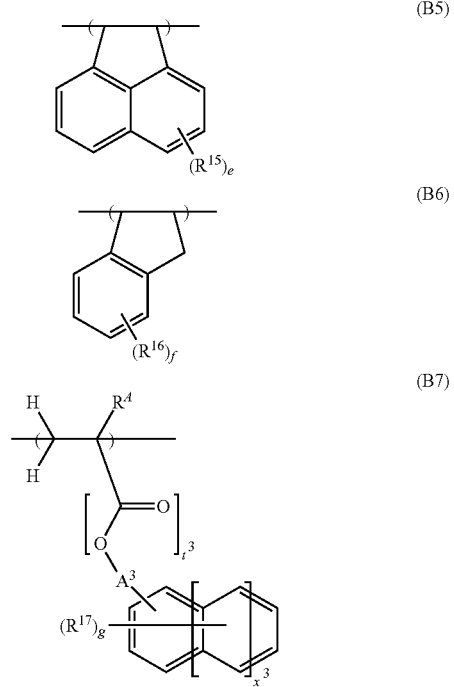

Herein $R^A$ is as defined above. $R^{15}$ and $R^{16}$ are each independently a halogen atom, acetoxy group, optionally halogenated C$_2$-C$_8$ acyloxy group, optionally halogenated C$_1$-C$_8$ alkyl group, optionally halogenated C$_1$-C$_5$ alkoxy group, or optionally halogenated C$_2$-C$_8$ alkylcarbonyloxy group. $R^{17}$ is an acetyl group, acetoxy group, C$_1$-C$_{20}$ alkyl group, C$_1$-C$_{20}$ primary alkoxy group, C$_2$-C$_{20}$ secondary alkoxy group, C$_2$-C$_{20}$ acyloxy group, C$_2$-C$_{20}$ alkoxyalkyl group, C$_2$-C$_{20}$ alkylthioalkyl group, halogen atom, nitro group, or cyano group. $A^3$ is a single bond or a C$_1$-C$_{10}$ alkanediyl group in which an ether bond may intervene in a carbon-carbon bond, e is an integer of 0 to 6, f is an integer of 0 to 4, g is an integer of 0 to 5, $t^3$ is 0 or 1, and $X^3$ is an integer of 0 to 2.

Examples of the alkanediyl group $A^3$ include methylene, ethylene, propanediyl, butanediyl, pentanediyl, hexanediyl, and structural isomers of carbon skeleton having a branched or cyclic structure. Where the alkanediyl group contains an ether bond, in case of $t^3=1$ in formula (B7), the ether bond may take any position excluding the position between α-carbon and β-carbon relative to the ester oxygen. In case of $t^3=0$, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the alkyl, alkoxy, acyloxy, and alkylcarbonyloxy groups represented by $R^{15}$ and $R^{16}$ include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

$R^{17}$ is preferably selected from chlorine, bromine, iodine, methyl, ethyl, propyl, butyl, pentyl, hexyl and structural isomers thereof, cyclopentyl, cyclohexyl, methoxy, ethoxy, propoxy, butoxy, pentyloxy, hexyloxy and structural isomers of their hydrocarbon moiety, cyclopentyloxy, and cyclohexyloxy. Inter alia, methoxy and ethoxy are useful. Also, an acyloxy group may be introduced into a polymer even at the end of polymerization by the chemical modification method and is thus advantageously used for fine adjustment of solubility of a base polymer in alkaline developer. Suitable acyloxy groups include methylcarbonyloxy, ethylcarbonyloxy, propylcarbonyloxy, butylcarbonyloxy, pentylcarbonyloxy, hexylcarbonyloxy and structural isomers thereof, cyclopentylcarbonyloxy, cyclohexylcarbonyloxy, and benzoyloxy groups. As long as the carbon count is not more than 20, the group is effective for appropriately controlling and adjusting (typically reducing) the solubility of a base polymer in alkaline developer and for preventing scum or development defects from forming. Of the preferred substituent groups mentioned above, chlorine, bromine, iodine, methyl, ethyl, and methoxy are especially useful because corresponding monomers are readily furnished.

In formula (B7), $x^3$ is an integer of 0 to 2. The relevant skeleton is a benzene skeleton in case of $x^3=0$, a naphthalene skeleton in case of $x^3=1$, and an anthracene skeleton in case of $x^3=2$. In case of $x^3=0$, preferably g is an integer of 0 to 3. In case of $x^3=1$ or 2, preferably g is an integer of 0 to 4.

Where the recurring units (B7) are free of a linker (—CO—O—$A^3$-), that is, have formula (B7) wherein $t^3=0$ and $A^3$ is a single bond, suitable recurring units (B7) include those derived from styrene, 4-chlorostyrene, 4-methylstyrene, 4-methoxystyrene, 4-bromostyrene, 4-acetoxystyrene, 2-hydroxypropylstyrene, 2-vinylnaphthalene, and 3-vinylnaphthalene.

Where the recurring units (B7) have a linker (—CO—O—A³-), that is, have formula (B7) wherein t³=1, preferred examples of the recurring units (B7) are given below, but not limited thereto. Herein R^A is as defined above.

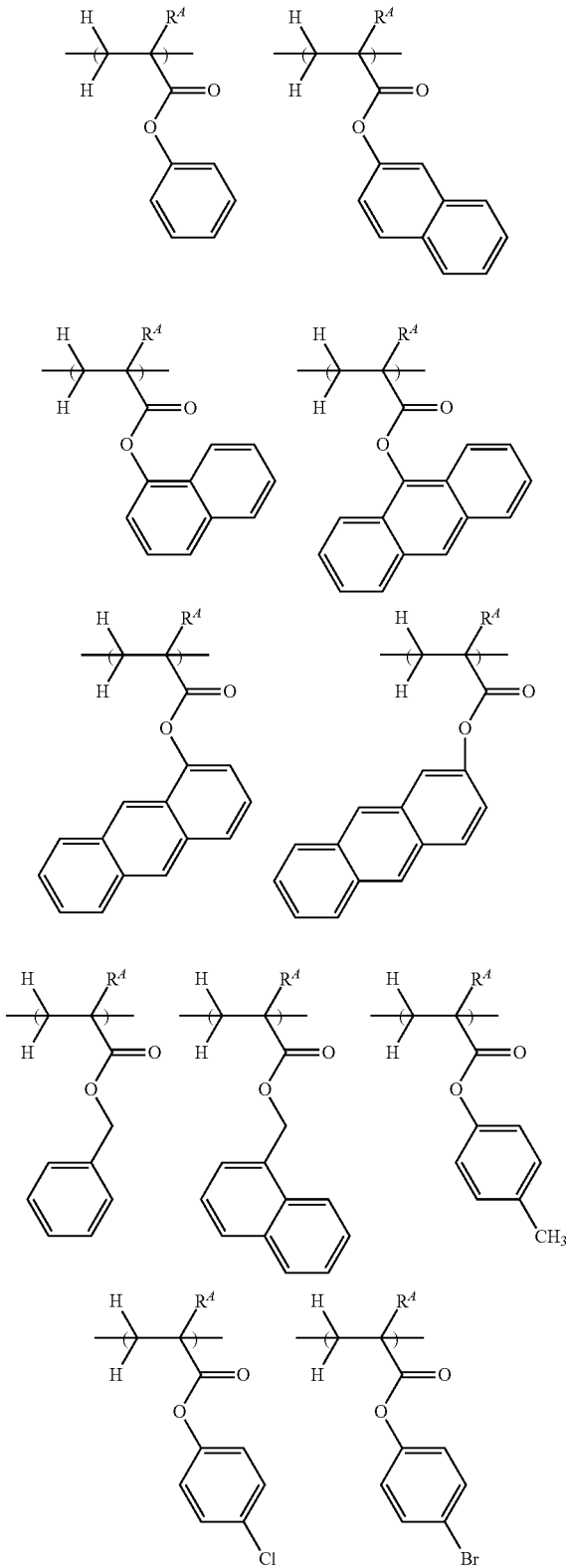

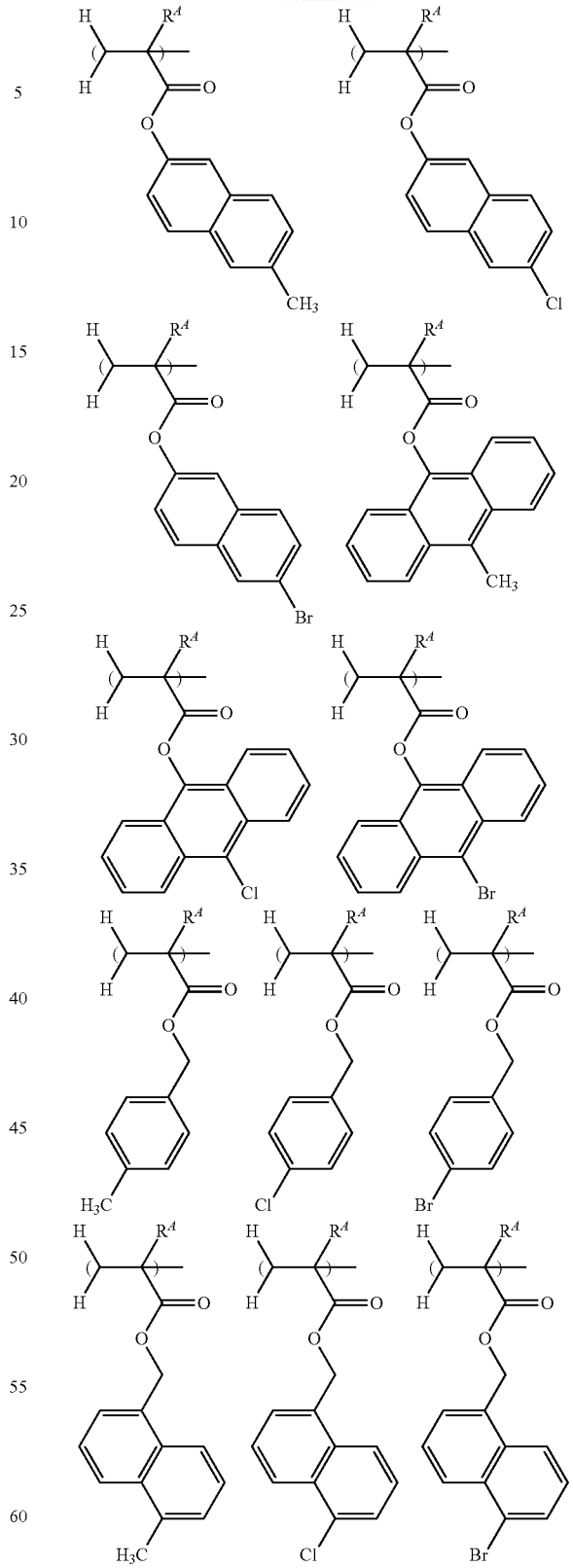

-continued

When recurring units of at least one type selected from recurring units (B5) to (B7) are incorporated, better performance is obtained because not only the aromatic ring possesses etching resistance, but the cyclic structure incorporated into the main chain also exerts the effect of improving resistance to EB irradiation during etching and pattern inspection steps.

The recurring units (B5) to (B7) may be of one type or a combination of plural types.

The polymer may further comprise recurring units of at least one type selected from recurring units having formulae (B8) to (B11). Notably these recurring units are also referred to as recurring units (B8) to (B11). This embodiment achieves effective control of acid diffusion, and forms a pattern with an improved resolution and a reduced LER.

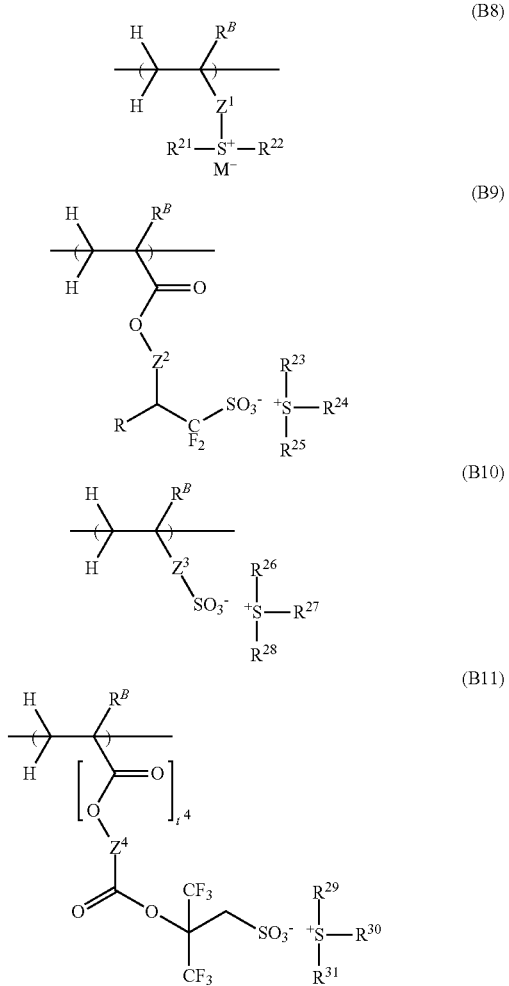

In formulae (B8) to (B11), $R^B$ is each independently hydrogen or methyl. $Z^1$ is a single bond, phenylene group, —O—$Z^{11}$—, —C(=O)—O—$Z^{11}$— or —C(=O)—NH—$Z^{11}$—, wherein $Z^{11}$ is a $C_1$-$C_6$ alkanediyl, $C_2$-$C_6$ alkenediyl or phenylene group, which may contain a carbonyl moiety, ester bond, ether bond or hydroxyl moiety. $Z^2$ is each independently a single bond or —$Z^{21}$—C(=O)—O—, wherein $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, wherein $Z^{31}$ is a $C_1$-$C_6$ alkanediyl, $C_2$-$C_6$ alkenediyl or phenylene group, which may contain a carbonyl moiety, ester bond, ether bond or hydroxyl moiety. $Z^4$ is a single bond or a $C_1$-$C_{30}$ divalent hydrocarbon group which may contain a heteroatom, and $t^4$ is 0 or 1, with the proviso that $t^4$ is 0 when $Z^4$ is a single bond.

$R^{21}$ to $R^{31}$ are each independently a $C_1$-$C_{20}$ monovalent hydrocarbon group which may contain a heteroatom. In the hydrocarbon group, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety. $R^{21}$ and $R^{22}$ may bond together to form a ring with the sulfur atom to which they are attached, any two of $R^{23}$, $R^{24}$ and $R^{25}$, any two of $R^{26}$, $R^{27}$ and $R^{28}$, or any two of $R^{29}$, $R^{30}$ and $R^{31}$ may bond together to form a ring with the sulfur atom to which they are attached. R is hydrogen or trifluoromethyl. $M^-$ is a non-nucleophilic counter ion.

In formula (B9) wherein $Z^2$ is —$Z^{21}$—C(=O)—O—, $Z^{21}$ is a divalent hydrocarbon group which may contain a heteroatom-containing moiety. Illustrative, non-limiting examples of the hydrocarbon group $Z^{21}$ are given below.

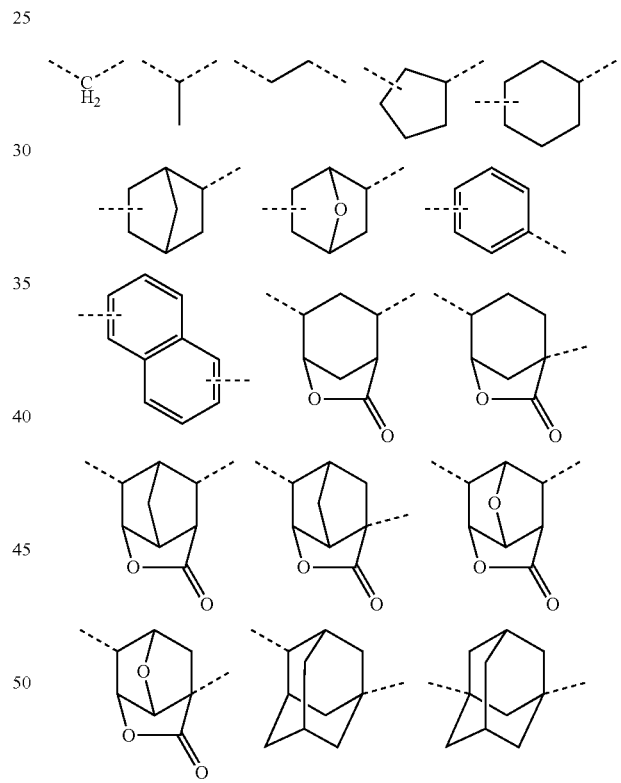

Examples of the non-nucleophilic counter ion M in recurring unit (B8) include those described in JP-A 2010-113209 and JP-A 2007-145797. Examples of the recurring unit (B9) wherein R is hydrogen include those described in JP-A 2010-116550. Examples of the recurring unit (B9) wherein R is trifluoromethyl include those described in JP-A 2010-077404. Examples of the recurring unit (B10) include those described in JP-A 2012-246265 and JP-A 2012-246426.

Preferred examples of the anion moiety in the monomer from which recurring units (B11) are derived are shown below, but not limited thereto.

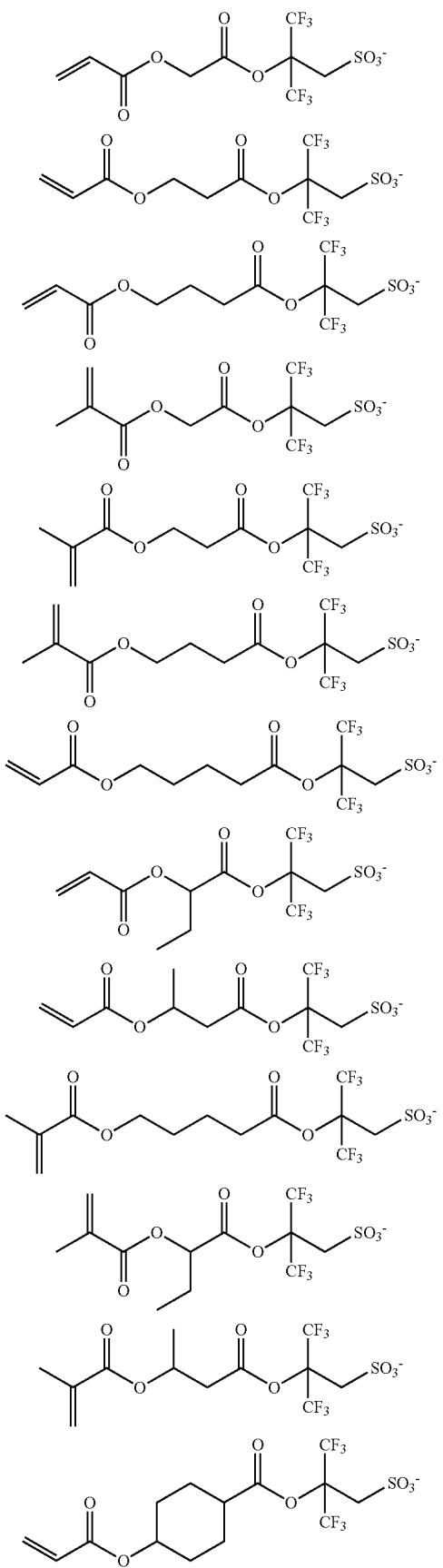
-continued
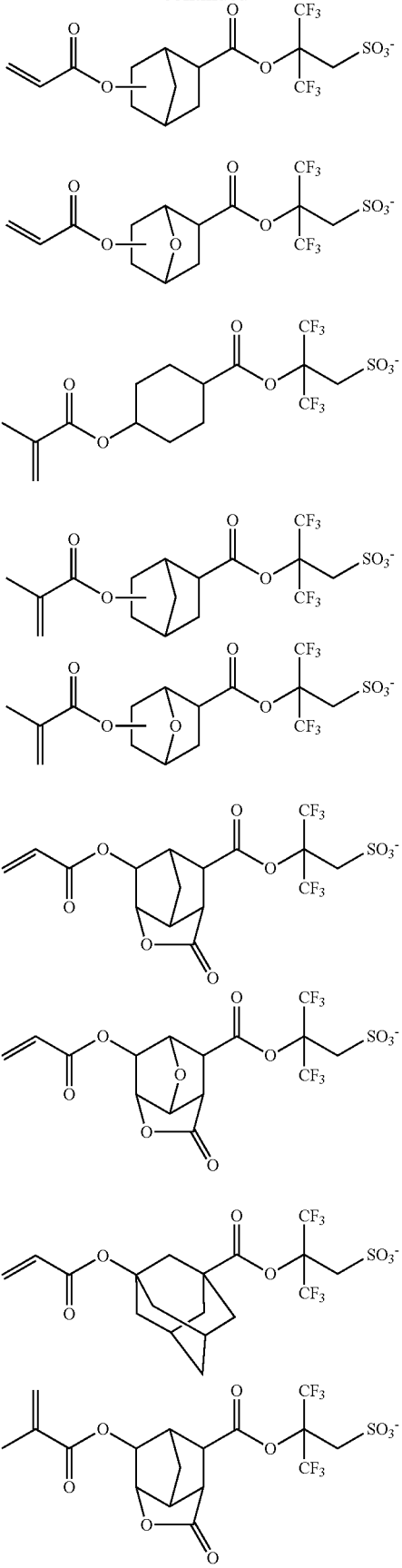

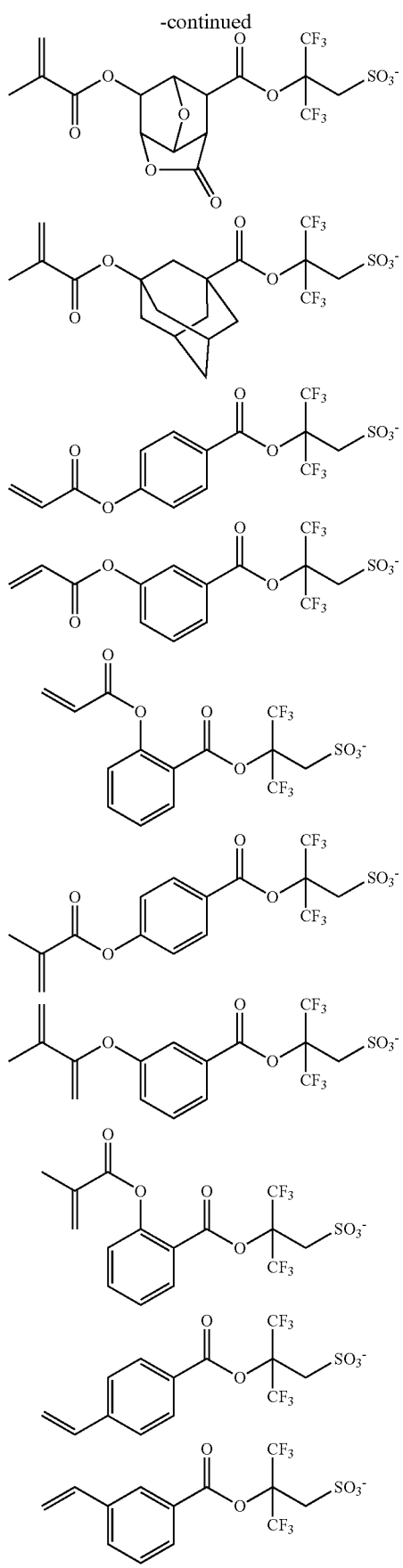

-continued

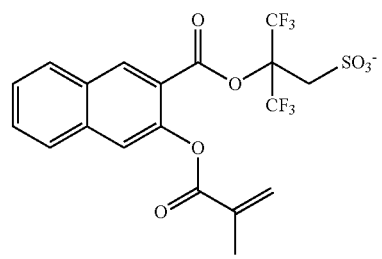

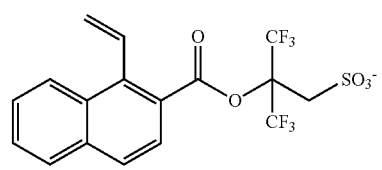

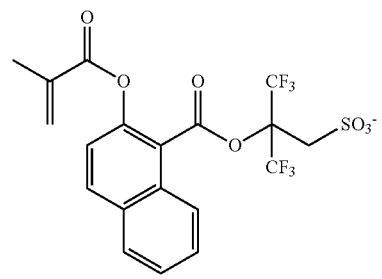

Illustrative, non-limiting examples of the sulfonium cation in formulae (B9) to (B11) wherein any two of $R^{23}$, $R^{24}$ and $R^{25}$, any two of $R^{26}$, $R^{27}$ and $R^{28}$, or any two of $R^{29}$, $R^{30}$ and $R^{31}$ bond together to form a ring with the sulfur atom to which they are attached, are shown below.

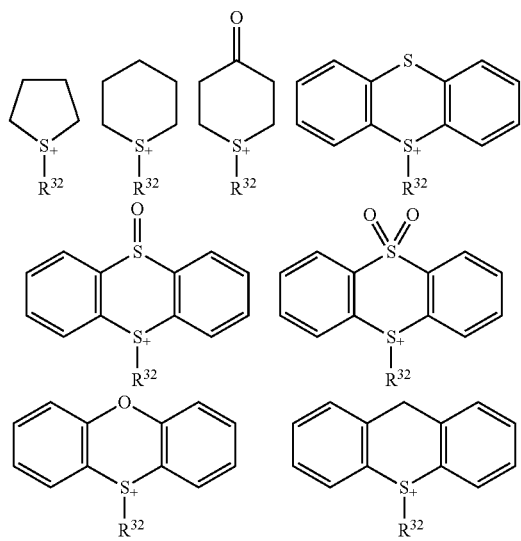

-continued

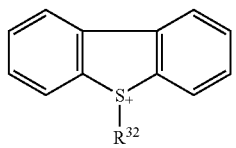 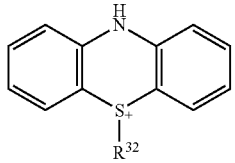

It is noted that $R^{32}$ is the same as defined and exemplified for $R^{21}$ to $R^{31}$.

Exemplary structures of the sulfonium cation in formulae (B9) to (B11) are shown below, but not limited thereto.

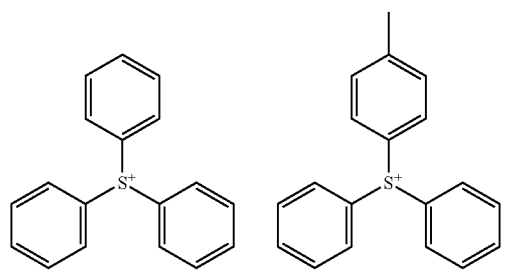

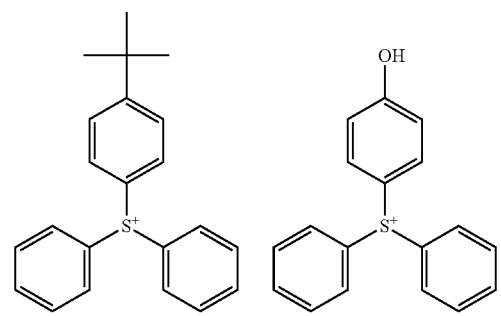

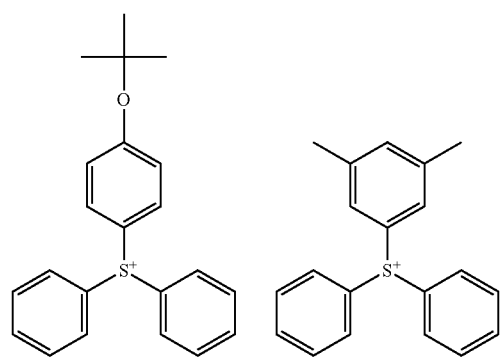

-continued
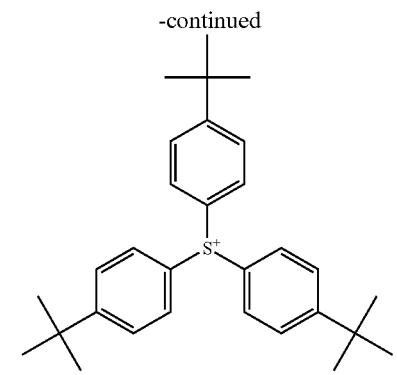
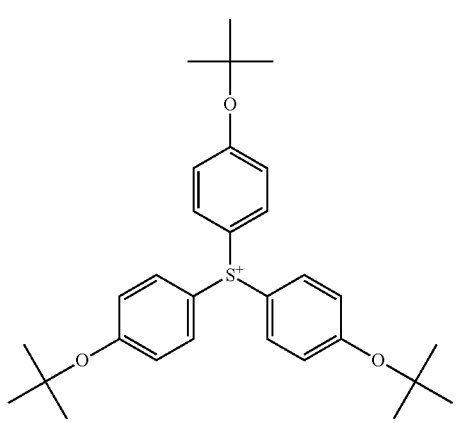
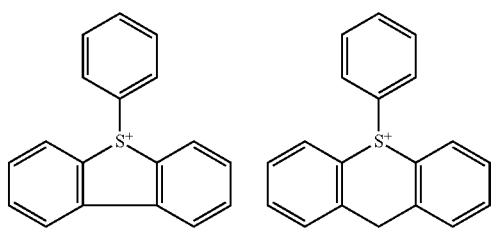
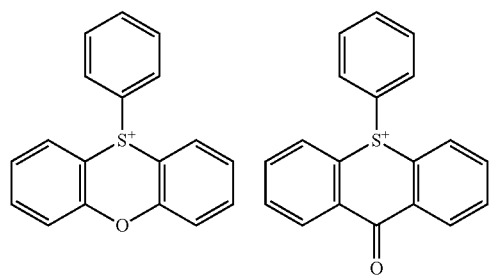
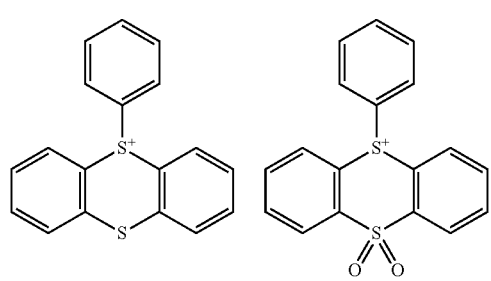
-continued
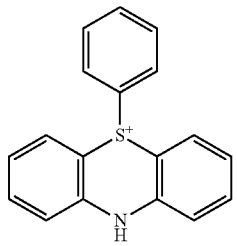 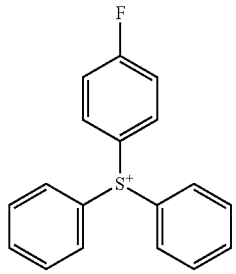
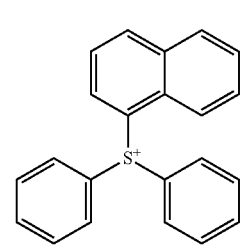 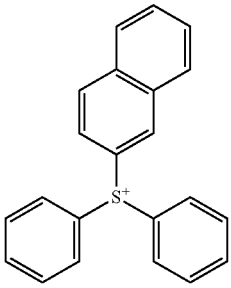
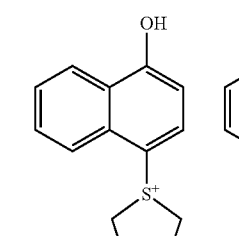 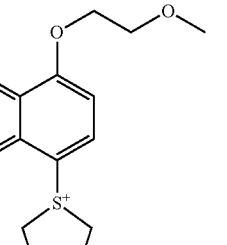
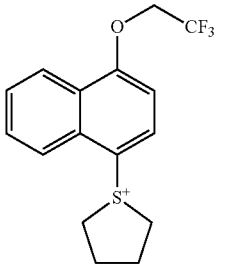 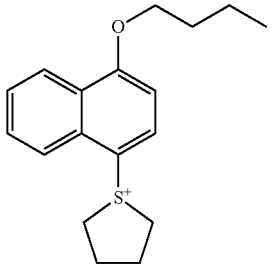
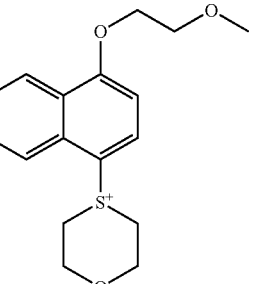 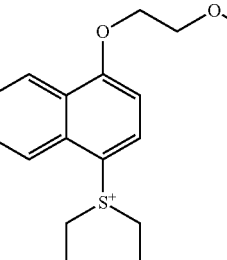
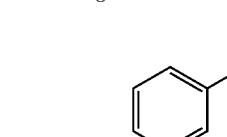 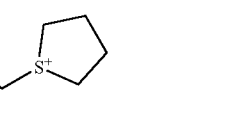
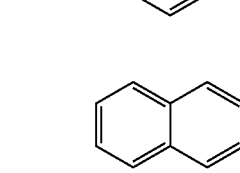 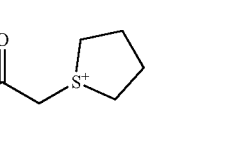

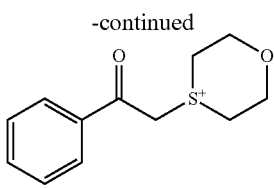

The recurring units (B8) to (B11) are units capable of generating an acid upon receipt of high-energy radiation. With the relevant units bound into a polymer, an appropriate control of acid diffusion becomes possible, and a pattern with minimal LER can be formed. Since the acid-generating unit is bound to a polymer, the chemical flare phenomenon that acid volatilizes from the exposed region and re-deposits on the unexposed region during bake in vacuum is suppressed. This is effective for reducing LER and for suppressing unwanted deprotection reaction in the unexposed region for thereby reducing defects.

In the preferred embodiment, the polymer contains recurring units of at least one type selected from recurring units (B1) to (B3), recurring units (B4), and recurring units of at least one type selected from recurring units (B5) to (B7), because both etch resistance and resolution are achievable in a compatible manner. In this embodiment, the total content of these recurring units is preferably at least 60 mol %, more preferably at least 70 mol %, and even more preferably at least 80 mol % of the overall recurring units of the polymer.

The content of recurring units (B1) to (B3) is preferably 20 to 90 mol %, more preferably 40 to 90 mol % of the overall recurring units of the polymer. The content of recurring units (B2) is preferably 5 to 45 mol %, more preferably 10 to 30 mol % of the overall recurring units of the polymer. The content of recurring units (B5) to (B7) is preferably 5 to 35 mol %, more preferably 10 to 30 mol % of the overall recurring units of the polymer in order to achieve an etch resistance improving effect. The content of recurring units (B8) to (B11) is 0 to 30 mol %, and when contained, preferably 0.5 to 30 mol %, more preferably 1 to 25 mol % of the overall recurring units of the polymer.

In addition to the above-defined polymer (referred to as Polymer A, hereinafter), the base polymer (B) may contain a polymer comprising recurring units (B1), recurring units having the formula (B12)—also referred to as recurring units (B12)—, recurring units having formula (B13)—also referred to as recurring units (B13)—, and recurring units of at least one type selected from recurring units (B8) to (B11). The latter polymer is referred to as Polymer B, hereinafter.

Herein $R^A$ is as defined above. $Z^A$ is a single bond, phenylene group, naphthylene group or (backbone)-C(=O)—O—$Z^B$—, wherein $Z^B$ is a $C_1$-$C_{10}$ alkanediyl group which may contain a hydroxyl moiety, ether bond, ester bond or lactone ring, or phenylene or naphthylene group. $X^A$ is an acid labile group. $Y^A$ is hydrogen, or a polar group containing at least one structure selected from the group consisting of hydroxyl, cyano, carbonyl, carboxyl, ether bond, ester bond, sulfonic acid ester bond, carbonate bond, lactone ring, sultone ring, and carboxylic anhydride.

Preferred examples of the recurring units (B12) and (B13) are shown below, but not limited thereto. Reference may also be made to U.S. Pat. No. 9,366,958 (JP-A 2015-206932).

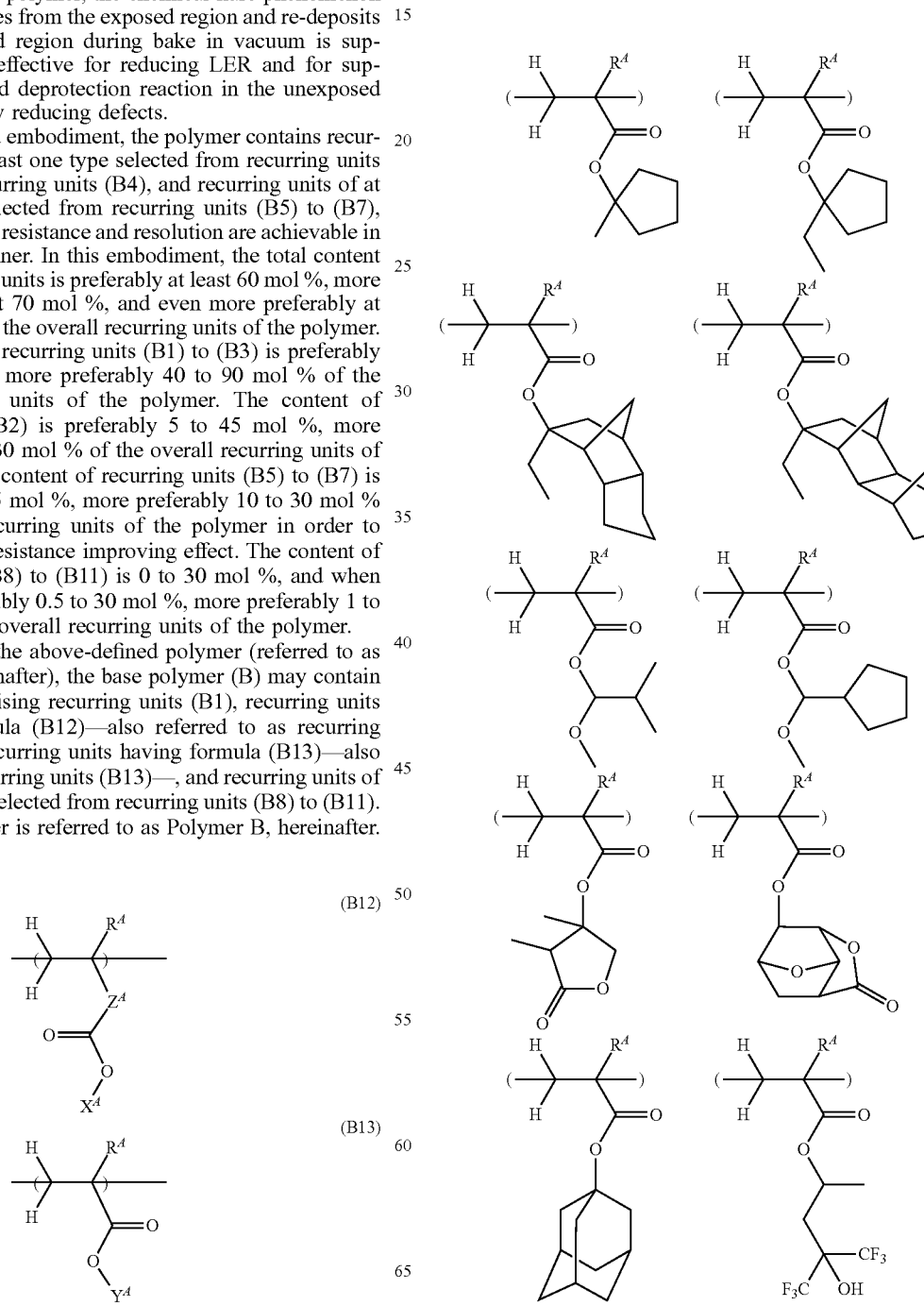

-continued

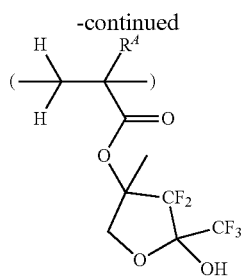

The content of recurring units (B1) is preferably 5 to 80 mol %, more preferably 10 to 40 mol % of the overall recurring units of Polymer B. The content of recurring units (B12) is preferably 5 to 90 mol %, more preferably 15 to 50 mol % of the overall recurring units of Polymer B. The content of recurring units (B13) is preferably 4.5 to 90 mol %, more preferably 15 to 50 mol % of the overall recurring units of Polymer B. The content of recurring units (B8) to (B11) is 0 to 30 mol %, and when contained, preferably 0.5 to 30 mol %, more preferably 1 to 25 mol % of the overall recurring units of Polymer B.

In addition to these units, Polymer B may comprise other recurring units, for example, any of the above-mentioned recurring units (B2) to (B7) insofar as the benefits of the invention are not compromised.

While Polymer B also functions as an acid generator, it is preferably used in an amount of 2 to 5,000 parts by weight, more preferably 10 to 1,000 parts by weight per 100 parts by weight of Polymer A.

The polymer, which is either Polymer A or Polymer B, may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The polymer should preferably have a weight average molecular weight (Mw) of 1,000 to 50,000, and more preferably 2,000 to 20,000. A Mw of at least 1,000 eliminates the risk that pattern features are rounded at their top to invite degradations of resolution and LER. A Mw of up to 50,000 eliminates the risk that LER is increased particularly when a pattern with a line width of up to 100 nm is formed. As used herein, Mw is measured by GPC versus polystyrene standards using tetrahydrofuran (THF) solvent.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

(C) Fluorinated Polymer

The resist composition may further comprise (C) a fluorinated polymer comprising recurring units having the formula (C1) and recurring units of at least one type selected from recurring units having the formulae (C2), (C3), (C4), and (C5), for the purposes of enhancing contrast, preventing chemical flare of acid upon exposure to high-energy radiation, preventing mixing of acid from an anti-charging film in the step of coating an anti-charging film-forming material on a resist film, and suppressing unexpected unnecessary pattern degradation. Notably, recurring units having formulae (C1), (C2), (C3), (C4), and (C5) are simply referred to as recurring units (C1), (C2), (C3), (C4), and (C5), respectively. Since the fluorinated polymer also has a surface active function, it can prevent insoluble residues from re-depositing onto the substrate during the development step and is thus effective for preventing development defects.

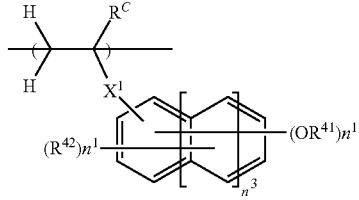 (C1)

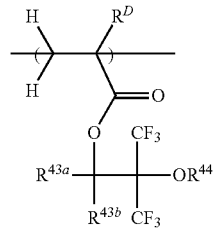 (C2)

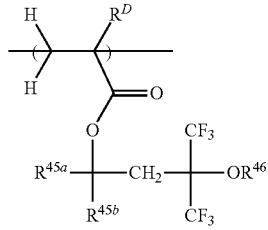 (C3)

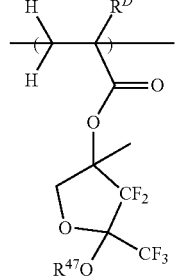 (C4)

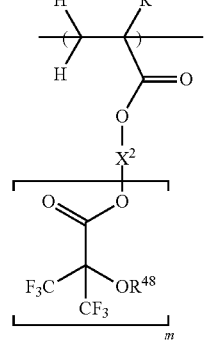 (C5)

Herein $R^C$ is each independently hydrogen or methyl. $R^D$ is each independently hydrogen, fluorine, methyl or trifluoromethyl. $R^{41}$ is hydrogen or a $C_1$-$C_5$ straight or branched monovalent hydrocarbon group in which a heteroatom may intervene in a carbon-carbon bond. $R^{42}$ is a $C_1$-$C_5$ straight or branched monovalent hydrocarbon group in which a heteroatom may intervene in a carbon-carbon bond. $R^{43a}$, $R^{43b}$, $R^{45a}$ and $R^{45b}$ are each independently hydrogen or a $C_1$-$C_{10}$ alkyl group. $R^{44}$, $R^{46}$, $R^{47}$ and $R^{48}$ are each independently hydrogen, a $C_1$-$C_{15}$ monovalent hydrocarbon group or monovalent fluorinated hydrocarbon group, or an acid labile group, with the proviso that an ether bond or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$. $X^1$ is a single bond, —C(=O)—O— or —C(=O)—NH—. $X^2$ is a $C_1$-$C_{20}$ (m+1)-valent hydrocarbon group or fluorinated hydrocarbon group. The subscript $n^1$ is an integer of 1 to 3, $n^2$ is an integer satisfying: $0 \leq n^2 \leq 5+2n^3-n^1$, $n^3$ is 0 or 1, and m is an integer of 1 to 3.

Suitable monovalent hydrocarbon groups include alkyl, alkenyl and alkynyl groups, with the alkyl groups being preferred. Suitable alkyl groups include methyl, ethyl, n-propyl, isopropyl, n-butyl, isobutyl, sec-butyl, and n-pentyl. In these groups, a moiety containing a heteroatom such as oxygen, sulfur or nitrogen may intervene in a carbon-carbon bond.

In formula (C1), —OR$^{41}$ is preferably a hydrophilic group. In this case, $R^{41}$ is preferably hydrogen or a $C_1$-$C_5$ alkyl group in which oxygen intervenes in a carbon-carbon bond.

In formula (C1), $X^1$ is preferably —C(=O)—O— or —C(=O)—NH—. The inclusion of carbonyl in $X^1$ enhances the ability to trap the acid originating from the anti-charging film. Also preferably $R^C$ is methyl. A polymer wherein $R^C$ is methyl is a rigid polymer having a high glass transition temperature (Tg) which is effective for suppressing acid diffusion. As a result, the stability with time of a resist film is improved, and neither resolution nor pattern profile is degraded.

Examples of the recurring unit (C1) are given below, but not limited thereto. Herein $R^C$ is as defined above.

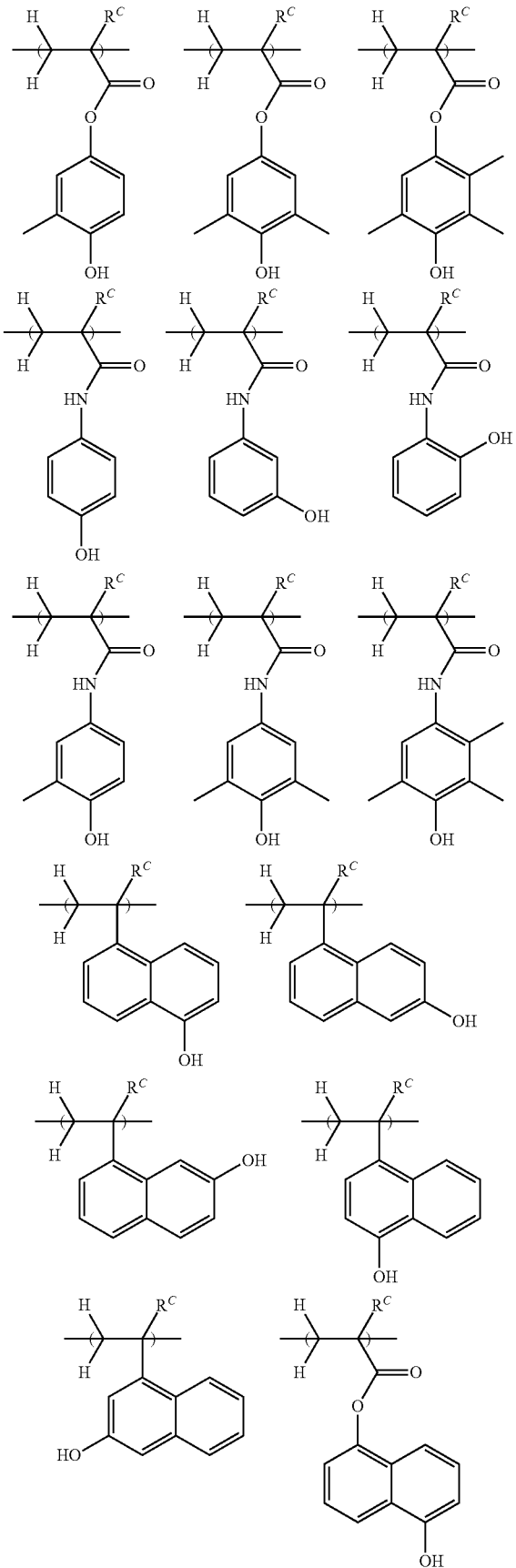

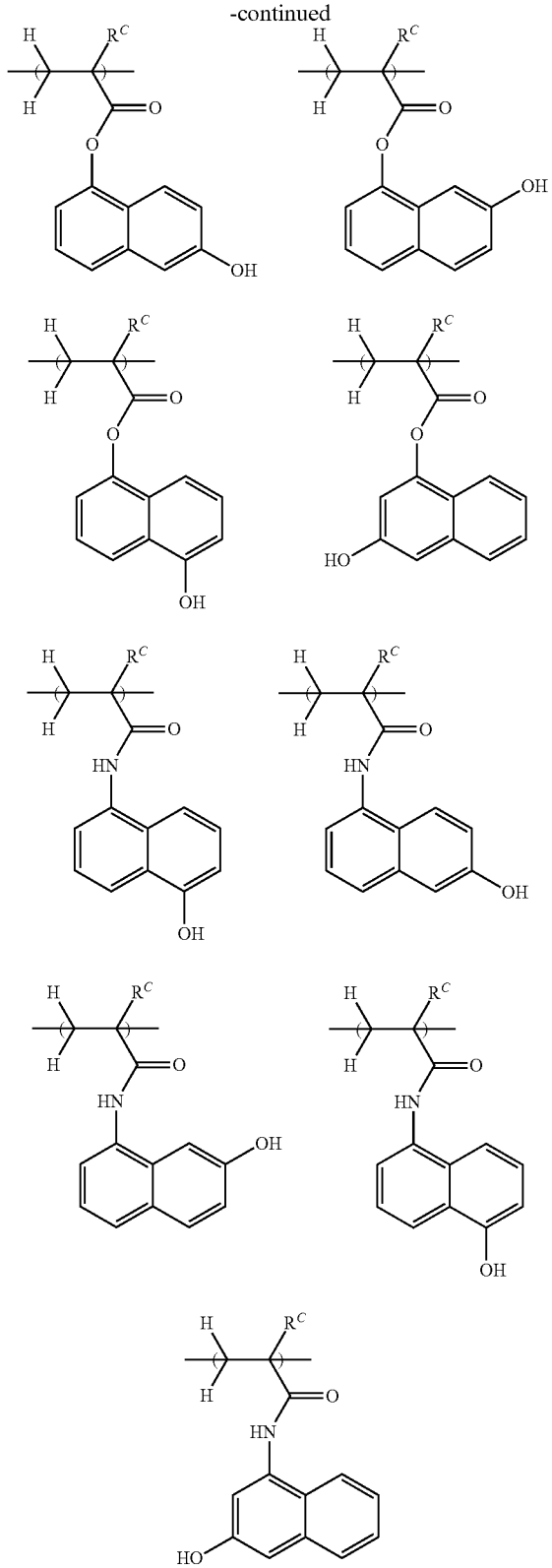

adamantyl, and norbornyl. Inter alia, $C_1$-$C_6$ straight, branched or cyclic alkyl groups are preferred.

In formulae (C2) to (C5), examples of the monovalent hydrocarbon group represented by $R^{44}$, $R^{46}$, $R^{47}$ and $R^{48}$ include alkyl, alkenyl and alkynyl groups, with the alkyl groups being preferred. Suitable alkyl groups include n-undecyl, n-dodecyl, tridecyl, tetradecyl and pentadecyl as well as those exemplified above. The monovalent fluorinated hydrocarbon groups correspond to the foregoing monovalent hydrocarbon groups in which some or all carbon-bonded hydrogen atoms are substituted by fluorine atoms.

Examples of the $C_1$-$C_{20}$ (m+1)-valent hydrocarbon group or fluorinated hydrocarbon group include the foregoing monovalent hydrocarbon groups and monovalent fluorinated hydrocarbon groups, with a number (m) of hydrogen atoms being eliminated.

Examples of the recurring units (C2) to (C5) are given below, but not limited thereto. Herein $R^D$ is as defined above.

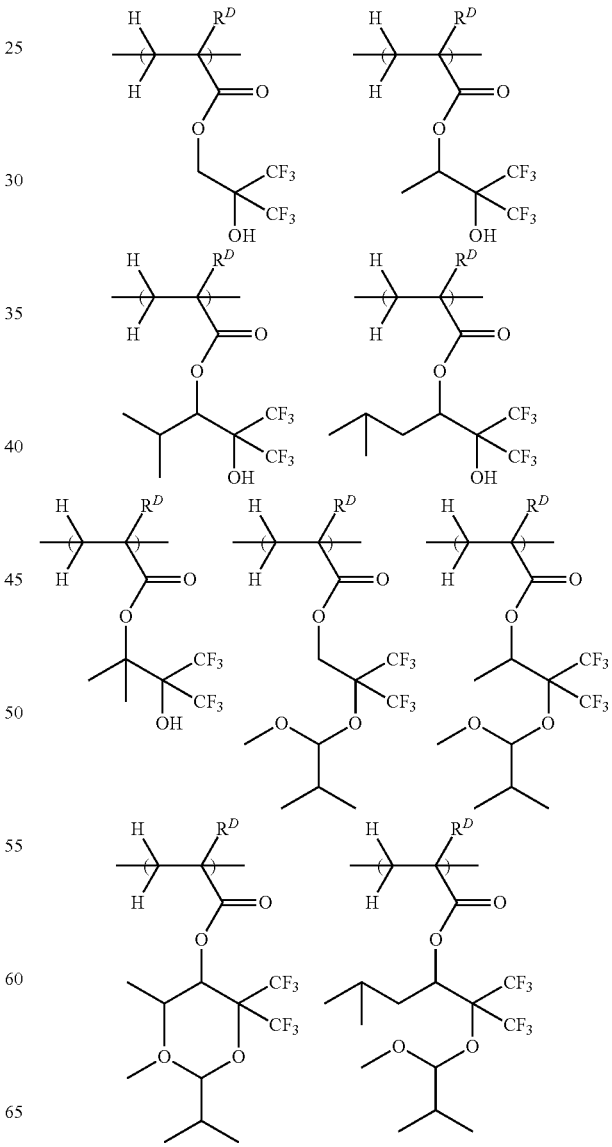

In formulae (C2) and (C3), examples of the alkyl group represented by $R^{43a}$, $R^{43b}R^{45a}$ and $R^{45b}$ include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, -continued
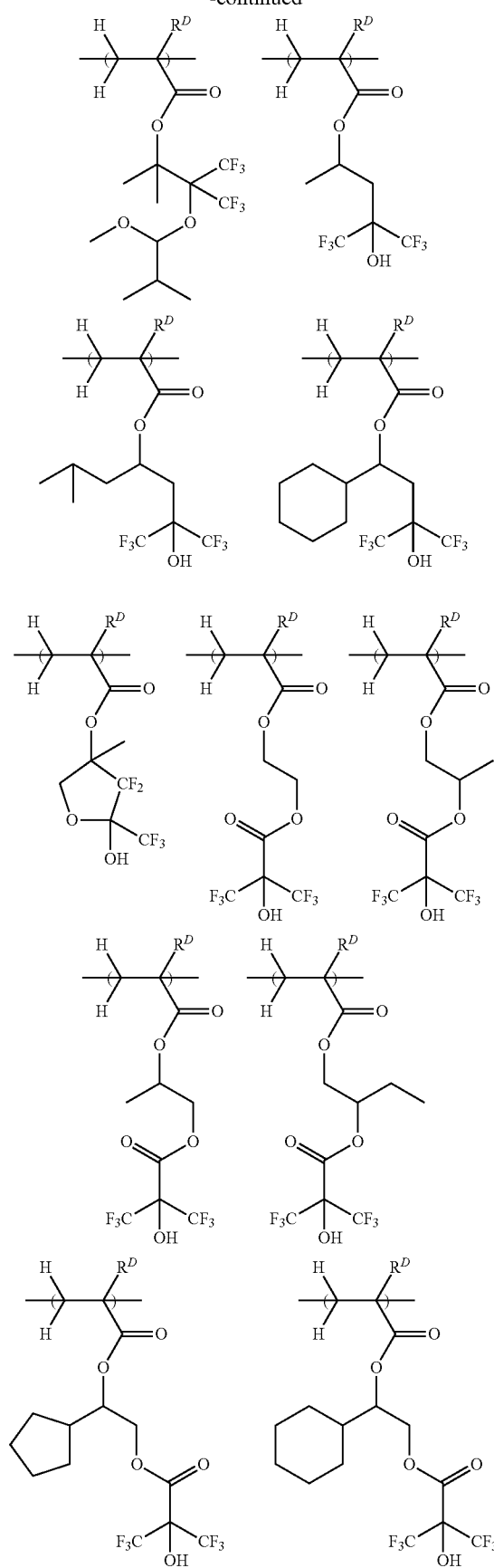
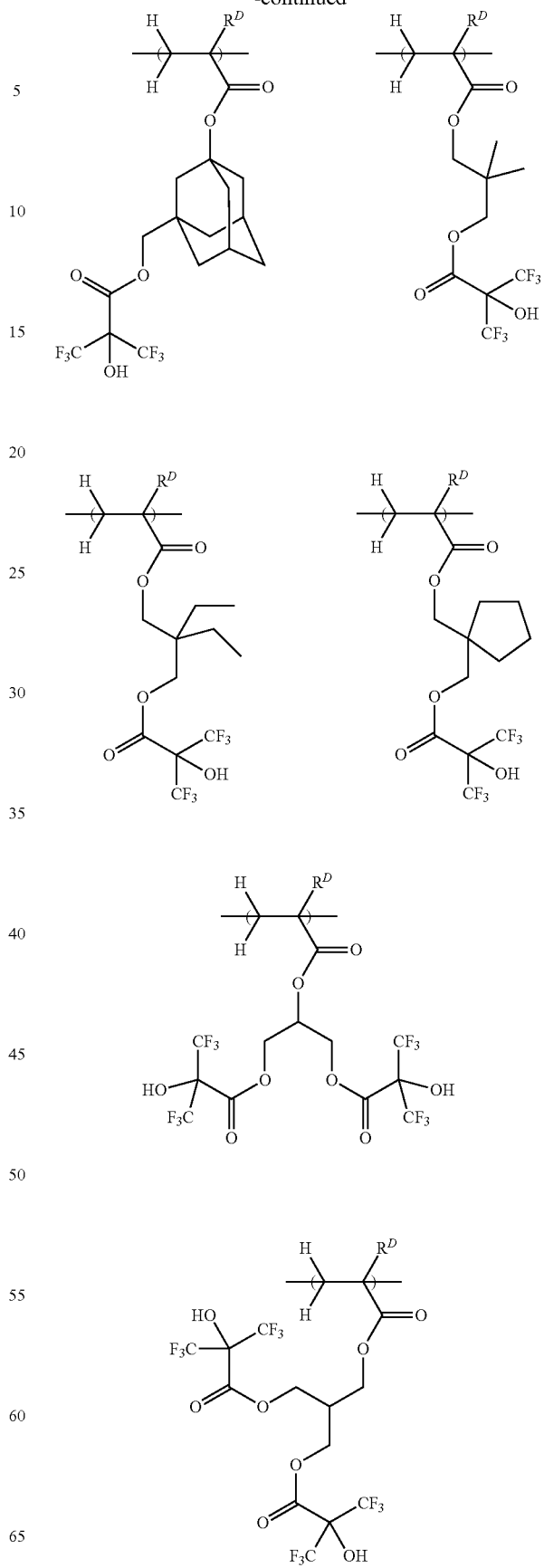

-continued

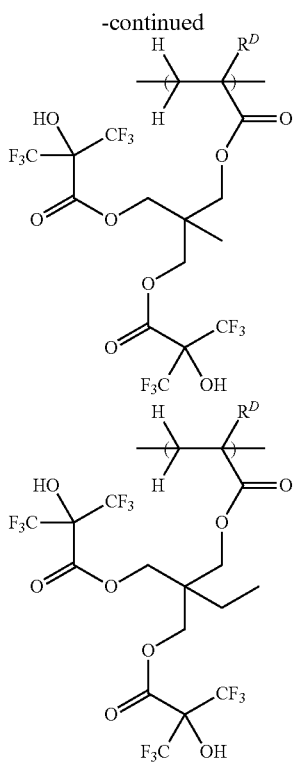

The recurring unit (C1) is preferably incorporated in an amount of 5 to 85 mol %, more preferably 15 to 80 mol % based on the overall recurring units of the fluorinated polymer (C). The recurring units (C2) to (C5), which may be used alone or in admixture, are preferably incorporated in an amount of 15 to 95 mol %, more preferably 20 to 85 mol % based on the overall recurring units of the fluorinated polymer (C).

The fluorinated polymer (C) may comprise additional recurring units as well as the recurring units (C1) to (C5). Suitable additional recurring units include those described in U.S. Pat. No. 9,091,918 (JP-A 2014-177407, paragraphs [0046]-[0078]). When the fluorinated polymer (C) comprises additional recurring units, their content is preferably up to 50 mol % based on the overall recurring units.

The fluorinated polymer (C) may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The fluorinated polymer (C) should preferably have a Mw of 2,000 to 50,000, and more preferably 3,000 to 20,000. A fluorinated polymer with a Mw of less than 2,000 helps acid diffusion, degrading resolution and detracting from age stability. A polymer with too high Mw has a reduced solubility in solvent, leading to coating defects. The fluorinated polymer preferably has a dispersity (Mw/Mn) of 1.0 to 2.2, more preferably 1.0 to 1.7.

The fluorinated polymer (C) is preferably used in an amount of 0.01 to 30 parts, more preferably 0.1 to 20 parts by weight per 100 parts by weight of the base polymer (B).

(D) Organic Solvent

The positive resist composition may further comprise (D) an organic solvent. The organic solvent used herein is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, propylene glycol monomethyl ether, cyclohexanone, ethyl lactate, γ-butyrolactone, and mixtures thereof.

An appropriate amount of the organic solvent (D) used is 200 to 10,000 parts, more preferably 400 to 5,000 parts by weight per 100 parts by weight of the base polymer (B).

(E) Photoacid Generator

The resist composition may further comprise (E) a photoacid generator (PAG) in order that the composition function as a chemically amplified positive resist composition. The PAG may be any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. These PAGs may be used alone or in admixture of two or more.

Suitable PAGs include nonafluorobutane sulfonate, partially fluorinated sulfonates described in JP-A 2012-189977, paragraphs [0247]-[0251], partially fluorinated sulfonates described in JP-A 2013-101271, paragraphs [0261]-[0265], and those described in JP-A 2008-111103, paragraphs [0122]-[0142] and JP-A 2010-215608, paragraphs [0080]-[0081]. Among others, arylsulfonate and alkanesulfonate type PAGs are preferred because they generate acids having an appropriate strength to deprotect the acid labile group in recurring unit (B4).

The preferred acid generators are compounds having a sulfonium anion of the structure shown below. Notably the cation that pairs with the anion is as exemplified for the sulfonium cation in formulae (B9) to (B11).

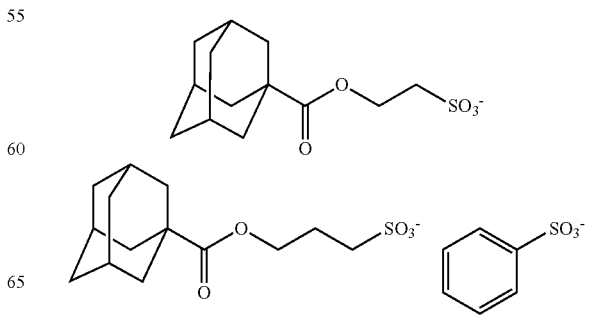

-continued
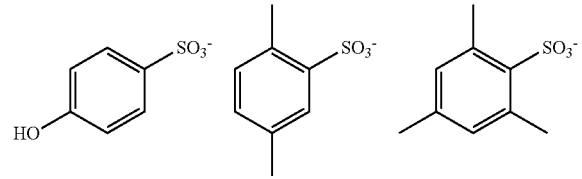
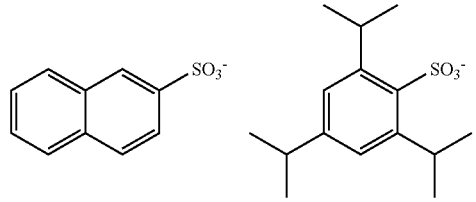
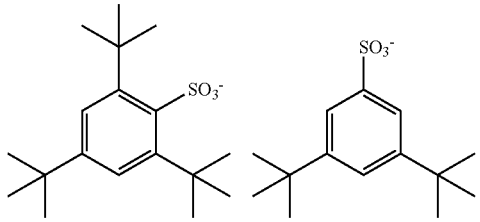
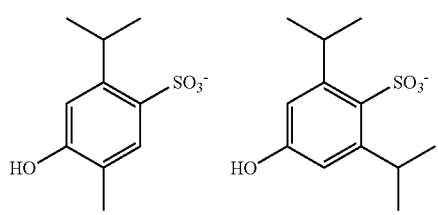
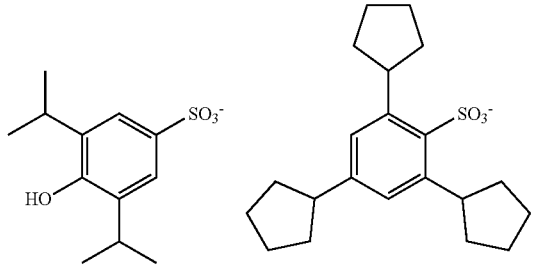
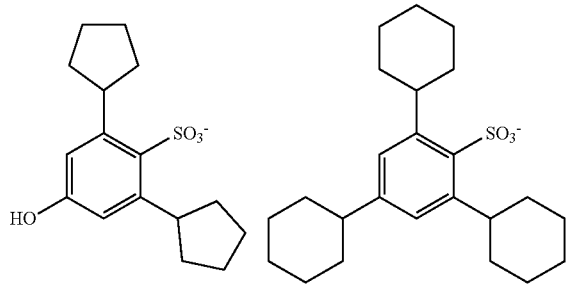
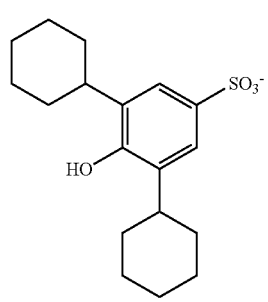
-continued
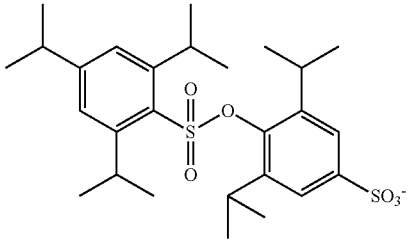
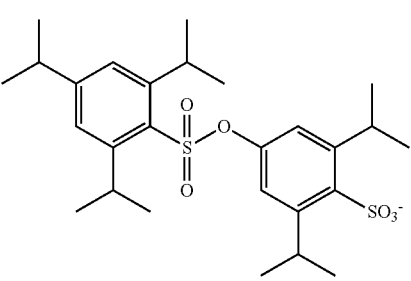
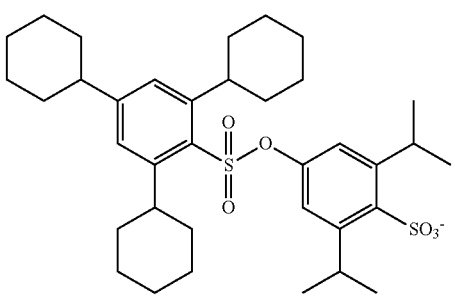
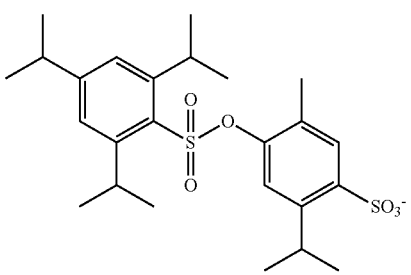
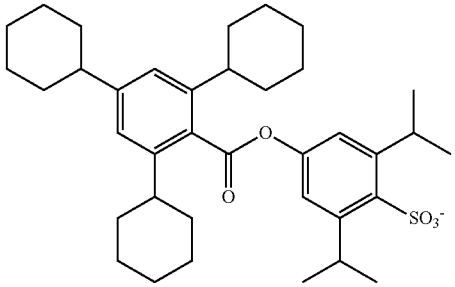
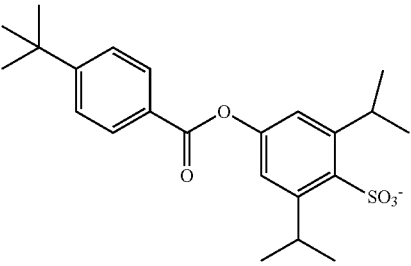

49
-continued
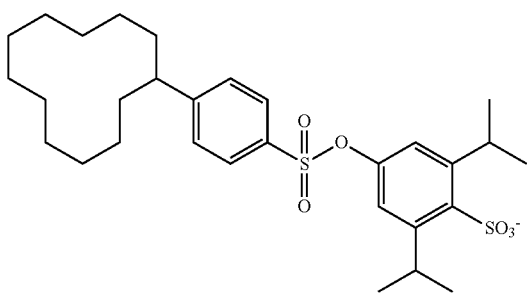
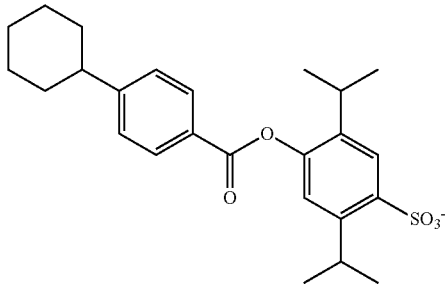
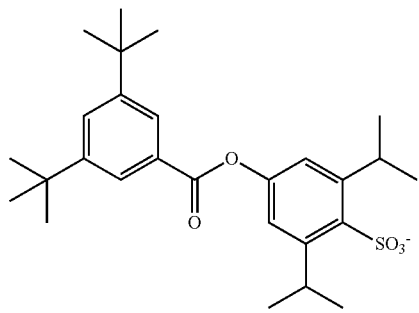
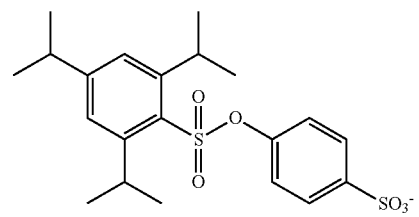
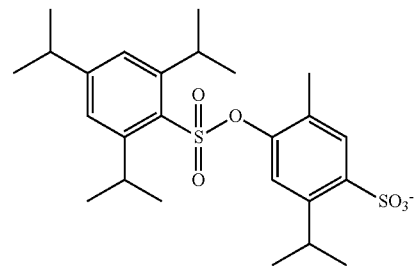
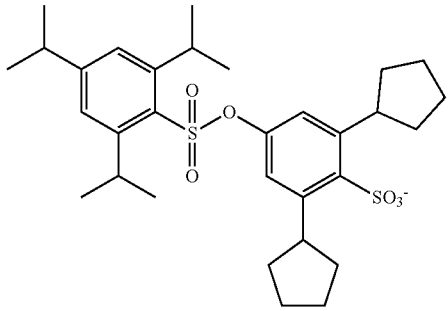
50
-continued
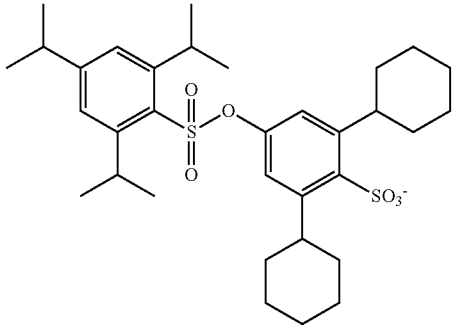
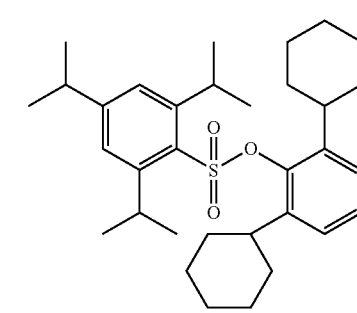
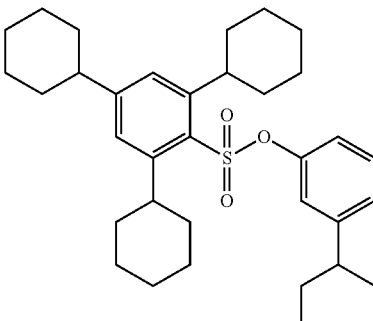
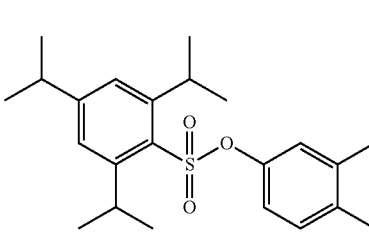
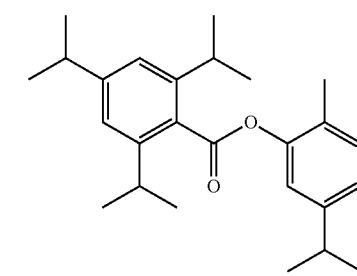

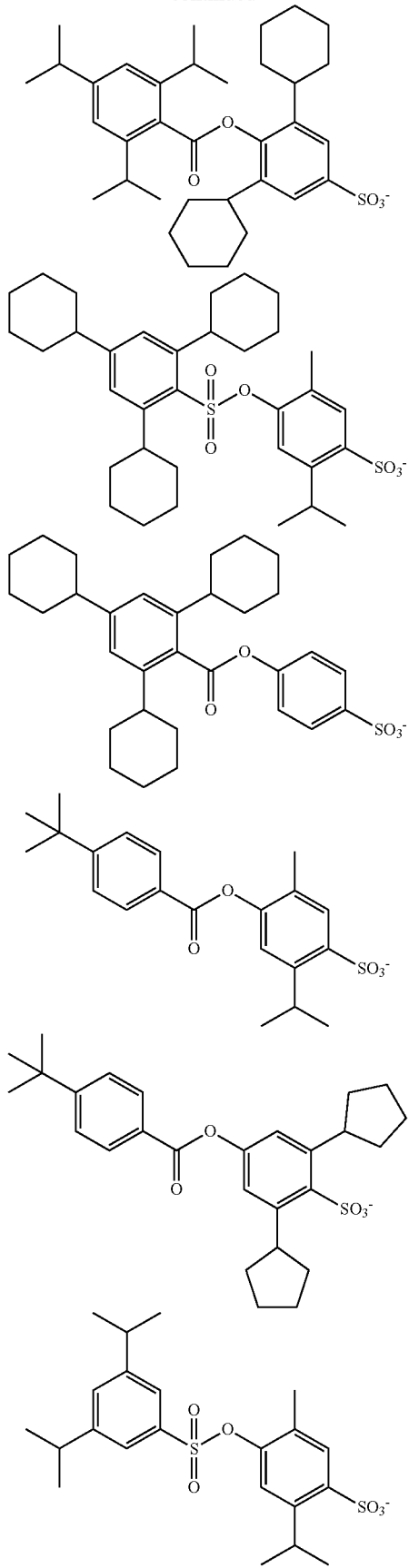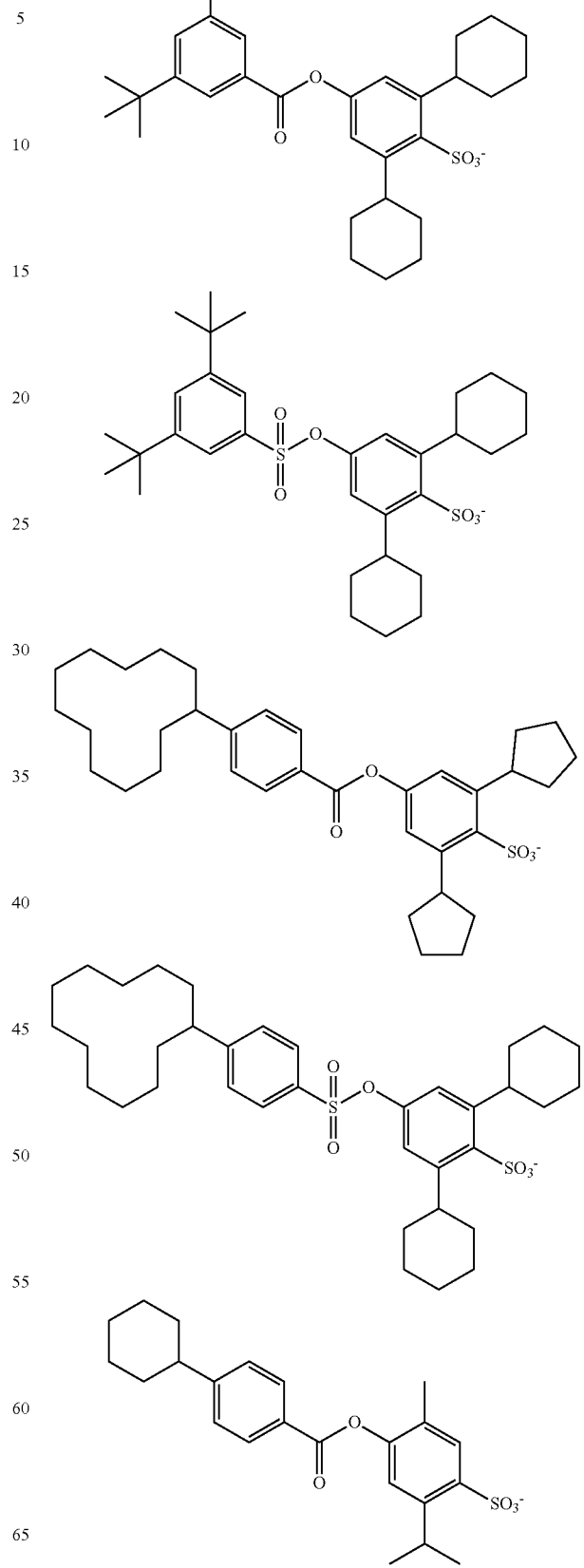

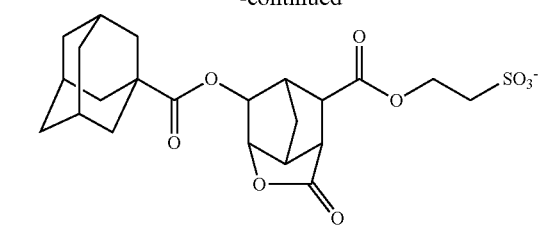
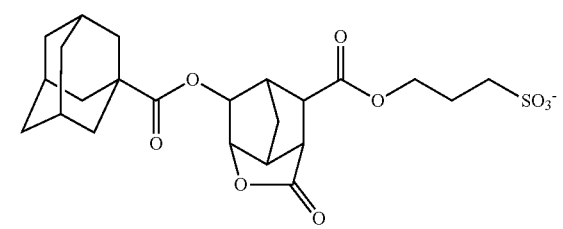
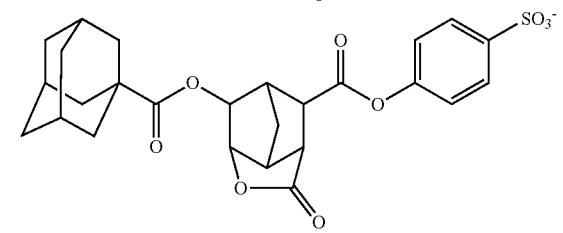
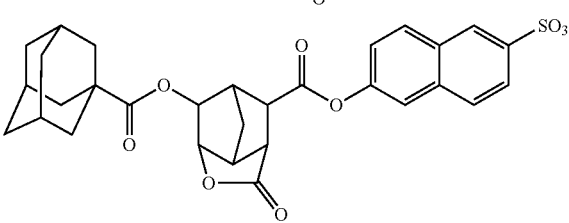
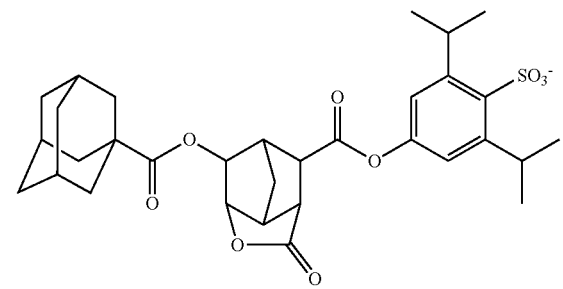
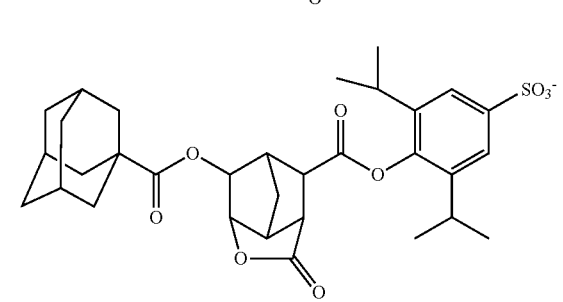
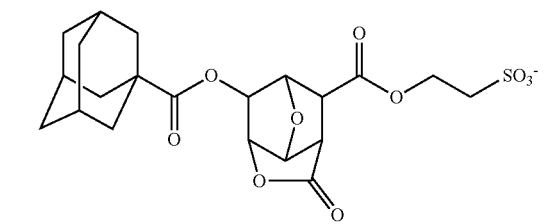
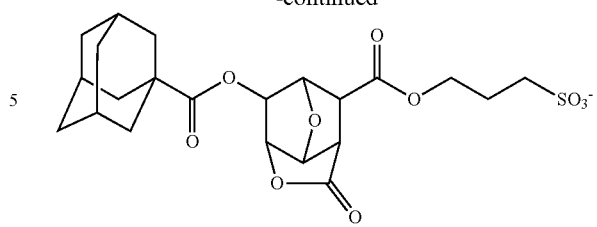
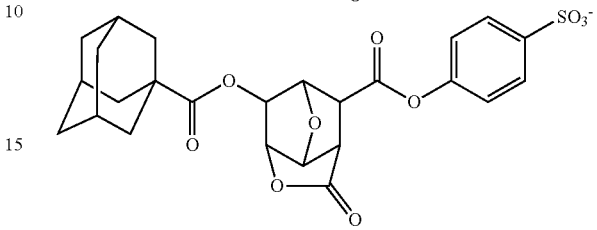
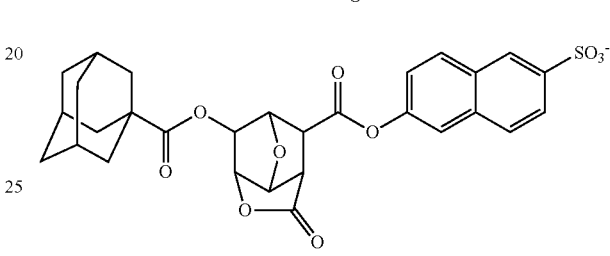
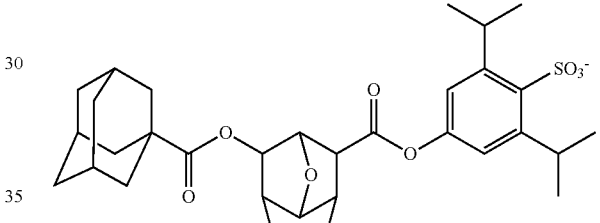
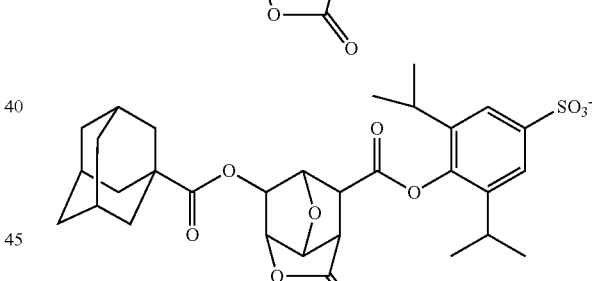
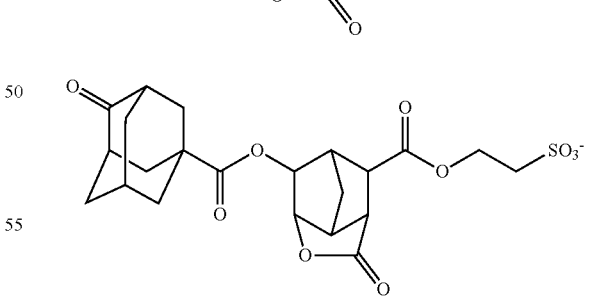
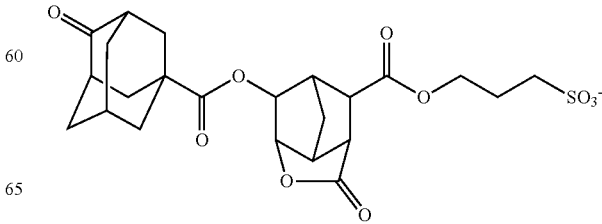

55
-continued
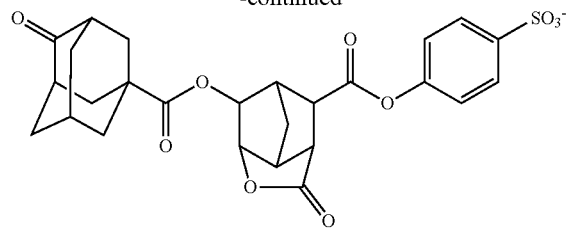
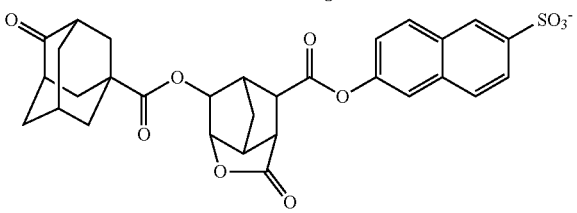
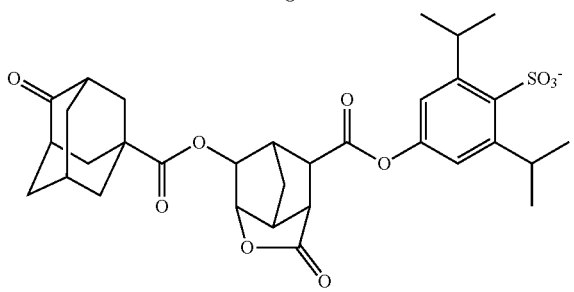
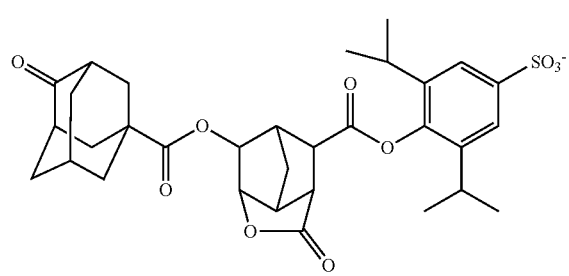
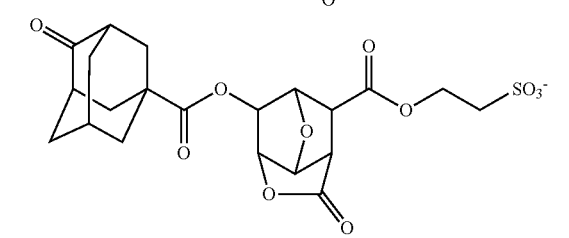
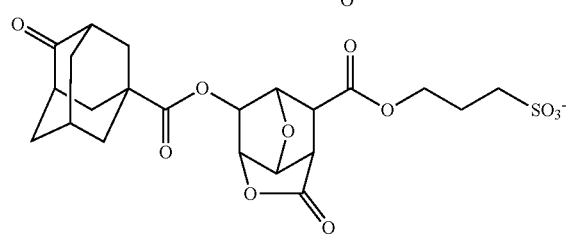
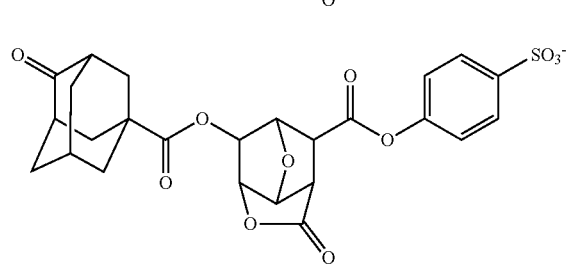
56
-continued
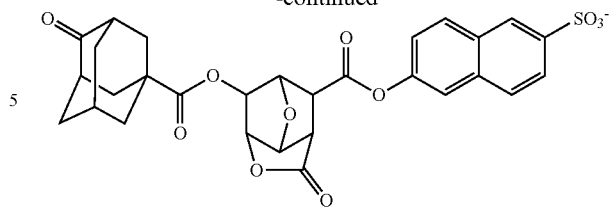
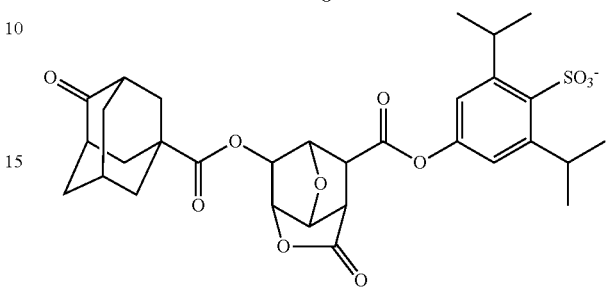
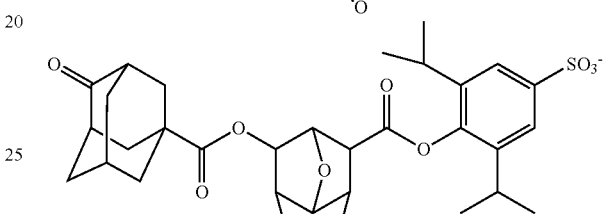
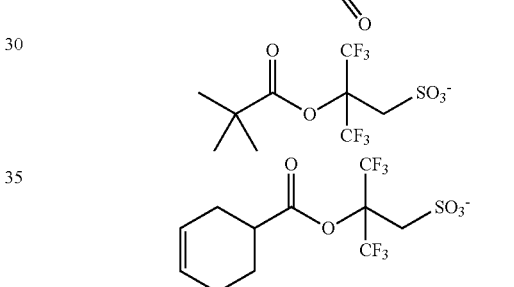
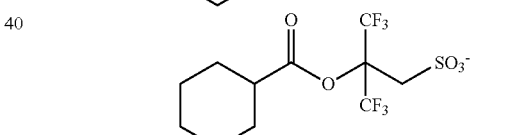
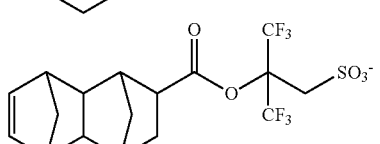
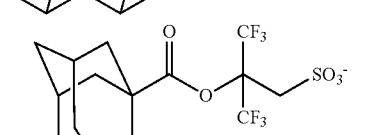
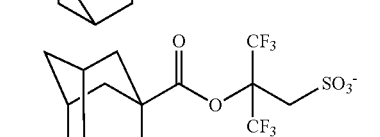
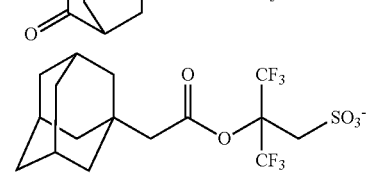

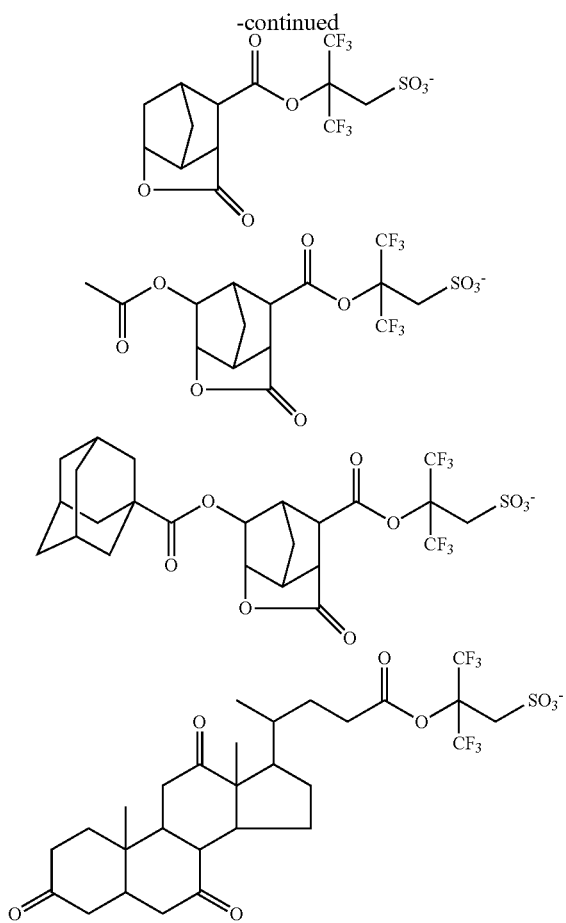

An appropriate amount of the PAG (E) used is 1 to 30 parts, more preferably 2 to 20 parts by weight per 100 parts by weight of the base polymer (B). Where the base polymer contains recurring units (B8) to (B11), the PAG may be omitted.

(F) Basic Compound

In the resist composition, (F) a basic compound may be added as the quencher other than component (A) for the purpose of correcting a pattern profile or the like. The basic compound is effective for controlling acid diffusion. Even when the resist film is applied to a processable substrate having an outermost surface layer made of a chromium-containing material, the basic compound is effective for minimizing the influence of the acid generated in the resist film on the chromium-containing material.

Numerous basic compounds are known useful including primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Examples are described in Patent Document 9, for example, and any such compounds are useful. Of the foregoing basic compounds, preferred are tris[2-(methoxymethoxy)ethyl]amine, tris[2-(methoxymethoxy)ethyl]amine-N-oxide, dibutylaminobenzoic acid, morpholine derivatives and imidazole derivatives.

An appropriate amount of the basic compound added is 0 to 10 parts, and more preferably 0 to 5 parts by weight per 100 parts by weight of the base polymer (B). The basic compounds may be used alone or in admixture.

(G) Surfactant

In the resist composition, any of surfactants commonly used for improving coating characteristics to the processable substrate may be added as an optional component. Numerous surfactants are known in the art, as described in JP-A 2004-115630, for example. A choice may be made with reference to such patent documents. An appropriate amount of the surfactant (G) used is 0 to 5 parts by weight per 100 parts by weight of the base polymer (B).

Process

A further embodiment of the invention is a resist pattern forming process comprising the steps of applying the resist composition defined above onto a substrate to form a resist film thereon, exposing the resist film pattern wise to high-energy radiation, and developing the resist film in an alkaline developer to form a resist pattern.

Pattern formation using the resist composition of the invention may be performed by well-known lithography processes. In general, the resist composition is first applied onto a processable substrate such as a substrate for IC fabrication (e.g., Si, SiO, $SiO_2$, SiN, SiON, TiN, WSi, BPSG, SOG, organic antireflective coating, etc.) or a substrate for mask circuit fabrication (e.g., Cr, CrO, CrON, $MoSi_2$, Si, SiO, $SiO_2$, etc.) by a suitable coating technique such as spin coating. The coating is prebaked on a hotplate at a temperature of 60 to 150° C. for 1 to 20 minutes, preferably at 80 to 140° C. for 1 to 10 minutes to form a resist film of 0.03 to 2 μm thick.

An anti-charging film comprising a conductive polymer may be formed on the resist film. The anti-charging film is effective for preventing a charging phenomenon or charge buildup in the resist film during EB writing for thereby achieving a significant improvement in writing position accuracy. The anti-charging film is typically formed of a conductive polymer such as polyaniline or polythiophene as described in JP-A 2016-200634.

Then the resist film is exposed pattern wise to high-energy radiation such as UV, deep-UV, excimer laser (KrF, ArF), EUV, x-ray, γ-ray or synchrotron radiation or EB. On use of UV, deep-UV, EUV, excimer laser, x-ray, γ-ray or synchrotron radiation as the high-energy radiation, the resist film is exposed through a mask having a desired pattern, preferably in a dose of 1 to 200 $mJ/cm^2$, more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$. The resist composition of the invention is especially effective in the EUV or EB lithography.

The exposure may be performed by conventional lithography whereas the immersion lithography of holding a liquid between the mask and the resist film may be employed if desired. In the case of immersion lithography, a protective film which is insoluble in water may be used.

The resist film is then baked (PEB) on a hotplate at 60 to 150° C. for 1 to 20 minutes, preferably at 80 to 140° C. for 1 to 10 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

From the resist composition, a pattern with a high resolution and minimal LER may be formed. The resist composition is effectively applicable to a substrate, specifically a substrate having a surface layer of material to which a resist film is less adherent and which is likely to invite pattern stripping or pattern collapse, and particularly a substrate having sputter deposited thereon metallic chromium or a chromium compound containing at least one light element selected from oxygen, nitrogen and carbon or a substrate having an outermost surface layer of $SiO_x$. The invention is especially effective for pattern formation on a photomask blank as the substrate.

Even on use of a substrate having an outermost surface layer made of a chromium or silicon-containing material which tends to adversely affect the profile of resist pattern, typically photomask blank, the resist pattern forming process is successful in forming a pattern with a high resolution and reduced LER via exposure to high-energy radiation because the resist composition is effective for controlling acid diffusion at the substrate interface.

EXAMPLE

Examples of the invention are given below by way of illustration and not by way of limitation. The abbreviation "pbw" is parts by weight. THF is tetrahydrofuran. The copolymer composition is expressed by a molar ratio. Mw is measured by GPC versus polystyrene standards. Analytic instruments are as shown below.
IR: NICOLET 6700 by Thermo Fisher Scientific Inc.
$^1$H-NMR: ECA-500 by JEOL Ltd.
LC-MS: ACQUITY UPLC H-Class system and ACQUITY QDa by Waters.
[1] Synthesis of Sulfonium Compounds Example 1-1

Synthesis of N-2-(diphenylsulfonio)phenylmesylamidate Q-1

Example 1-1-1

Synthesis of N-2-phenylthiophenylmesylamide (Intermediate A)

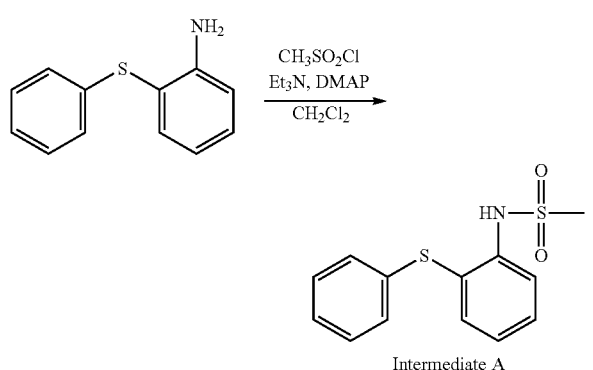

In 2,500 g of methylene chloride were dissolved 500.0 g of 2-aminophenyl phenyl sulfide, 301.4 g of triethylamine, and 60.6 g of 4-dimethylaminopyridine. Under ice cooling, 340.9 g of methanesulfonyl chloride was added dropwise to the solution, which was aged at room temperature for 18 hours. After aging, 905 g of 20 wt % HCl aqueous solution was added to quench the reaction. The organic layer was taken out, washed 3 times with 1,000 g of water, and concentrated in vacuum. Hexane was added to the residue for recrystallization. The resulting crystal was recovered and dried in vacuum, obtaining 589.9 g (yield 85%) of N-2-phenylthiophenylmethanesulfonamide (Intermediate A).

Example 1-1-2

Synthesis of N-2-(diphenylsulfonio)phenylmesylamide mesylate (Intermediate B)

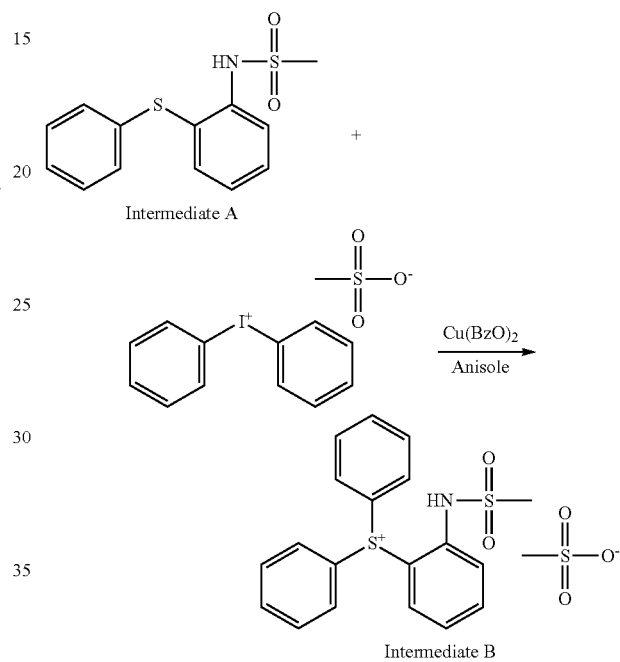

To 300.0 g of Intermediate A, 420.0 g of diphenyliodonium mesylate, 0.65 g of copper(II) benzoate, and 1,500 g of anisole were added, followed by stirring at 90° C. for 3 hours. Hexane, 3,000 g, was added to the solution for recrystallization. The resulting crystal was recovered, obtaining the desired compound, N-2-(diphenylsulfonio)phenylmesylamide mesylate (Intermediate B). Intermediate B was fed to the next step without isolation.

Example 1-1-3

Synthesis of N-2-(diphenylsulfonio)phenylmesylamidate (Q-1)

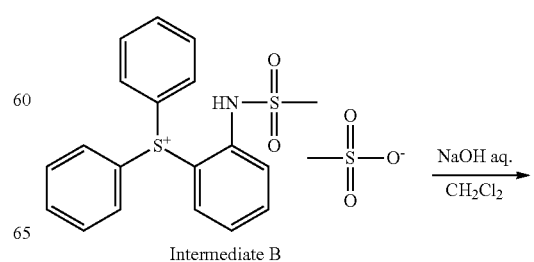

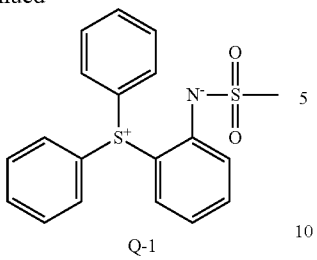

Q-1

The entire amount of Intermediate B was dissolved in 600 g of methylene chloride. To the solution, 342.4 g of 25 wt % sodium hydroxide aqueous solution and 300 g of deionized water were added and stirred for 30 minutes. At the end of stirring, the organic layer was taken out, washed with water, and concentrated under reduced pressure. After 60 g of methyl isobutyl ketone was added to the concentrate, water was removed by azeotropic distillation. To the residue, 900 g of diisopropyl ether and 900 g of tert-butyl methyl ether were added for recrystallization. The resulting crystal was recovered and dried in vacuum, obtaining the target compound, N-2-(diphenylsulfonio)phenylmesylamidate (Q-1). Amount 158.2 g, yield 42% from Intermediate A.

The target compound was analyzed by spectroscopy. The NMR spectrum, $^1$H-NMR in DMSO-$d_6$ is shown in FIG. 1. In $^1$H-NMR analysis, minute amounts of residual solvents (tert-butyl methyl ether, methyl isobutyl ketone) and water were observed.

IR (D-ATR):
ν=3110, 1750, 1531, 1365, 1333, 1298, 1285, 987, 950, 900, 720, 688, 522 cm$^{-1}$
LC-MS: Positive [M+H]$^+$ 356 (corresponding to $C_{19}H_{18}NO_2S_2^+$)

Example 1-2

Synthesis of N-2-(diphenylsulfonio)phenyltosylamidate Q-2

Example 1-2-1

Synthesis of N-2-phenylthiophenyltosylamide (Intermediate C)

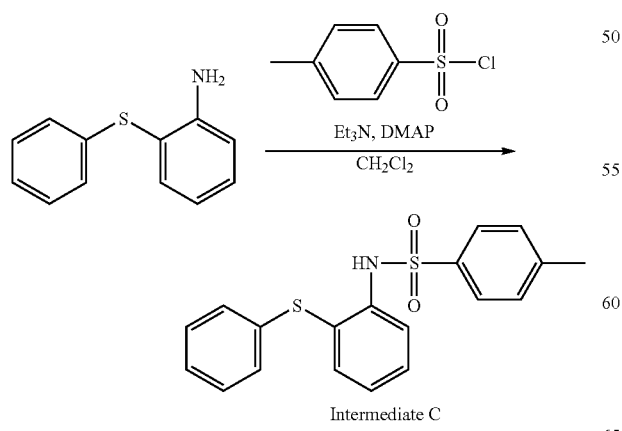

Intermediate C

By following the same procedure as in Example 1-1-1 aside from using p-toluenesulfonyl chloride instead of meth-anesulfonyl chloride, N-2-phenylthiophenyltosylamide (Intermediate C) was obtained. Amount 722.9 g, yield 82%.

Example 1-2-2

Synthesis of N-2-(diphenylsulfonio)phenyltosylamide mesylate (Intermediate D)

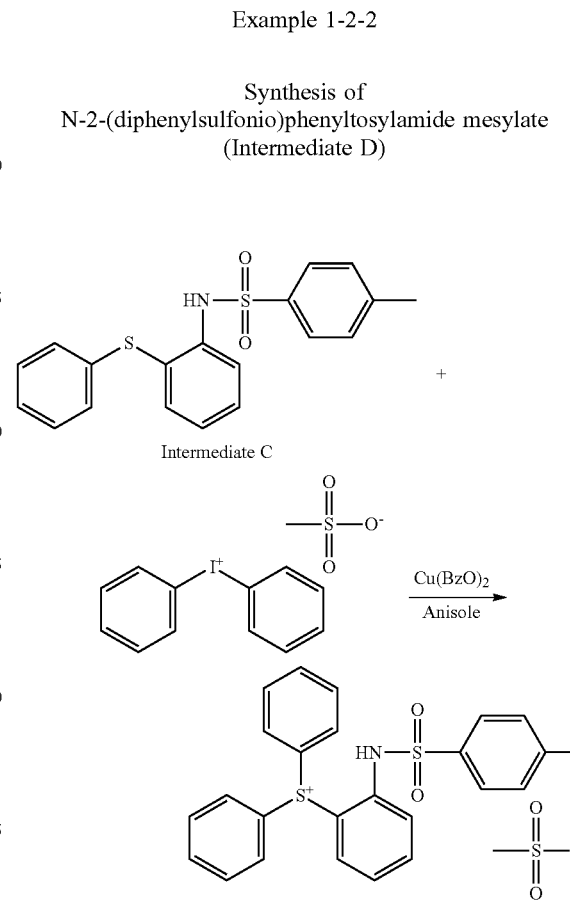

Intermediate D

By following the same procedure as in Example 1-1-2 aside from using 300 g of Intermediate C instead of Intermediate A, N-2-(diphenylsulfonio)phenyltosylamide mesylate (Intermediate D) was obtained. Intermediate D was fed to the next step without isolation.

Example 1-2-3

Synthesis of N-2-(diphenylsulfonio)phenyltosylamidate (Q-2)

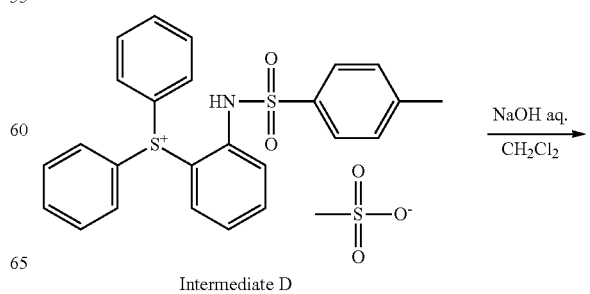

Intermediate D

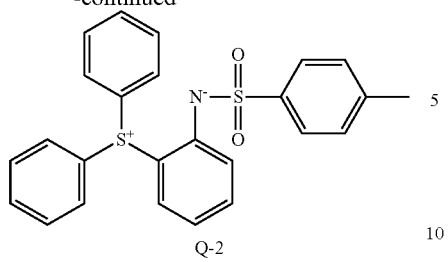

Q-2

By following the same procedure as in Example 1-1-3 aside from using Intermediate D instead of Intermediate B, N-2-(diphenylsulfonio)phenyltosylamidate (Q-2) was obtained. Amount 180.6 g, yield 51%.

Figure 2:
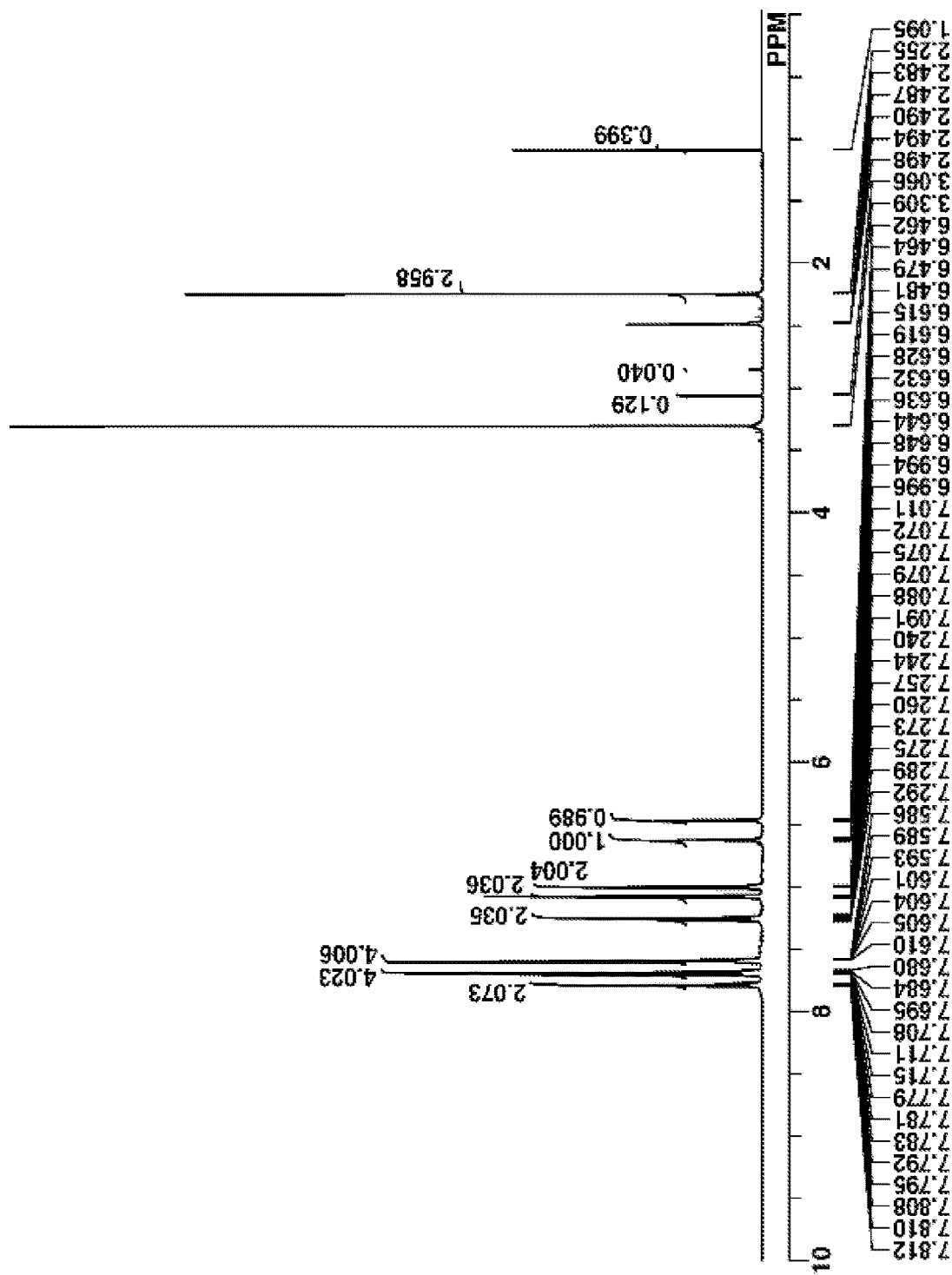
FIG. 2 is a diagram showing $^1$H-NMR spectrum of Compound Q-2 in Example 1-2-3.

The target compound was analyzed by spectroscopy. The NMR spectrum, $^1$H-NMR in DMSO-$d_6$ is shown in FIG. 2. In $^1$H-NMR analysis, minute amounts of residual solvents (tert-butyl methyl ether, methyl isobutyl ketone) and water were observed.

IR (D-ATR):

v=2885, 1780, 1543, 1432, 1390, 1357, 1128, 1009, 987, 841, 821, 776, 678 cm$^{-1}$

LC-MS: Positive [M+H]$^+$ 432 (corresponding to $C_{25}H_{21}NO_2S_2{}^+$)

Example 1-3

Synthesis of N-2-(diphenylsulfonio)phenyl-2-fluorobenzenesulfonylamidate Q-3

Example 1-3-1

Synthesis of N-2-phenylthiophenyl-2-fluorobenzenesulfonylamide (Intermediate E)

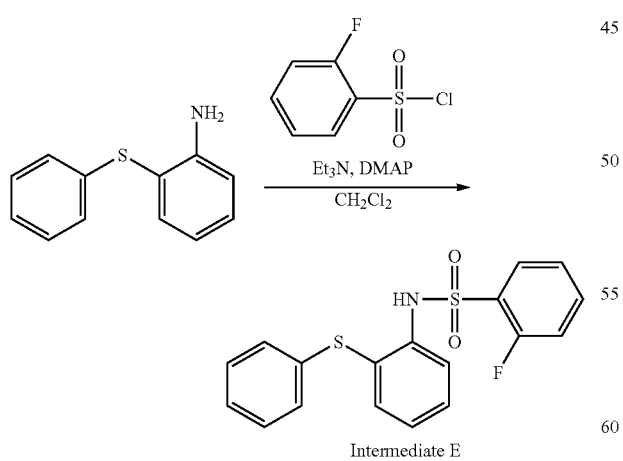

Intermediate E

By following the same procedure as in Example 1-1-1 aside from using 2-fluorobenzenesulfonyl chloride instead of methanesulfonyl chloride, N-2-phenylthiophenyl-2-fluorobenzenesulfonylamide (Intermediate E) was obtained. Amount 722.9 g, yield 82%.

Example 1-3-2

Synthesis of N-2-(diphenylsulfonio)phenyl-2-fluorobenzenesulfonylamide mesylate (Intermediate F)

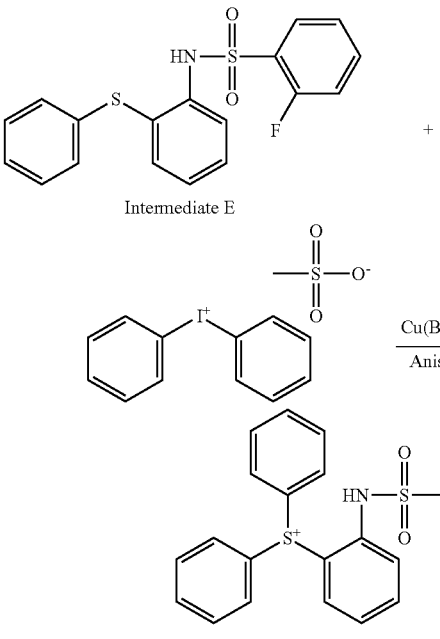

Intermediate F

By following the same procedure as in Example 1-1-2 aside from using 300 g of Intermediate E instead of Intermediate A, N-2-(diphenylsulfonio)phenyl-2-fluorobenzenesulfonylamide mesylate (Intermediate F) was obtained. Intermediate F was fed to the next step without isolation.

Example 1-3-3

Synthesis of N-2-(diphenylsulfonio)phenyl-2-fluorobenzenesulfonylamidate (Q-3)

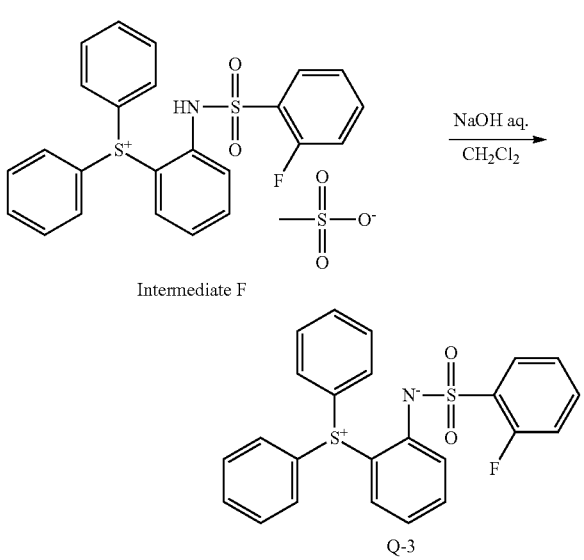

Q-3

By following the same procedure as in Example 1-1-3 aside from using Intermediate F instead of Intermediate B, N-2-(diphenylsulfonio)phenyl-2-fluorobenzenesulfonylamidate (Q-3) was obtained. Amount 174.5 g, yield 48%.

Figure 3:
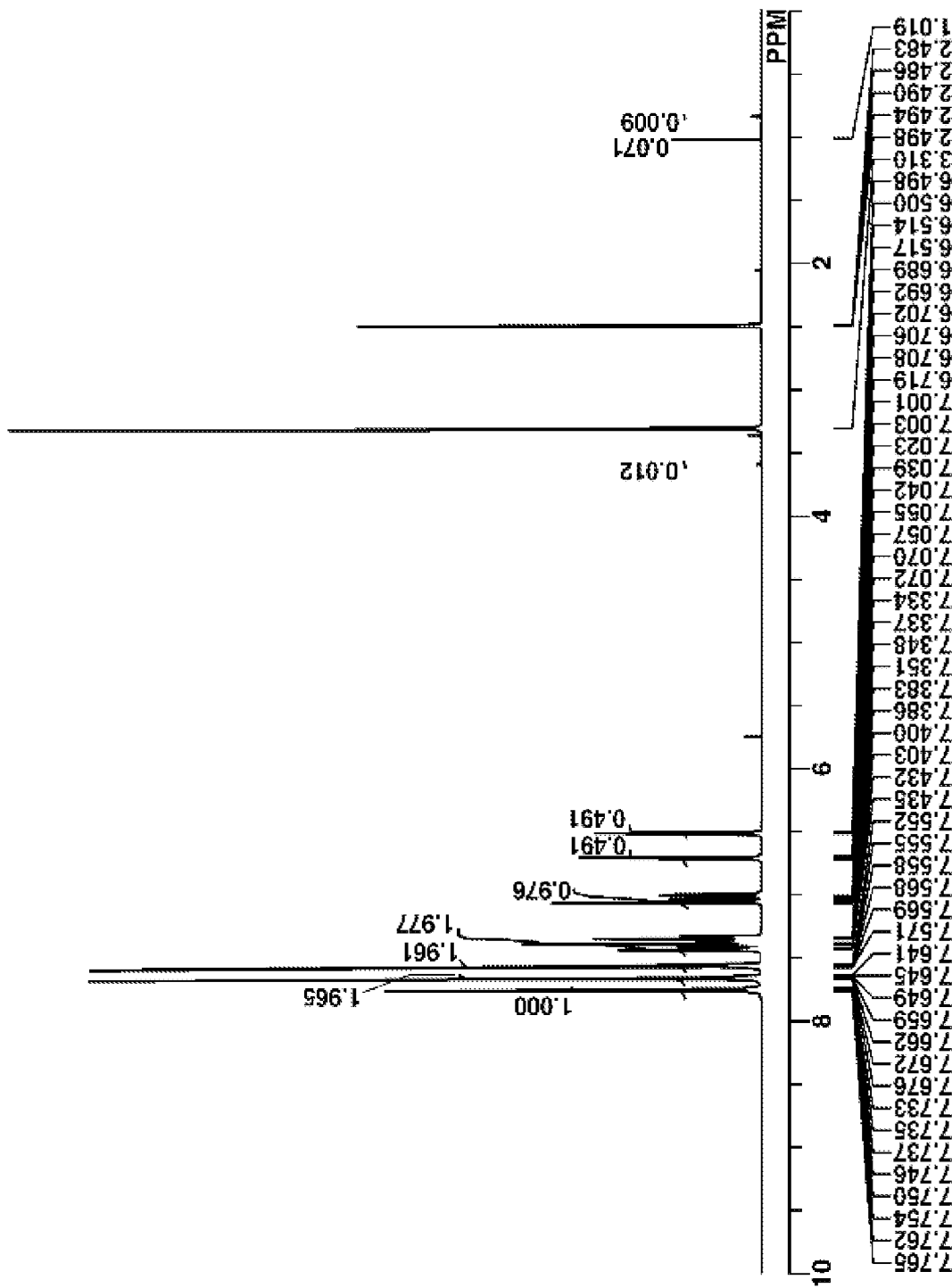
FIG. 3 is a diagram showing $^1$H-NMR spectrum of Compound Q-3 in Example 1-3-3.

The target compound was analyzed by spectroscopy. The NMR spectrum, $^1$H-NMR in DMSO-$d_6$ is shown in FIG. 3. In $^1$H-NMR analysis, minute amounts of residual solvents (tert-butyl methyl ether, methyl isobutyl ketone) and water were observed.

IR (D-ATR):
ν=3050, 1876, 1565, 1552, 1433, 1380, 1145, 1009, 987, 840, 769, 712, 489 cm$^{-1}$

LC-MS: Positive $[M+H]^+$ 435 (corresponding to $C_{24}H_{18}FNO_2S_2^+$)

[2] Synthesis of Polymers

Synthesis Example 1-1

Synthesis of Polymer A1

A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen flow were repeated three times. The reactor was warmed up to room temperature, whereupon 34.7 g of 2,2'-azobis(2,4-dimethylvaleronitrile) (V-65 by Wako Pure Chemical Industries, Ltd.) was added as polymerization initiator. The reactor was heated at 55° C., whereupon reaction ran for 40 hours. With stirring, a mixture of 970 g of methanol and 180 g of water was added dropwise to the reaction solution. The solution separated into two layers during 30 minutes of standing. The lower layer (polymer layer) was concentrated under reduced pressure. The polymer layer concentrate was dissolved again in 0.45 L of methanol and 0.54 L of THF, to which 160 g of triethylamine and 30 g of water were added. The mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. The solution separated into two layers during 30 minutes of standing. To the lower layer (polymer layer) was added 300 g of THF. With stirring, 1,030 g of hexane was added dropwise thereto. After 30 minutes of standing, the lower layer (polymer layer) was concentrated under reduced pressure. The polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. On analysis by $^1$H-NMR and GPC, the polymer had a copolymer compositional ratio of hydroxystyrene: acenaphthylene=89.3:10.7, Mw=5,000, and Mw/Mn=1.63.

Under acidic conditions, 100 g of the polymer was reacted with 50 g of 2-methyl-1-propenyl methyl ether. This was followed by neutralization, phase separation, and crystallization, obtaining 125 g of a polymer, designated Polymer A1.

Synthesis Examples 1-2 to 1-9

Synthesis of Polymers A2 to A7 and Polymers P1 to P2

Polymers A2 to A7 and Polymers P1 to P2 were synthesized as in Synthesis Example 1-1 aside from changing the monomers and reagents.

Polymers A1 to A7 and Polymers P1 to P2 had the following structures.

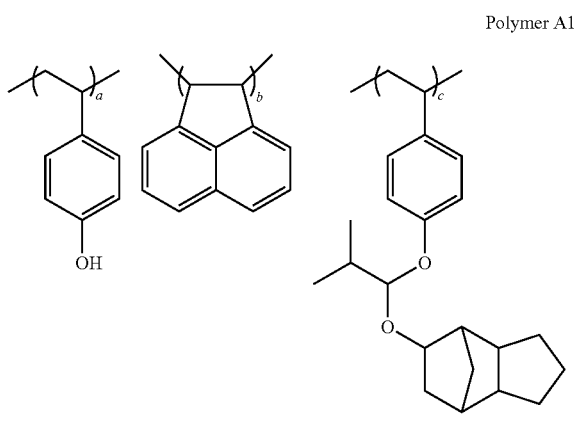

(a = 0.76, b = 0.12, c = 0.12, Mw = 5,500)

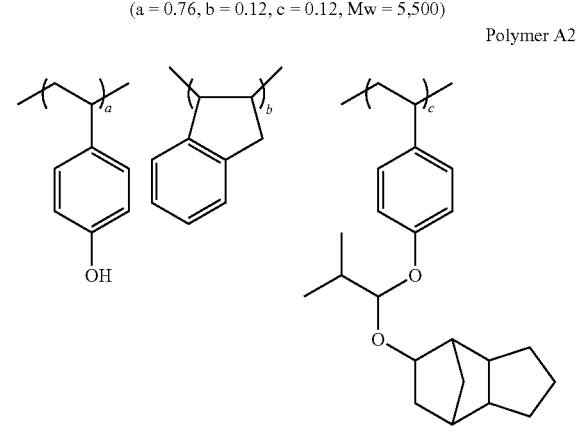

(a = 0.76, b = 0.11, c = 0.13, Mw = 5,800)

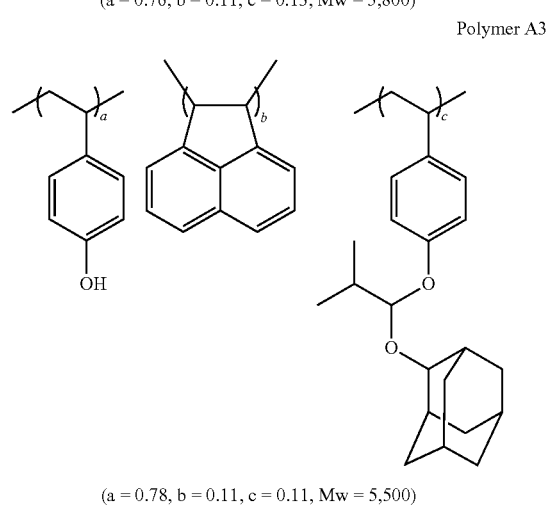

(a = 0.78, b = 0.11, c = 0.11, Mw = 5,500)

Polymer A4
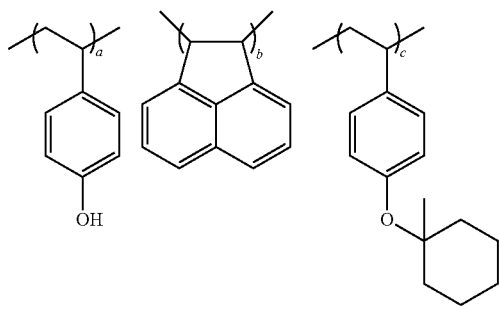
(a = 0.69, b = 0.10, c = 0.21, Mw = 4,000)
Polymer A5
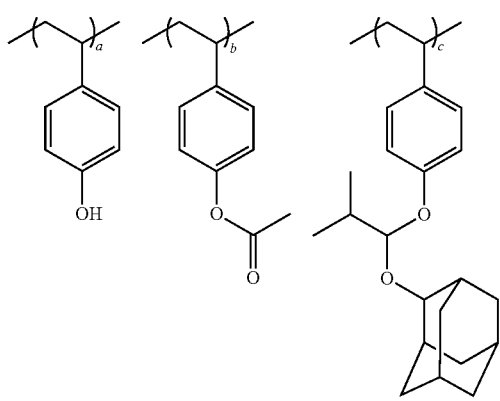
(a = 0.73, b = 0.12, c = 0.15, Mw = 5,700)
Polymer A6
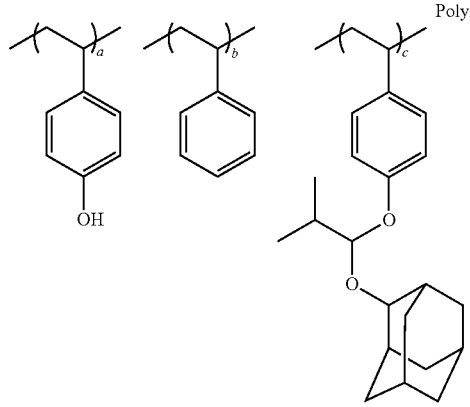
(a = 0.73, b = 0.13, c = 0.14, Mw = 5,400)
Polymer A7
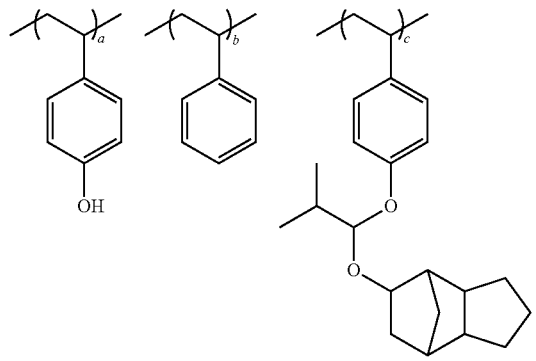
(a = 0.73, b = 0.13, c = 0.14, Mw = 5,400)
Polymer P1
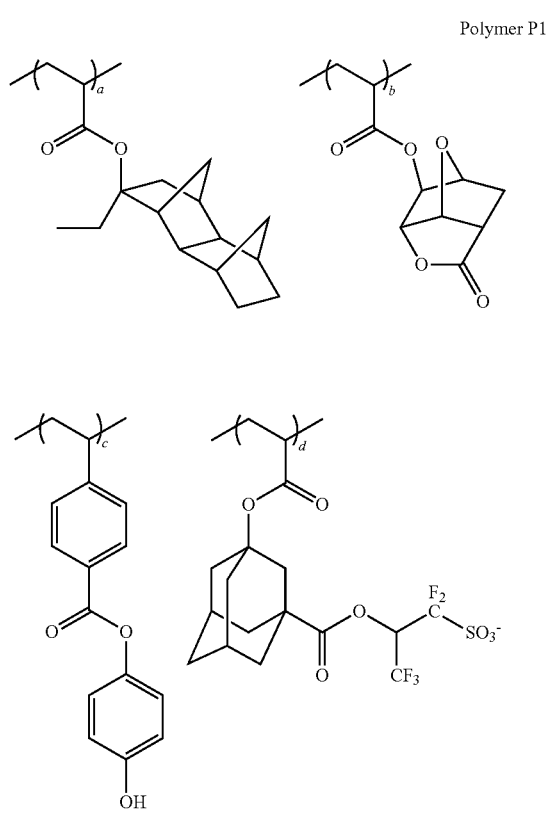
(a = 0.30, b = 0.30, c = 0.20, d = 0.20, Mw = 14,500)

Polymer P2

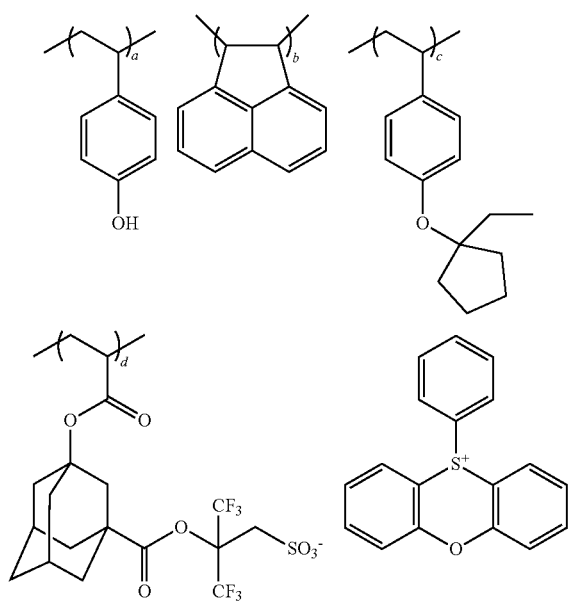

(a = 0.55, b = 0.10, c = 0.25, d = 0.10 Mw = 7,200)

[3] Preparation of Positive Resist Compositions

Examples 2-1 to 2-38 and Comparative Examples 1-1 to 1-6

The quencher is selected from sulfonium compounds Q-1 to Q-3 synthesized in Examples and comparative quenchers Q-4 to Q-6; the base polymer is from Polymers A1 to A7 and Polymers P1 to P2; the photoacid generator is from PAG-A to PAG-C; and the additive is from fluorinated polymers, i.e., Polymers C1 to C3. A positive resist composition in solution form was prepared by dissolving the components in an organic solvent according to the formulation shown in Tables 1 to 3, and filtering through a UPE filter with a pore size of 0.02 m. The organic solvents in Tables 1 to 3 are PGMEA (propylene glycol monomethyl ether acetate), EL (ethyl lactate), PGME (propylene glycol monomethyl ether), and CyH (cyclohexanone). In each composition, 0.075 pbw of surfactant PF-636 (Omnova Solutions) was added per 100 pbw of solids.

Notably, Q-4 to Q-6, PAG-A to PAG-C, and Polymers C1 to C3 are identified below.

Q-4

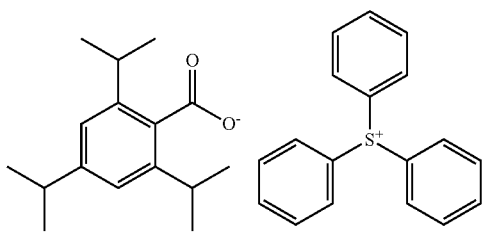

Q-5

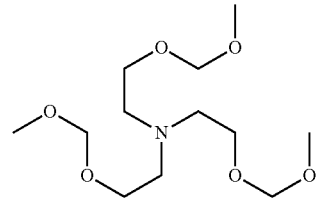

6

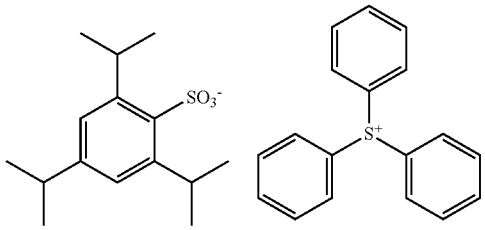

PAG-A

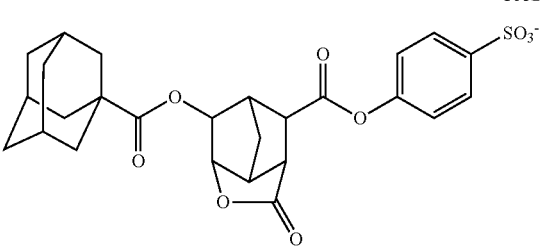

PAG-B

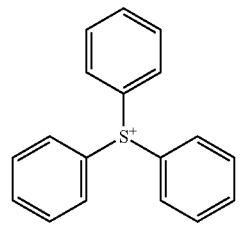

PAG-C

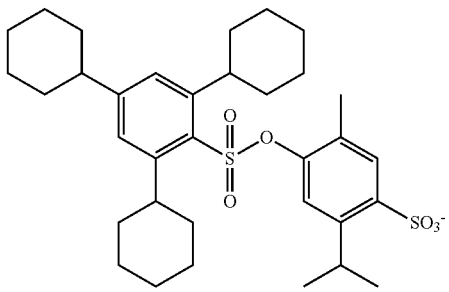

-continued

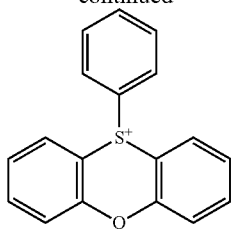

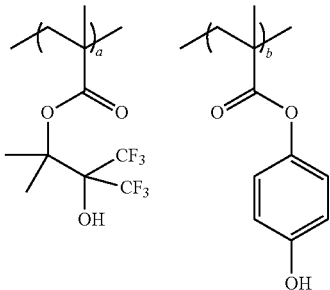

Polymer C1

(a = 0.80, b = 0.20, Mw = 6,000)

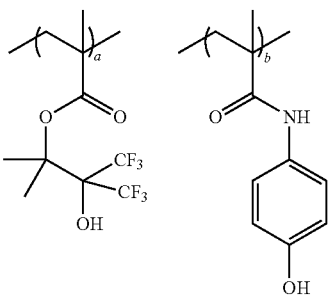

Polymer C2

(a = 0.80, b = 0.20, Mw = 6,400)

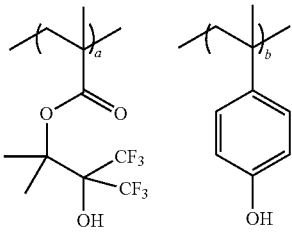

Polymer C3

(a = 0.80, b = 0.20, Mw = 6,400)

TABLE 1

|  | Resist composition | Quencher (pbw) | Resin 1 (pbw) | Resin 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|
| Example 2-1 | R-1 | Q-1 (3.0) | Polymer A1 (80) |  | PAG-A (9) |  | PGMEA (1,160) | EL (2,706) |  |
| 2-2 | R-2 | Q-1 (3.0) | Polymer A1 (80) |  | PAG-B (9) |  | PGMEA (1,160) | EL (2,706) |  |
| 2-3 | R-3 | Q-1 (3.0) | Polymer A1 (80) |  | PAG-C (9) |  | PGMEA (1,160) | EL 2,706 |  |
| 2-4 | R-4 | Q-2 (3.0) | Polymer A1 (80) |  | PAG-C (9) |  | PGMEA (1,160) | EL (2,706) |  |
| 2-5 | R-5 | Q-3 (3.0) | Polymer A1 (80) |  | PAG-C (9) |  | PGMEA (1,160) | EL (2,706) |  |
| 2-6 | R-6 | Q-1 (3.0) | Polymer A1 (80) |  | PAG-C (9) | Polymer C1 (3) | PGMEA (1,160) | EL (2,706) |  |
| 2-7 | R-7 | Q-1 (3.0) | Polymer A1 (80) |  | PAG-C (9) | Polymer C2 (3) | PGMEA (1,160) | EL (2,706) |  |
| 2-8 | R-8 | Q-1 (3.0) | Polymer A1 (80) |  | PAG-C (9) | Polymer C3 (3) | PGMEA (1,160) | EL (2,706) |  |
| 2-9 | R-9 | Q-1 (3.8) | Polymer A1 (80) |  | PAG-C (18) |  | PGMEA (1,160) | EL (2,706) |  |
| 2-10 | R-10 | Q-1 (3.0) | Polymer A2 (80) |  | PAG-C (9) |  | PGMEA (1,160) | EL (2,706) |  |
| 2-11 | R-11 | Q-1 (3.0) | Polymer A3 (80) |  | PAG-C (9) |  | PGMEA (1,160) | EL (2,706) |  |
| 2-12 | R-12 | Q-2 (3.0) | Polymer A3 (80) |  | PAG-C (9) |  | PGMEA (1,160) | EL (2,706) |  |
| 2-13 | R-13 | Q-3 (3.0) | Polymer A3 (80) |  | PAG-C (9) |  | PGMEA (1,160) | EL (2,706) |  |
| 2-14 | R-14 | Q-1 (3.0) | Polymer A3 (80) |  | PAG-C (9) | Polymer C1 (3) | PGMEA (1,160) | EL (2,706) |  |
| 2-15 | R-15 | Q-1 (2.8) | Polymer A3 (40) | Polymer P1 (40) |  |  | PGMEA (1,160) | CyH (2,706) |  |
| 2-16 | R-16 | Q-1 (2.8) | Polymer A3 (40) | Polymer P2 (40) |  |  | PGMEA (386) | EL (1,932) | PGME (1,546) |
| 2-17 | R-17 | Q-1 (2.8) | Polymer A3 (40) | Polymer P2 (40) |  |  | PGMEA (386) | EL (1,932) | PGME (1,546) |
| 2-18 | R-18 | Q-1 (3.2) | Polymer A3 (40) | Polymer P2 (40) | PAG-A (5) |  | PGMEA (386) | EL (1,932) | PGME (1,546) |
| 2-19 | R-19 | Q-1 (3.2) | Polymer A3 (40) | Polymer P2 (40) | PAG-A (5) | Polymer C1 (3) | PGMEA (386) | EL (1,932) | PGME (1,546) |
| 2-20 | R-20 | Q-1 (3.2) | Polymer A3 (40) | Polymer P2 (40) | PAG-C (5) | Polymer C1 (3) | PGMEA (386) | EL (1,932) | PGME (1,546) |

TABLE 2

| | Resist composition | Quencher (pbw) | Resin 1 (pbw) | Resin 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|
| Example 2-21 | R-21 | Q-1 (3.0) | Polymer A4 (80) | | PAG-C (9) | | PGMEA (1,160) | EL (2,706) | |
| 2-22 | R-22 | Q-1 (2.8) | Polymer A4 (40) | Polymer P2 (40) | | | PGMEA (386) | EL (1,932) | PGME (1,546) |
| 2-23 | R-23 | Q-1 (3.2) | Polymer A4 (40) | Polymer P2 (40) | PAG-A (5) | | PGMEA (386) | EL (1,932) | PGME (1,546) |
| 2-24 | R-24 | Q-1 (3.2) | Polymer A4 (40) | Polymer P2 (40) | PAG-A (5) | Polymer C1 (3) | PGMEA (255) | EL (1,640) | PGME (1,310) |
| 2-25 | R-25 | Q-1 (3.2) | Polymer A4 (40) | Polymer P2 (40) | PAG-C (5) | Polymer C1 (3) | PGMEA (255) | EL (1,640) | PGME (1,310) |
| 2-26 | R-26 | Q-1 (3.0) | Polymer A5 (80) | | PAG-C (9) | | PGMEA (1,160) | EL (2,706) | |
| 2-27 | R-27 | Q-1 (3.0) | Polymer A5 (80) | | PAG-C (18) | | PGMEA (1,160) | EL (2,706) | |
| 2-28 | R-28 | Q-1 (3.0) | Polymer A6 (80) | | PAG-C (9) | | PGMEA (1,160) | EL (2,706) | |
| 2-29 | R-29 | Q-1 (3.8) | Polymer A6 (80) | | PAG-C (18) | | PGMEA (1,160) | EL (2,706) | |
| 2-30 | R-30 | Q-1 (3.0) | Polymer A7 (80) | | PAG-C (9) | | PGMEA (1,160) | EL (2,706) | |
| 2-31 | R-31 | Q-2 (3.0) | Polymer A7 (80) | | PAG-C (9) | | PGMEA (1,160) | EL (2,706) | |
| 2-32 | R-32 | Q-3 (3.0) | Polymer A7 (80) | | PAG-C (9) | | PGMEA (1,160) | EL (2,706) | |
| 2-33 | R-33 | Q-1 (3.8) | Polymer A7 (80) | | PAG-C (18) | | PGMEA (1,160) | EL (2,706) | |
| 2-34 | R-34 | Q-1 (2.8) | Polymer A7 (40) | Polymer P2 (40) | | | PGMEA (255) | EL (1,640) | PGME (1,310) |
| 2-35 | R-35 | Q-1 (2.8) | Polymer A7 (40) | Polymer P2 (40) | | Polymer C1 (3) | PGMEA (255) | EL (1,640) | PGME (1,310) |
| 2-36 | R-36 | Q-1 (3.2) | Polymer A7 (40) | Polymer P2 (40) | PAG-A (5) | | PGMEA (255) | EL (1,640) | PGME (1,310) |
| 2-37 | R-37 | Q-1 (3.2) | Polymer A7 (40) | Polymer P2 (40) | PAG-A (5) | Polymer C1 (3) | PGMEA (255) | EL (1,640) | PGME (1,310) |
| 2-38 | R-38 | Q-1 (3.2) | Polymer A7 (40) | Polymer P2 (40) | PAG-C (5) | Polymer C1 (3) | PGMEA (255) | EL (1,640) | PGME (1,310) |

TABLE 3

| | Resist composition | Quencher (pbw) | Resin 1 (pbw) | Resin 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|
| Comparative Example 1-1 | CR-1 | Q-4 (4.0) | Polymer A1 (80) | | PAG-A (9) | | PGMEA (1,160) | EL (2,706) | |
| 1-2 | CR-2 | Q-5 (2.0) | Polymer A1 (80) | | PAG-A (9) | | PGMEA (1,160) | EL (2,706) | |
| 1-3 | CR-3 | Q-6 (3.0) | Polymer A1 (80) | | PAG-A (9) | | PGMEA (1,160) | EL (2,706) | |
| 1-4 | CR-4 | Q-6 (3.0) | Polymer A1 (80) | | PAG-A (9) | Polymer C1 (3) | PGMEA (1,160) | EL (2,706) | |
| 1-5 | CR-5 | Q-6 (3.0) | Polymer A1 (80) | | PAG-A (9) | Polymer C2 (3) | PGMEA (1,160) | EL (2,706) | |
| 1-6 | CR-6 | Q-6 (3.0) | Polymer A1 (80) | | PAG-A (9) | Polymer C3 (3) | PGMEA (1,160) | EL (2,706) | |

[4] EB Writing Test

Examples 3-1 to 3-38 and Comparative Examples 2-1 to 2-6

Using a coater/developer system ACT-M (Tokyo Electron Ltd.), each of the positive resist compositions R-1 to R-38 and CR-1 to CR-6 was spin coated onto a mask blank of 152 mm squares having the outermost surface of silicon oxide (vapor primed with hexamethyldisilazane (HMDS)) and prebaked on a hotplate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to EB using an EB writer system EBM-5000Plus (NuFlare Technology Inc., accelerating voltage 50 kV), then baked (PEB) at 110° C. for 600 seconds, and developed in a 2.38 wt % tetramethylammonium hydroxide (TMAH) aqueous solution, thereby yielding positive patterns.

The patterned mask blank was observed under a top-down scanning electron microscope (TD-SEM). The optimum exposure (Eop) was defined as the exposure dose ($\mu C/cm^2$) which provided a 1:1 resolution at the top and bottom of a 200-nm 1:1 line-and-space pattern. The maximum resolution of the resist was defined as the minimum line width of a line-and-space pattern that could be resolved at the optimum exposure. The LER of a 200-nm line-and-space pattern was measured under SEM. On observation in cross section of the resist pattern under SEM, it was visually judged whether or not the pattern profile was rectangular.

Separately, each resist composition was stored at 23° C. for 6 months. Like the resist composition patterned within 24 hours from preparation, the resist composition after 6-month storage was patterned to determine the optimum exposure dose (C/cm$^2$). The optimum dose change is rated "nil" when the reduction of optimum dose is 0 to less than 3%, and "changed" when the reduction of optimum dose is 3% or more.

The test results are shown in Tables 4 and 5.

TABLE 4

|  |  | Resist composition | Eop, μC/cm$^2$ | Maximum resolution, | LER, nm | Pattern profile | Optimum dose |
|---|---|---|---|---|---|---|---|
| Example | 3-1 | R-1 | 50 | 37 | 4.6 | rectangular | nil |
|  | 3-2 | R-2 | 50 | 40 | 4.8 | rectangular | nil |
|  | 3-3 | R-3 | 49 | 37 | 4.6 | rectangular | nil |
|  | 3-4 | R-4 | 51 | 45 | 4.9 | rectangular | nil |
|  | 3-5 | R-5 | 49 | 45 | 4.6 | rectangular | nil |
|  | 3-6 | R-6 | 50 | 37 | 4.8 | rectangular | nil |
|  | 3-7 | R-7 | 48 | 40 | 4.8 | rectangular | nil |
|  | 3-8 | R-8 | 48 | 37 | 4.5 | rectangular | nil |
|  | 3-9 | R-9 | 48 | 45 | 4.8 | rectangular | nil |
|  | 3-10 | R-10 | 51 | 37 | 4.6 | rectangular | nil |
|  | 3-11 | R-11 | 50 | 40 | 4.8 | rectangular | nil |
|  | 3-12 | R-12 | 50 | 37 | 4.5 | rectangular | nil |
|  | 3-13 | R-13 | 50 | 40 | 4.7 | rectangular | nil |
|  | 3-14 | R-14 | 48 | 40 | 4.7 | rectangular | nil |
|  | 3-15 | R-15 | 49 | 40 | 4.8 | rectangular | nil |
|  | 3-16 | R-16 | 50 | 37 | 4.7 | rectangular | nil |
|  | 3-17 | R-17 | 51 | 40 | 4.8 | rectangular | nil |
|  | 3-18 | R-18 | 50 | 40 | 4.7 | rectangular | nil |
|  | 3-19 | R-19 | 48 | 40 | 4.8 | rectangular | nil |
|  | 3-20 | R-20 | 49 | 45 | 4.8 | rectangular | nil |
|  | 3-21 | R-21 | 52 | 40 | 4.6 | rectangular | nil |
|  | 3-22 | R-22 | 50 | 45 | 4.7 | rectangular | nil |
|  | 3-23 | R-23 | 52 | 37 | 4.6 | rectangular | nil |
|  | 3-24 | R-24 | 52 | 37 | 4.8 | rectangular | nil |
|  | 3-25 | R-25 | 51 | 37 | 4.7 | rectangular | nil |
|  | 3-26 | R-26 | 51 | 37 | 4.6 | rectangular | nil |
|  | 3-27 | R-27 | 52 | 37 | 4.5 | rectangular | nil |
|  | 3-28 | R-28 | 52 | 37 | 4.6 | rectangular | nil |
|  | 3-29 | R-29 | 52 | 45 | 4.8 | rectangular | nil |
|  | 3-30 | R-30 | 51 | 37 | 4.4 | rectangular | nil |
|  | 3-31 | R-31 | 52 | 40 | 4.5 | rectangular | nil |
|  | 3-32 | R-32 | 50 | 40 | 4.6 | rectangular | nil |
|  | 3-33 | R-33 | 50 | 40 | 4.6 | rectangular | nil |
|  | 3-34 | R-34 | 50 | 37 | 4.6 | rectangular | nil |
|  | 3-35 | R-35 | 50 | 40 | 4.6 | rectangular | nil |
|  | 3-36 | R-36 | 51 | 40 | 4.5 | rectangular | nil |
|  | 3-37 | R-37 | 51 | 45 | 4.6 | rectangular | nil |
|  | 3-38 | R-38 | 52 | 37 | 4.8 | rectangular | nil |

TABLE 5

|  |  | Resist composition | Eop, μC/cm$^2$ | Maximum resolution, | LER, nm | Pattern profile | Optimum dose |
|---|---|---|---|---|---|---|---|
| Comparative Example | 2-1 | CR-1 | 49 | 60 | 5.6 | inversely tapered | nil |
|  | 2-2 | CR-2 | 50 | 60 | 5.8 | inversely tapered | nil |
|  | 2-3 | CR-3 | 52 | 45 | 4.7 | rectangular | nil |
|  | 2-4 | CR-4 | 49 | 45 | 4.8 | rectangular | changed |
|  | 2-5 | CR-5 | 50 | 40 | 4.7 | rectangular | changed |
|  | 2-6 | CR-6 | 52 | 45 | 4.8 | rectangular | changed |

As seen from the data in Tables, the resist compositions R-1 to R-38 containing the sulfonium compound having formula (A) within the scope of the invention exhibit a high resolution, satisfactory pattern rectangularity, and acceptable values of LER. In contrast, the comparative resist compositions CR-1 and CR-2 are inferior in resolution and LER. This is because the acid generated upon exposure diffuses into the unexposed region to induce the unwanted reaction that a few protective groups on the base polymer in the unexposed region are deprotected.

The resist compositions containing the sulfonium compound having formula (A) within the scope of the invention have a higher acid trapping ability and are less susceptible to the unwanted reaction than the resist composition CR-1 of Comparative Example 2-1 containing the comparative quencher. After imagewise exposure, the sulfonium compound having formula (A) is converted to a weakly acidic sulfonamide compound, losing the acid diffusion controlling ability. Therefore the reaction contrast between exposed and unexposed regions is enhanced. Comparative Example 2-2 is low in reaction contrast because Quencher Q-5 used therein retains the acid diffusion controlling ability even after imagewise exposure. As a result, a pattern having satisfactory resolution and reduced LER is formed from the resist composition within the scope of the invention. This suggests that even when the resist composition is applied to a processable substrate having an outermost surface made of a material to which the resist pattern profile is sensitive, such as chromium or silicon-containing material, a pattern with high resolution and reduced LER can be formed through high-energy radiation exposure because the inventive resist composition containing the specific sulfonium compound is efficient for controlling acid diffusion at the substrate interface.

The resist compositions R-1 to R-38 showed satisfactory values in terms of storage stability. The resist compositions CR-4 to CR-6 of Comparative Examples are inferior in storage stability to Examples. This inferior storage stability is ascribed to the reaction of fluorinated polymer (C) with Quencher Q-6 because the resist composition CR-3 of Comparative Example 2-3 shows no sensitivity change.

Since the sulfonium compounds having formula (A) have lower anion nucleophilicity than sulfonium compound Q-6 used in Comparative Examples 2-4 to 2-6, they are less susceptible to the unwanted reaction. Then the sulfonium compounds in resist compositions R-1 to R-38 of Examples are not consumed during storage. This leads to unchanged sensitivity and good storage stability.

[5] EB Writing Test after Coating of Anti-Charging Film

Examples 4-1 to 4-8 and Comparative Examples 3-1 to 3-2

Using a coater/developer system Clean Track Mark 8 (Tokyo Electron Ltd.), each of the positive resist compositions R-1, R-3, R-6, R-31, R-32, R-36 to R-38, CR-1 and CR-2 was spin coated onto a 6-inch silicon wafer (vapor primed with HMDS) and baked at 110° C. for 240 seconds to form a resist film of 80 nm thick. Using Clean Track Mark 8, a conductive polymer composition was dispensed dropwise and spin coated over the entire resist film and baked on a hotplate at 90° C. for 90 seconds to form an anti-charging film of 60 nm thick. The conductive polymer composition used herein was a water dispersion of polystyrene-doped polyaniline as described in Proc. of SPIE Vol. 8522 85220O-1.

The coated wafer was exposed to EB using an EB writer system HL-800D (Hitachi High-Technologies, Ltd., accelerating voltage 50 kV), rinsed with pure water for 15 seconds to strip off the anti-charging film, then baked (PEB) at 110° C. for 240 seconds, and developed in a 2.38 wt % TMAH aqueous solution for 80 seconds, thereby yielding a positive pattern.

The patterned mask blank was observed under a TD-SEM. The optimum exposure (Eop) was defined as the exposure dose (tC/cm$^2$) which provided a 1:1 resolution at the top and bottom of a 400-nm 1:1 line-and-space pattern. The maximum resolution of the resist was defined as the minimum line width of a line-and-space pattern that could be resolved at the optimum exposure. The results are shown in Table 6.

TABLE 6

|  |  | Resist composition | Eop, µC/cm$^2$ | Maximum resolution, nm |
|---|---|---|---|---|
| Example | 4-1 | R-1 | 48 | 70 |
|  | 4-2 | R-3 | 48 | 70 |
|  | 4-3 | R-6 | 49 | 60 |
|  | 4-4 | R-31 | 50 | 70 |
|  | 4-5 | R-32 | 50 | 70 |
|  | 4-6 | R-36 | 49 | 70 |
|  | 4-7 | R-37 | 48 | 60 |
|  | 4-8 | R-38 | 48 | 60 |
| Comparative Example | 3-1 | CR-1 | 47 | 80 |
|  | 3-2 | CR-2 | 47 | 90 |

As seen from the data in Table 6, the resist compositions of Examples 4-1 to 4-8 containing the sulfonium compound having formula (A) as quencher within the scope of the invention exhibit a satisfactory resolution. In contrast, the resist compositions of Comparative Examples 3-1 and 3-2 are inferior in resolution. This is because the very weak acid in the anti-charging film induces the unwanted reaction to deprotect a few protective groups on the base polymer in the unexposed region. Since the resist composition containing the inventive sulfonium compound has a higher salt exchange efficiency than the resist composition of Comparative Example 3-1 containing Quencher Q-4 and reduced in intermixing between the resist layer and the anti-charging layer as compared with Comparative Example 3-2, the likelihood of the unwanted reaction is reduced. As a result, a pattern with a higher resolution can be formed. Examples 4-3, 4-7 and 4-8 reveal that resolution is further improved by adding fluorinated polymer (C) which is effective for suppressing acid mixing.

It has been demonstrated that using the resist composition within the scope of the invention, a pattern having a very high resolution and minimal LER can be formed via exposure and development. In addition, the resist composition within the scope of the invention has improved storage stability. Even when the resist film is overlaid with an anti-charging film, the resist composition within the scope of the invention maintains a high resolution. The pattern forming process using the resist composition within the scope of the invention is advantageous in the photolithography for semiconductor device fabrication and photomask blank processing.

Japanese Patent Application No. 2018-166172 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium compound having the formula (A):

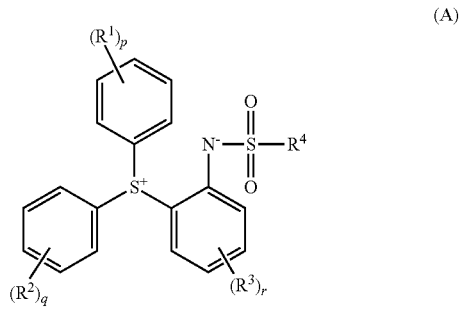

wherein $R^1$, $R^2$, $R^3$, and $R^4$ are each independently a $C_1$-$C_{20}$ monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached.

2. A positive resist composition comprising (A) a quencher containing the sulfonium compound of claim 1.

3. The positive resist composition of claim 2, further comprising (B) a base polymer containing a polymer adapted to be decomposed under the action of acid to increase its solubility in alkaline developer.

4. The positive resist composition of claim 3 wherein the polymer comprises recurring units of at least one type selected from recurring units having the formulae (B1) to (B3):

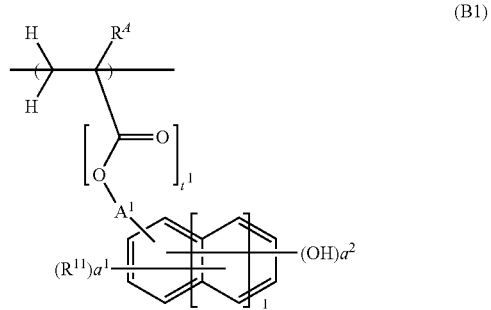

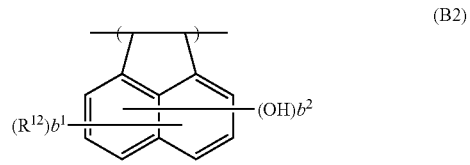

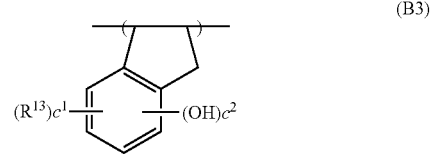

wherein $R^A$ is hydrogen, fluorine, methyl or trifluoromethyl, $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $R^{12}$ and $R^{13}$ are each independently halogen, an acetoxy group, optionally halogenated $C_2$-$C_8$ acyloxy group, optionally halogenated $C_1$-$C_8$ alkyl group, optionally halogenated $C_1$-$C_8$ alkoxy group, or optionally halogenated $C_2$-$C_8$ alkylcarbonyloxy group, $A^1$ is a single bond or $C_1$-$C_{10}$ alkanediyl group in which an ether bond may intervene in a carbon-carbon bond, $t^1$ is 0 or 1, $x^1$ is an integer of 0 to 2, $a^1$ is an integer satisfying $0 \leq a^1 \leq 5+2x^1-a^2$, $a^2$ is an integer of 1 to 3, $b^1$ is an integer of 0 to 5, $b^2$ is an integer of 1 to 3, satisfying $1 \leq b^1+b^2 \leq 6$, $c^1$ is an integer of 0 to 3, $c^2$ is an integer of 1 to 3, satisfying $1 \leq c^1+c^2 \leq 4$.

5. The positive resist composition of claim 3 wherein the polymer further comprises recurring units having the formula (B4):

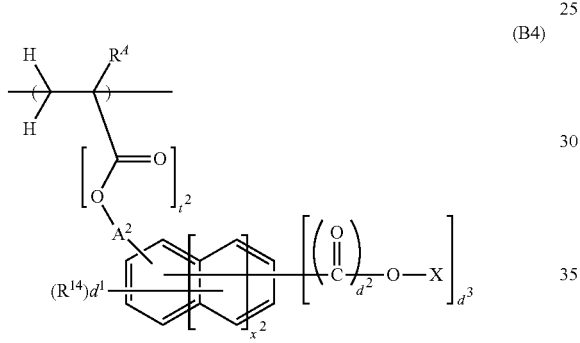
(B4)

wherein $R^A$ is hydrogen, fluorine, methyl or trifluoromethyl, $R^{14}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^2$ is a single bond or $C_1$-$C_{10}$ alkanediyl group in which an ether bond may intervene in a carbon-carbon bond, $t^2$ is 0 or 1, $x^2$ is an integer of 0 to 2, $d^1$ is an integer satisfying: $0 \leq d^1 \leq 5+2x^2-d^3$, $d^2$ is 0 or 1, $d^3$ is an integer of 1 to 3, in case of $d^3=1$, X is an acid labile group, and in case of $d^3=2$ or 3, X is each independently hydrogen or an acid labile group, at least one X being an acid labile group.

6. The positive resist composition of claim 3 wherein the polymer further comprises recurring units of at least one type selected from units having the formulae (B5) to (B7):

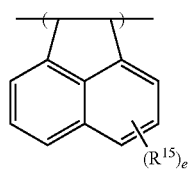
(B5)

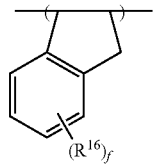
(B6)

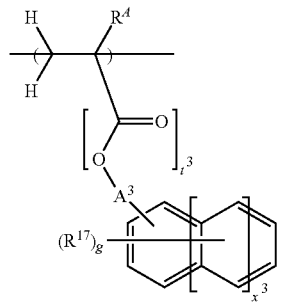
(B7)

wherein $R^A$ is hydrogen, fluorine, methyl or trifluoromethyl, $R^{15}$ and $R^{16}$ are each independently halogen, an acetoxy group, optionally halogenated $C_2$-$C_8$ acyloxy group, optionally halogenated $C_1$-$C_8$ alkyl group, optionally halogenated $C_1$-$C_8$ alkoxy group, or optionally halogenated $C_2$-$C_8$ alkylcarbonyloxy group, $R^{17}$ is an acetyl group, acetoxy group, $C_1$-$C_{20}$ alkyl group, $C_1$-$C_{20}$ alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group, $A^3$ is a single bond or $C_1$-$C_{10}$ alkanediyl group in which an ether bond may intervene in a carbon-carbon bond, e is an integer of 0 to 6, f is an integer of 0 to 4, g is an integer of 0 to 5, $t^3$ is 0 or 1, and $x^3$ is an integer of 0 to 2.

7. The positive resist composition of claim 3 wherein the polymer further comprises recurring units of at least one type selected from recurring units having the formulae (B8) to (B11):

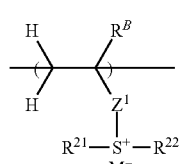
(B8)

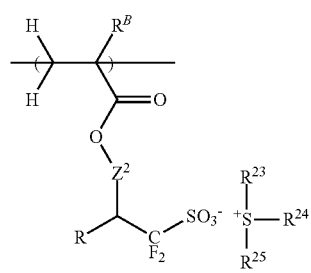
(B9)

-continued

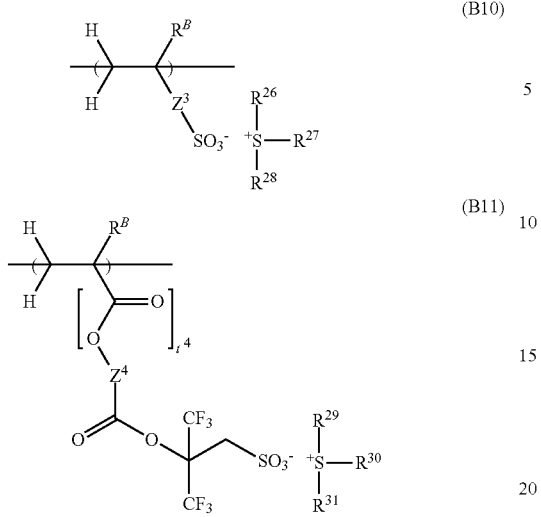

wherein $R^B$ is each independently hydrogen or methyl,
$Z^1$ is a single bond, phenylene group, —O—$Z^{11}$—, —C(=O)—O—$Z^{11}$— or —C(=O)—NH—$Z^{11}$—,
$Z^{11}$ is a $C_1$-$C_6$ alkanediyl, $C_2$-$C_6$ alkenediyl or phenylene group, which may contain a carbonyl moiety, ester bond, ether bond or hydroxyl moiety,
$Z^2$ is a single bond or —$Z^{21}$—C(=O)—O—, $Z^{21}$ is a $C_1$-$C_{20}$ divalent hydrocarbon group which may contain a heteroatom,
$Z^3$ is a single bond, methylene, ethylene, phenylene, fluorinated phenylene, —O—$Z^{31}$—C(=O)—O—$Z^{31}$— or —C(=O)—NH—$Z^{31}$—, $Z^{31}$ is a $C_1$-$C_6$ alkanediyl, $C_2$-$C_6$ alkenediyl or phenylene group, which may contain a carbonyl moiety, ester bond, ether bond or hydroxy moiety,
$Z^4$ is a single bond or a $C_1$-$C_{30}$ divalent hydrocarbon group which may contain a heteroatom, $t^4$ is 0 or 1, with the proviso that $t^4$ is 0 when $Z^4$ is a single bond,
$R^{21}$ to $R^{31}$ are each independently a $C_1$-$C_{20}$ monovalent hydrocarbon group which may contain a heteroatom, or $R^{21}$ and $R^{22}$ may bond together to form a ring with the sulfur atom to which they are attached, or any two of $R^{23}$, $R^{24}$ and $R^{25}$, any two of $R^{26}$, $R^{27}$ and $R^{28}$ or any two of $R^{29}$, $R^{30}$ and $R^{31}$ may bond together to form a ring with the sulfur atom to which they are attached,
R is hydrogen or trifluoromethyl, and
$M^-$ is a non-nucleophilic counter ion.

8. The positive resist composition of claim 2, further comprising (C) a fluorinated polymer comprising recurring units having the formula (C1) and recurring units of at least one type selected from units having the formulae (C2) to (C5):

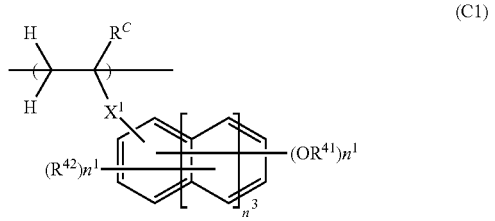

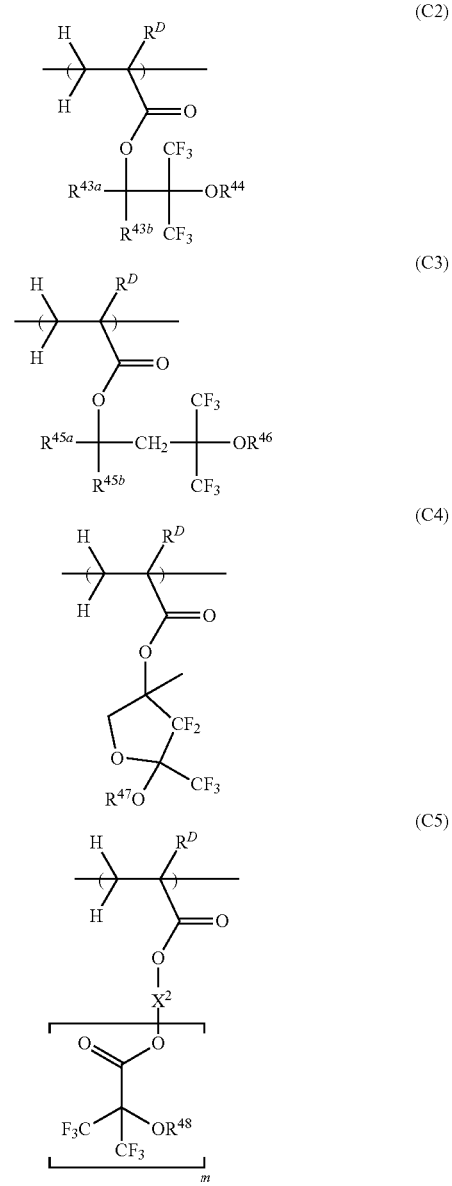

wherein $R^C$ is each independently hydrogen or methyl, $R^D$ is each independently hydrogen, fluorine, methyl or trifluoromethyl, $R^{41}$ is hydrogen or a $C_1$-$C_5$ straight or branched monovalent hydrocarbon group in which a heteroatom-containing moiety may intervene in a carbon-carbon bond, $R^{42}$ is a $C_1$-$C_5$ straight or branched monovalent hydrocarbon group in which a heteroatom-containing moiety may intervene in a carbon-carbon bond, $R^{43a}$, $R^{43b}$, $R^{45a}$ and $R^{45b}$ are each independently hydrogen or a C1-$C_{10}$ alkyl group, $R^{44}$, $R^{46}$, $R^{47}$ and $R^{48}$ are each independently hydrogen, a $C_1$-$C_{15}$ monovalent hydrocarbon group or monovalent fluorinated hydrocarbon group, or an acid labile group, with the proviso that an ether bond or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, $X^1$ is a single bond, —C(=O)—O— or —C(=O)—NH—, $X^2$ is a $C_1$-$C_{20}$ (m+1)-valent hydrocarbon group or fluorinated hydrocarbon group, $n^1$ is an integer of 1 to 3, $n^2$ is an integer satisfying: $0 \leq n^2 \leq 5+2n^3-n^1$, $n^3$ is 0 or 1, and m is an integer of 1 to 3.

9. The positive resist composition of claim 2, further comprising (D) an organic solvent.

10. The positive resist composition of claim 2, further comprising (E) a photoacid generator.

11. A resist pattern forming process comprising the steps of:
- applying the positive resist composition of claim 2 onto a substrate to form a resist film thereon,
- exposing the resist film pattern wise to high-energy radiation, and
- developing the resist film in an alkaline developer to form a resist pattern.

12. The process of claim 11 wherein the high-energy radiation is EUV or EB.

13. The process of claim 11 wherein the substrate has an outermost surface of silicon-containing material.

14. The process of claim 11 wherein the substrate is a photomask blank.

15. A photomask blank having coated thereon the positive resist composition of claim 2.

\* \* \* \* \*